US007399961B2

(12) United States Patent
Chen et al.

(10) Patent No.: US 7,399,961 B2
(45) Date of Patent: Jul. 15, 2008

(54) HIGH THROUGHPUT ION SOURCE WITH MULTIPLE ION SPRAYERS AND ION LENSES

(75) Inventors: David D. Y. Chen, Vancouver (CA); Donald J. Douglas, Vancouver (CA); Bradley B. Schneider, Bradford (CA)

(73) Assignee: The University of British Columbia, Vancouver, British Columba (CA)

( * ) Notice: Subject to any disclaimer, the term of this patent is extended or adjusted under 35 U.S.C. 154(b) by 566 days.

(21) Appl. No.: 10/475,295

(22) PCT Filed: Nov. 28, 2001

(86) PCT No.: PCT/CA01/01688

§ 371 (c)(1),
(2), (4) Date: Jun. 3, 2004

(87) PCT Pub. No.: WO02/086489

PCT Pub. Date: Oct. 31, 2002

(65) Prior Publication Data

US 2004/0206901 A1    Oct. 21, 2004

Related U.S. Application Data

(60) Provisional application No. 60/292,737, filed on Apr. 20, 2001.

(51) Int. Cl.
*H01J 49/10* (2006.01)
*G01N 30/72* (2006.01)
(52) U.S. Cl. .................. 250/288; 250/281; 250/423 R

(58) Field of Classification Search .................. 250/288
See application file for complete search history.

(56) References Cited

U.S. PATENT DOCUMENTS 4,842,701 A * 6/1989 Smith et al. .................. 204/451

(Continued)

FOREIGN PATENT DOCUMENTS

EP    1 290 712    3/2003

(Continued)

OTHER PUBLICATIONS

Asbury, G.R., Hill, Jr., H.H., "Using Different Drift Gases To Change Separation Factors (α) in Ion Mobility Spectrometry", Analytical Chemistry, 2000, vol. 72, No. 3, p. 580-584.

(Continued)

*Primary Examiner*—Robert Kim
*Assistant Examiner*—Bernard Souw
(74) *Attorney, Agent, or Firm*—Bereskin & Parr

(57) ABSTRACT

An apparatus with means for controlling ion generation is discussed. The apparatus comprises a plurality of ion sources, at least one counter electrode mounted downstream for the ion sources and at least one ion controlling element mounted relative to at least one of the ion sources. Each ion controlling element is alternated between a first condition where the operation of at least one of the ion sources is enabled and a second condition where the operation of at least one of the ion sources is disabled. This concept may also be extended to an ion source apparatus having a single ion source with an ion lens mounted relative thereto. The present invention also provides a method for controlling the operation of the aforementioned apparatus. The invention further provides an apparatus and a method for the generation of ion pulses.

78 Claims, 30 Drawing Sheets

U.S. PATENT DOCUMENTS

| | | | |
|---|---|---|---|
| 4,885,076 A * | 12/1989 | Smith et al. | 204/451 |
| 5,281,915 A * | 1/1994 | Takahama et al. | 324/464 |
| RE34,757 E | 10/1994 | Smith et al. | |
| 5,412,208 A | 5/1995 | Covey et al. | |
| 5,432,343 A | 7/1995 | Gulcicek et al. | |
| 5,495,108 A | 2/1996 | Apffel, Jr. et al. | |
| 5,747,799 A | 5/1998 | Franzen | |
| 5,750,988 A | 5/1998 | Apffel et al. | |
| 5,756,996 A * | 5/1998 | Bier et al. | 250/292 |
| 5,838,002 A | 11/1998 | Sheehan | |
| 5,838,003 A | 11/1998 | Bertsch et al. | |
| 5,869,344 A * | 2/1999 | Linforth et al. | 436/173 |
| 6,060,705 A | 5/2000 | Whitehouse et al. | |
| 6,077,334 A * | 6/2000 | Joannou | 96/66 |
| RE36,892 E | 10/2000 | Apffel, Jr. et al. | |
| 6,207,955 B1 * | 3/2001 | Wells et al. | 250/288 |
| 6,245,227 B1 * | 6/2001 | Moon et al. | 210/198.2 |
| 6,274,867 B1 * | 8/2001 | Wells et al. | 250/288 |
| 6,294,780 B1 * | 9/2001 | Wells et al. | 250/288 |
| 6,350,617 B1 | 2/2002 | Hindsgaul et al. | |
| 6,359,275 B1 | 3/2002 | Bertsch et al. | |
| 6,410,915 B1 * | 6/2002 | Bateman et al. | 250/288 |
| 6,462,337 B1 | 10/2002 | Li et al. | |
| 6,465,776 B1 | 10/2002 | Moini et al. | |
| 6,501,073 B1 | 12/2002 | Mylchreest et al. | |
| 6,541,768 B2 | 4/2003 | Andrien, Jr. et al. | |
| 6,586,731 B1 | 7/2003 | Jolliffe | |
| 6,690,004 B2 | 2/2004 | Miller et al. | |
| 6,703,611 B2 * | 3/2004 | Glish et al. | 250/288 |
| 6,996,972 B2 * | 2/2006 | Song | 60/202 |
| 7,022,982 B2 * | 4/2006 | Sobek et al. | 250/288 |
| 2001/0001452 A1 | 5/2001 | Moon et al. | |
| 2001/0001455 A1 | 5/2001 | Moon et al. | |
| 2001/0001456 A1 | 5/2001 | Moon et al. | |
| 2001/0001460 A1 | 5/2001 | Moon et al. | |
| 2001/0001474 A1 | 5/2001 | Moon et al. | |
| 2001/0007350 A1 | 7/2001 | Moon et al. | |
| 2001/0013490 A1 | 8/2001 | Moon et al. | |
| 2001/0013579 A1 | 8/2001 | Andrien et al. | |
| 2001/0016424 A1 | 8/2001 | Moon et al. | |
| 2002/0000517 A1 | 1/2002 | Corso et al. | |
| 2002/0096631 A1 | 7/2002 | Andrien et al. | |
| 2002/0117629 A1 | 8/2002 | Fujimaki et al. | |
| 2002/0121598 A1 | 9/2002 | Park | |
| 2004/0206901 A1 * | 10/2004 | Chen et al. | 250/288 |
| 2005/0117864 A1 * | 6/2005 | Dziekan et al. | 385/125 |
| 2005/0258360 A1 * | 11/2005 | Whitehouse et al. | 250/288 |
| 2006/0255261 A1 | 11/2006 | Whitehouse et al. | |

FOREIGN PATENT DOCUMENTS

| | | | |
|---|---|---|---|
| JP | 62164550 A * | 7/1987 | |
| JP | 03161363 A * | 7/1991 | |
| JP | 06183053 A * | 7/1994 | |
| JP | 2000-357488 A | 12/2000 | |
| WO | WO 99/13492 A1 | 3/1999 | |
| WO | WO 99/19899 A1 | 4/1999 | |
| WO | WO 99/50667 A1 | 10/1999 | |
| WO | WO 00/15321 | 3/2000 | |
| WO | WO 00/52455 A | 9/2000 | |
| WO | WO 01/91158 A2 | 5/2001 | |
| WO | WO 01/44795 A2 | 6/2001 | |
| WO | WO 01/50499 A1 | 7/2001 | |
| WO | WO2086489 * | 11/2001 | |
| WO | WO 01/93309 A1 | 12/2001 | |
| WO | WO 01/95367 A2 | 12/2001 | |
| WO | WO 02/08724 A2 | 1/2002 | |
| WO | WO 02 059563 A2 | 8/2002 | |

OTHER PUBLICATIONS

Bayliss, M. K.; Little, D.; Mallett, D. N.; Plumb, R.S., Parallel ultra-high flow rate liquid chromatography with mass spectrometric detection using a multiplex electrospray source for direct, sensitive determination of pharmaceuticals in plasma at extremely high throughput. Rapid Communications in Mass Spectrometry, 2000, 14, p. 2039-2045.

Beavis, R.C., An Automated Off-Line Liquid Chromatography—Mass Spectrometry Interface using Solid Phase, Time-of-Flight Secondary Ion Mass Spectrometry, Thesis Dissertation, 1987, pp. 43-46, 77-79, 82-93.

Beavis et al., An Improved Method of Target Preparation By Electrospray, Proceedings of the 31st ASMS Conference on Mass Spectrometry and Allied Topics, Boston, May 8-13, 1983, p. 679-680.

Beavis et al., Automated Dry Fraction Collection For Microbore High-Performance Liquid Chromatography-Mass Spectrometry, Journal of Chromatography, 359 (1986), pp. 489-497.

Bruins, A.P.; Covery, T.R.; Henion, J.D., "Ion Spray Interface for Combined Liquid Chromatography/Atmospheric Pressure Ionization Mass Spectrometry", Anal. Chem. 1987, 59, 2642-2646.

Bruins, A.P. "Mass spectrometry with ion sources operating at atmospheric pressure", Mass Spectrometry Reviews 1991, 10, 53-77.

Cao, P.; Moini, M., "A Novel Sheathless Interface for Capillary Electrophoresis / Electrospray Ionization Mass Spectrometry Using an In-capillary Electrode", J. Am. Soc. Mass Spectrom. 1997, 8, 561-564.

De Biasi, V.; Haskins, N.; Organ, A.; Bateman, R.; Giles, K.; Jarvis, S., High Throughput Liquid Chromatography/Mass Spectrometric Analyses Using a Novel Multiplexed Electrospray Interface. Rapid Communications in Mass Spectrometry, 1999, 13, p. 1165-1168.

Dole, M.; Mach, L.L.; Hines, R.L.; Mobley, R.C.; Ferguson, L.P.; Alice, M.B., "Molecular Beams of Macroions", J. Chem. Phys. 1968, 49, 2240-2249.

Eckers, C.; Wolff, J. C.; Haskins, N. J.; Sage, A. B.; Giles, K.; Bateman, R. Accurate Mass Liquid Chromatography/Mass Spectrometry on Orthogonal Acceleration Time-of-Flight Mass Analyzers Using Switching between Separate Sample and Reference Sprays. 1. Proof of Concept. Analytical Chemistry, Aug. 15, 2000, vol. 72, No. 16, p. 3683-3688.

Feng, Xiao and Agnes, George R. Single Isolated Droplets With Net Charge as a Source of Ions, J Am Soc Mass Spectrom 2000, 11, pp. 393-399.

Figeys, D.; Aebersold, R., "High sensitivity identification of proteins by electrospray ionization tandem mass spectrometry: Initial comparison between an ion trap mass spectrometer and a triple quadrupole mass spectrometer", Electrophoresis, 18, 1997, 360-368.

Figeys, D.; Ning, Y.; Aebersold, R., "A Microfabricated Device for Rapid Protein Identification by Microelectrospray Ion Trap Mass Spectrometry", Anal. Chem. 1997, 69, 3153-3160.

Flora, J. W.; Hannis, J. C.; Muddiman, D. C., High-Mass Accuracy of Product Ions Produced by SORI-CID Using a Dual Electrospray Ionization Source Coupled with FTICR Mass Spectrometry. Analytical Chemistry, A-E.

Hannis, J. C.; Muddiman, D. C., A Dual Electrospray Ionization Source Combined With Hexapole Accumulation to Achieve High Mass Accuracy of Biopolymers in Fourier Transform Ion Cyclotron Resonance Mass Spectrometry. Journal of American Society for Mass Spectrometry, 2000, 11, p. 876-883.

Hiller, D. L.; Brockman, A. H.; Goulet, L.; Ahmed, S.; Cole, R. O.; Covey, T., Application of a non-indexed dual sprayer pneumatically assisted electrospray source to the high throughput quantitation of target compounds in biological fluids. Rapid Communications in Mass Spectrometry, 2000, 14, p. 2034-2038.

Hofstadler et al., "Analysis of Single Cells with Capillary Electrophoresis Electrospray Ionizatio Fourier Transform Ion Cycloton Resonance Mass Spectrometry", Rapid Communications in Mass Spectrometry, vol. 10, 1996, p. 919-922.

Hong, C. M.; Tsai, F. C.; Shiea, J., A Multiple Channel Electrospray Source Used To Detect Highly Reactive Ketenes from a Flow Pyrolyzer. Analytical Chemistry, Mar. 15, 2000, vol. 72, No. 6, p. 1175-1178.

Iribarne et al., "On the evaporation of small ions from charged droplets", J. Chem. Phys., 1976, 64, pp. 2287-2294.

Jiang, L.; Moini, M.; Development of Multi-ESI-Sprayer, Multi-Atmospheric-Pressure-inlet Mass Spectrometry and Its Application to Accurate Mass Measurement Using Time-of-Flight Mass Spectrometry. Analytical Chemistry, Jan. 1, 2000, vol. 72, No. 1, p. 20-24.

Kebarle, P.; Tang, L., "From Ions in Solution to Ions in the Gas Phase", Analytical Chemistry, 1993, 65, 972A-986A.

Kostiainen, K; Bruins, A. P, Effect of Multiple Sprayers on Dynamic Range and Flow Rate Limitations in Electrospray and Ionspray Mass Spectrometry. P. 549-558 (1994).

Kyranos, J. N.; Cai, H; Wei, D; Goetzinger, W. K., High-throughput high-performance liquid chromatography/mass spectrometry for modern drug discovery. Current Opinion in Biotechnology 2001, 12, p. 105-111.

Lee, C. Y.; Shiea, J., Gas Chromatography Connected to Multiple Channel Electrospray Ionization Mass Spectrometry for the Detection of Volatile Organic Compounds. Analytical Chemistry, vol. 70, No. 13, Jul. 1, 1998, p. 2757-2761.

Liu, H. et al., Development of Multichannel Devices with an Array of Electrospray Tips for High-Throughput Mass Spectrometry. Analytical Chemistry, vol. 72, No. 14, Jul. 15, 2000, p. 3303-3310.

Lu et al., "Pulsed Electrospray for Mass Spectrometry", Analytical Chemistry, 2001, 73, pp. 4748-4753.

Morrison et al., An Evaluation of a Four-Channel Multiplexed Electrospray Tandem Mass Spectrometry for Higher Throughput Quantitative Analysis, Anal. Chem. 2002, vol. 74, No. 8, Apr. 15, 2002, pp. 1896-1902.

Ogorzalek Loo, R. R.; Udseth, H. R.; Smith, R. D., A New Approach for the Study of Gas-Phase Ion-Ion Reactions Using Electrospray Ionization. Journal of American Society for Mass Spectrometry 1992, 3, p. 695-705.

Ogorzalek Loo, R. R.; Udseth, H. R.; Smith, R. D., Evidence of Charge Inversion in the Reaction of Singly Charged Anions with Multiply Charged Macroions. The Journal of Physical Chemistry, vol. 95, No. 17, 1991, p. 6412-6415.

Ogorzalek Loo, R. R.; Winger, B. E.; Smith, R. D., Proton Transfer Reaction Studies of Multiply Charged Proteins in a High Mass-to-Charge Ratio Quadrupole Mass Spectrometer. Journal of American Society for Mass Spectrometry 1994, 5, p. 1064-1071.

Rulison, A. J.; Flagan, R. C., Scale-up of electrospray atomization using linear arrays of Taylor cones. Rev. Sci. Instrum. 64 (3), Mar. 1993, p. 683-686.

Schmelzeisen-Redeker et al., "Desolvation of Ions and Molecules in Thermospray Mass Spectrometry", Int. J. Mass Spectrom. Ion Processes, 1989, 90, pp. 139-150.

Schneider, B.B.; Chen, D.D.Y., "Collision-Induced Dissociation of Ions within the Orifice-Skimmer Region of an Electrospray Mass Spectrometer", Anal. Chem. 2000, 72, 791-799.

Schneider, B.B.; Douglas, D.J.; Chen, D.D.Y., "An atmospheric pressure ion lens to improve electrospray ionization at low solution flow-rates", Rapid Commun. Mass Spectrom. 2001, 15, 2168-2175.

Severs, J.C.; Smith, R.D., "Characterization of the Microdialysis Junction Interface for Capillary Electrophoresis/Microelectrospray Ionization Mass Spectrometry", Anal. Chem. 1997, 69, 2154-2158.

Shia, J.; Wang, C. H., Applications of Multiple Channel Electrospray Ionization Sources for Biological Sample Analysis. JMS Letters. Journal of Mass Spectrometry 1997, vol. 32, p. 247-250.

Smith, A.D.; Moini, M., "Control of Electrochemical Reactions at the Capillary Electrophoresis Outlet/Electrospra Emitter Electrode under CE/ESI-MS through the Application of Redox Buffers", Anal. Chem. 2001, 73, 240-246.

Smith et al., Capillary Zone Electrophoresis—Mass Spectrometry Using an Electrospray Ionization Interface, Analytical Chemistry, vol. 60, No. 5, Mar. 1, 1988, p. 436-441.

Smith et al., On-Line Mass Spectrometric Detection for Capillary Zone Electrophoresis, Anal. Chemistry, 1987, 59, 1230-1232.

Standing, K.G. et al., Secondary Ion Mass Spectrometry By Time-of-Flight, International Journal of Mass Spectrometry and Ion Physics, 53 (1983), pp. 125-134.

Takahashi, Y.; Fujimaki, S.; Kobayashi, T.; Morita, T.; Higuchi, T., Accurate mass determination by multiple sprayers nano-electrospray mass spectrometry on a magnetic sector instrument. Rapid Communications in Mass Spectrometry, 2000, 14, p. 947-949.

Takahashi et al., "Accurate Mass measurement using multiple sprayer nano-electrospray mass spectrometry combined with nano-scale high-performance liquid chromatography on a magnetic sector instrument", J. Chromatography B: Analytical Technologies in the Biomedical and Life Sciences 2002, 776(1) 31-38.

Tang Keqi et al., Generation of Multiple Electrosprays Using Microfabricated Emitter Arrays for Improved Mass Spectrometric Sensitivity, Anal. Chem. 2001, vol. 73, No. 8, Apr. 15, 2001, pp. 1658-1663.

Van Pelt, C. K.; Corso, T. N.; Schultz, G. A.; Lowes, S; Henion, J, A Four-Column Parallel Chromatography System for Isocratic or Gradient LC/MS Analyses. Analytical Chemistry, Feb. 1, 2001, vol. 73, No. 3, p. 582-588.

Wahl, J.H.; Gale, D.C.; Smith, R.D., "Sheathless capillary electrophoresis-electrospray ionization mass spectrometry using 10 µm I.D. capillaries: analyses of tryptic digests of cytochrome $c$", J. Chromatrogr. A. 1994, 659, 217-222.

Wang, T.; Zeng, L.; Cohen, J.; Kassel, D. B., A Multiple Electrospray Interface for Parallel Mass Spectrometric Analyses of Compound Libraries. Combinatorial Chemistry & High Throughput Screening, 1999, vol. 2, No. 6., p. 327-334.

Whitehouse, C.M.; Dreyer, R.N.; Yamashita, M.; Fenn, J.B., "Electrospray Interface for Liquid Chromatographs and Mass Spectrometers", Anal. Chem. 1985, 57, 675-679.

Wilm, M.; Mann, M., "Analytical Properties of the Nanoelectrospray Ion Source", Anal. Chem. 1996, 68, 1-8.

Wolff, J. C.; Eckers, C.; Sage, A. B.; Giles, K.; Bateman, R., Accurate Mass Liquid Chromatography/Mass Spectrometry on Quadrupole Orthogonal Acceleration Time-of-Flight Mass Analyzers Using Switching between Separate Sample and Reference Sprays. 2. Applications Using the Dual-Electrospray Ion Source. Analytical Chemistry, Jun. 1, 2001, vol. 73, No. 11, p. 2605-2612.

Yamashita, M.; Fenn, J.D., "Electrospray Ion Source. Another Variation on the Free-Jet Theme", J. Phys. Chem, 1984, 88, 4451-4459.

Yamashita, M.; Fenn, J.D., "Negative Ion Production with the Electrospray Ion Source", J. Phys. Chem, 1984, 88, 4671-4675.

Yang, L; Mann, T. D.; Little, D.; Wu, N; Clement, R. P.; Rudewicz, P. J., Evaluation of a Four-Channel Multiplexed Electrospray Triple Quadrupole Mass Spectrometer for the Simultaneous Validation of LC/MS/MS Methods in Four Different Preclinical Matrixes. Analytical Chemistry, Apr. 15, 2001, vol. 73, No. 8, p. 1740-1747.

Zeng, L; Kassel D.B., Developments of a Fully Automated Parallel HPLC/Mass Spectrometry System for the Analytical Characterization and Preparative Purification of Combinatorial Libraries. Analytical Chemistry, vol. 70, No. 20, Oct. 15, 1998, p. 4380-4388.

Zhang, B.; Foret, F.; Karger, B.L. "A Microdevice with Integrated Liquid Junction for Facile Peptide and Protein Analysis by Capillary Electrophoresis/Electrospray Mass Spectrometry", Anal. Chem. 2000, 72, 1015-1022.

Exam Report for corresponding European patent application No. 01274153.4, dated Aug. 22, 2007

International Preliminary Exam Report for international application No. PCT/CA01/000728, date of completion of report, May 22, 2003.

International Search report for international application No. PCT/CA01/000728, date of publication of the international search report: Dec. 19, 2002.

Exam report for European patent application No. 01935868.8, dated Jul. 11, 2005.

* cited by examiner

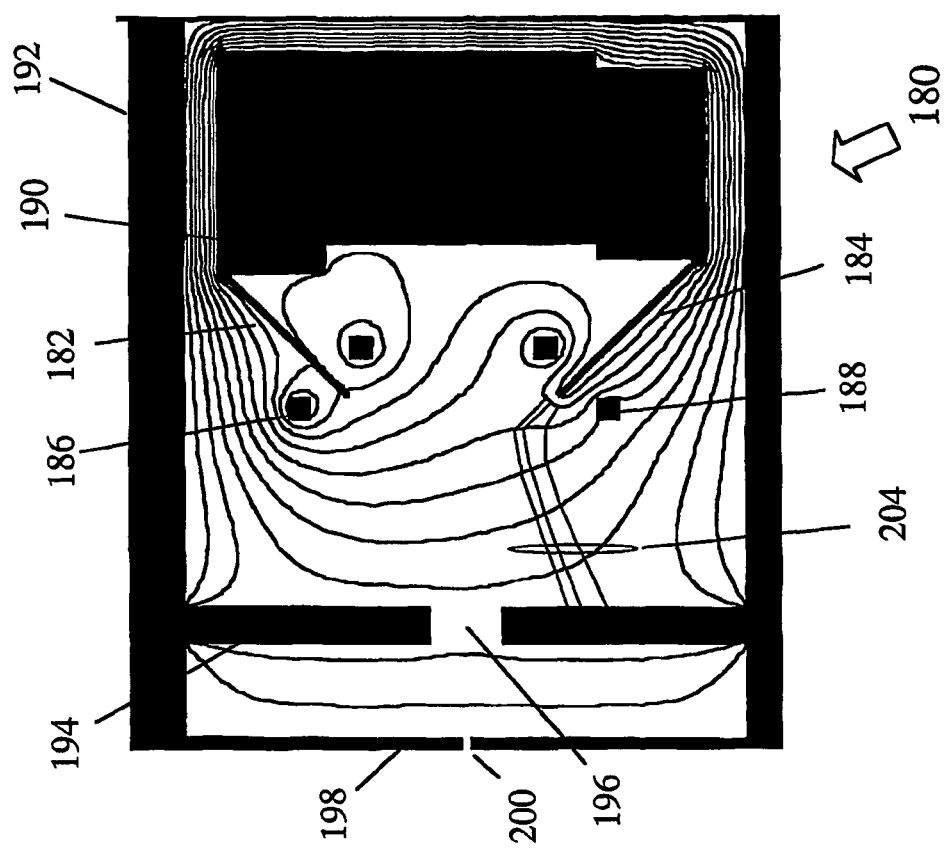
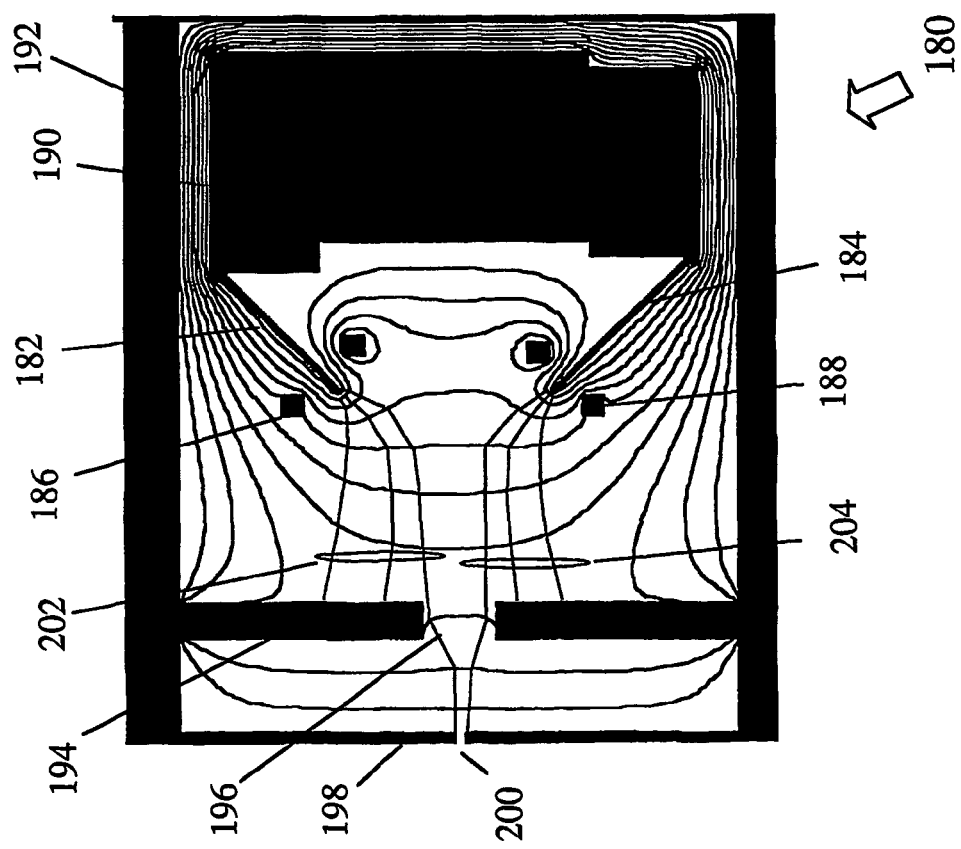
Figure 17b
Figure 17a

HIGH THROUGHPUT ION SOURCE WITH MULTIPLE ION SPRAYERS AND ION LENSES

FIELD OF THE INVENTION

The present invention relates to ion sources such as, but not limited to, ion spray, electrospray, reduced liquid flow rate electrospray, reduced liquid flow rate ion spray, and nanospray ion sources. More particularly, this invention relates to an apparatus and method for controlling ion generation from ion sources.

BACKGROUND OF THE INVENTION

Electrospray ionization (ESI) is a method of generating ions in the gas phase at relatively high pressure. ESI was first proposed as a source of ions for mass analysis by Dole et al. (*J. Chem. Phys.* 1968, 49, pp. 2240-2249). The various teachings of Fenn et al. (*J. Phys. Chem.* 1984, 88, pp. 4451-4459; *J. Phys. Chem.* 1984, 88, pp. 4671-4675; *Anal. Chem.* 1985, 57, pp. 675-679) helped to demonstrate the potential of ESI for mass spectrometry. Since then, ESI has become one of the most commonly used types of ionization techniques due to its versatility, ease of use, and effectiveness for large biomolecules.

ESI involves applying a high electric potential to a liquid sample flowing through a capillary (herein referred to as a sprayer). Droplets from the liquid sample become charged and an electrophoretic type of charge separation occurs. In positive ion mode ESI, positive ions migrate downstream towards the meniscus of the liquid at the tip of the capillary. Negative ions are attracted towards the capillary and this results in charge enrichment. Subsequent fissions (Schmeizeisen-Redeker et al., *Int. J. Mass Spectrom. Ion Processes*, 1989, 90, pp. 139-150) or evaporation (Iribarne et al., *J. Chem. Phys.*, 1976, 64, pp. 2287-2294) of the charged droplet result in the formation of single solvated gas phase ions (Kebarle et al., *Anal. Chem.*, 1993, 65, pp. 972A-986A). For mass spectrometry, these ions are then usually transmitted to the aperture of a downstream analysis device such as a quadrupole mass spectrometer, a time-of-flight mass spectrometer, an ion trap mass spectrometer, an ion cyclotron resonance mass analyzer, an electric sector, a magnetic sector or the like.

Ion spray ionization is a form of ESI in which a nebulizer gas flow is used to promote an increase in droplet fission (Bruins et al., *Anal. Chem.*, 1987, 59, pp. 2642-2646). The nebulizer gas aids in the break-up of droplets formed at the capillary tip. Ions formed in this manner can be directed into the first chamber of various mass spectrometers which include, but are not limited to, quadrupoles, time-of-flight, ion traps, ion cyclotron resonance, and sector mass spectrometers. In addition, the nebulizer gas flow may be heated (Turbo IonSpray™) to aid in desolvation of the charged droplets.

In either electrospray or ion spray ionization, an ion spray is a spray of ionized or charged droplets that are generated from an ion source. The ion source may be a sprayer comprising a capillary which is provided with a sample from which the ions are generated. The capillary is further adapted to have an electric potential applied thereto. In addition, the sample flow rate through the capillary may vary. In some cases, the sample flow rate may be reduced to the order of hundreds of nanoliters per minute in which case the sprayer is referred to as a reduced flow-rate sprayer. The sample flow-rate may further be reduced to the order of nanoliters per minute in which case the sprayer is referred to as a nanosprayer. The sprayer may further have a heated element to provide heat to a nebulizer gas which may be provided to the sprayer in the case of a Turbo IonSpray™ ion source.

In mass spectrometry, considerable time is wasted in performing multiple analyses while samples are manipulated in upstream processing. For example, in high-performance liquid chromatography mass spectrometry (HPLC-MS), the samples must first be separated. Accordingly, analytes of interest may only elute from a sample within a narrow time window that is 15-18 minutes after the start of an HPLC-MS analysis (which may last for 20 minutes). Therefore, a conventional HPLC-MS system equipped with a single sprayer collects meaningless data for the first 15 minutes and the last 2 minutes of each analysis. This inefficient use of time is compounded for laboratories which analyze thousands of samples per week.

To address this issue, a mass spectrometer with an ion source employing multiple sprayers (i.e. a multisprayer ion source) may be used for multiple analyses by staggering the start time of each analysis. For example, four HPLC-MS analyses may be staggered in a mass spectrometer with an ion source having four sprayers by commencing the first analysis at time $t_0$, the second analysis at time $t_0+5$ minutes, the third analysis at time $t_0+10$ minutes and the fourth analysis at time $t_0+15$ minutes. The analytes of interest will then be sampled from the first sprayer between 15 to 18 minutes after time $t_0$, from the second sprayer between 20 to 23 minutes after time $t_0$, from the third sprayer between 25 to 28 minutes after time $t_0$ and from the fourth sprayer between 30 to 33 minutes after time $t_0$. In this fashion, 13 analyses may be conducted within 80 minutes. In contrast, a mass spectrometer with an ion source having one sprayer will only permit 4 analyses to be conducted within the same 80 minute time frame.

Multisprayer ion sources require control of each sprayer for high-throughput operation and to facilitate any desired test protocol in which sprayers are simultaneously operated, sequentially operated or any combination thereof. Accordingly, various techniques for controlling multiple sprayers have been disclosed in the prior art. For instance, Andrien et al. (WO 99/13492) disclose an apparatus having several sprayer probes (i.e. sources) for introducing multiple samples and calibration solutions into an atmospheric pressure ion source for mass spectrometry. Andrien et al. state that the mixture of samples and/or solvents may be sprayed simultaneously or individually in a variety of combinations. To turn off the ion spray generated by a sprayer, Andrien et al. turn off the sample delivery system that provides the sample solution flow to that sprayer. Andrien et al. further disclose that applying an appropriate potential to the tip of the sprayer may be used to disable the sprayer. Andrien et al. also state that if a reservoir is used as a sample solution source, the liquid flow to the sprayer may be controlled by turning the nebulizer gas flow on or off.

However, using the sample delivery system or the nebulizer gas flow to disable or re-enable a sprayer may require several seconds. For instance, when the sample delivery system is used to disable a sprayer, the ion spray generated by the sprayer continues until the sample solution has completely drained from the transfer capillary leading to the sprayer due to residual pressure within the capillary. This problem is compounded for ion sources operating at very low sample solution flow rates. There are also situations in which shutting down the nebulizer gas flow only affects ion spray stability and does not disable a sprayer.

Furthermore, when the voltage applied to a sprayer is used to disable and re-enable a sprayer, there are undesirable effects such as time delays for sprayer stabilization due to changes in applied voltage. In addition, a droplet may form at the sprayer tip, when the voltage applied to the sprayer is turned off, which will impede the sprayer from immediately generating an ion spray with the re-application of a potential to the sprayer.

Another prior art method to control sprayers in a multi-sprayer ion source involves having each sprayer generate an ion spray that enters a downstream mass spectrometer via multiple inlet apertures and then utilizing an electric field within the mass spectrometer to deflect the ion sprays towards or away from further stages of the mass spectrometer. This is done by placing an electrode downstream from the entrance aperture of the mass spectrometer and applying an appropriate potential to either transmit or deflect ions as disclosed by Kato (JP2000/357488) and Covey (WO 01/44795). For this method, Covey teaches that sprayer stabilization is not an issue since the sprayers are always on.

These types of mass spectrometers are effective for the elimination of sample carry-over from one sprayer to the next. However, the vacuum pumping requirements and associated costs for these mass spectrometers can become very large when multiple inlet apertures are installed onto the mass spectrometer. Hence, the number of sprayers and inlet apertures is limited by the vacuum chamber pumping requirements of the mass spectrometer. It is also not apparent how the focusing/deflecting electrode within the first vacuum stage affects the overall sensitivity of the mass spectrometer.

Another approach in the prior art to control sprayers in a multisprayer ion source involves moving a selected sprayer in front of the inlet aperture of a mass spectrometer. For instance, Hindsgaul et al. (WO 99/50667) disclose mounting a plurality of sprayers on a wheel and rotating the wheel in front of the inlet aperture of a mass spectrometer. Alternatively, Hannis et al. (*J Am Soc Mass Spectrom* 2000, 11, pp. 876-883) disclose a dual ion source having two sprayers and a solenoid that is actuated to line up one of the two sprayers in front of the heated capillary inlet of a downstream mass spectrometer.

Another mechanical method involves keeping all sprayers generating ions continuously and employing a mechanical device to block the ion spray from each sprayer except for one sprayer which is aligned with an aperture contained in the blocking device as disclosed by Hindsgaul et al. (WO 99/50667) and Covey et al. (WO 01/44795). Other devices incorporating this concept are disclosed in Wang et al. (*Comb. Chem. High Throughput Screening*, 1999, 2, pp. 327-334), De Biasi et al. (*Rapid Commun. Mass Spectrom.*, 1999, 13, pp. 1 165-1168), and Wolff et al. (*Anal. Chem.*, 2001, 73, pp. 2605-2612).

Although, mechanical devices are more effective for selecting the ion spray generated by a given sprayer than varying sprayer potential or sample solution flow rate, mechanical devices tend to decrease the overall sensitivity of the ion source (Yang et al., *Anal. Chem.*, 2001, 73, pp. 1740-1747). There is also the possibility for sample carry-over from one sprayer to the next. Mechanical systems are also prone to reliability concerns. Furthermore, Covey et al. (WO 01/44795) stated that mechanical methods suffer from the time delay incurred from the mechanical positioning of the blocking device and that excessive liquid impacting a rotating mechanical device may result in excessive background interferences.

SUMMARY OF THE INVENTION

The present invention provides an ion controlling means to disable and re-enable a sprayer in either a single sprayer ion source apparatus or a multisprayer ion source apparatus. The ion controlling means comprises an ion lens mounted relative to the tip or outlet of the sprayer that it is controlling (i.e. either disabling or enabling). Alternatively, the ion controlling means may be located relative to more than one sprayer.

In accordance with the preferred embodiments, the present invention provides an apparatus for controlling the generation of ions. The apparatus comprises at least one ion source adapted for generating ions from a sample. The apparatus further includes at least one counter electrode which is located downstream from the at least one ion source. The at least one ion source and the at least one counter electrode are adapted to enable downstream movement of the generated ions upon application of a potential difference between the at least one ion source and the at least one counter electrode. The apparatus also includes at least one ion controlling element mounted relative to the at least one ion source. In use, a potential is applied to the at least one ion source and the at least one ion source is operable in a first condition where the at least one ion controlling element enables ion generation by the at least one ion source and a second condition where the at least one ion controlling element disables ion generation by the at least one ion source. The apparatus further includes alternating means for alternating the at least one ion controlling element between the first condition and the second condition.

The apparatus may further be adapted such that the alternating means comprises an enabling potential applied to the at least one ion controlling element in the first condition to enable the at least one ion source and a disabling potential applied to the at least one ion controlling element in the second condition to disable the at least one ion source.

Alternatively, the apparatus may be further adapted such that the alternating means comprises a translation means that is operatively coupled to the at least one ion controlling element to translate the at least one ion controlling element to an enabling position in the first condition and to a disabling position in the second condition.

In a further alternative, the apparatus may be adapted such that the alternating means comprises a combination of a translation means and an enabling potential which are applied to the at least one ion controlling element in the first condition and a combination of a translation means and a disabling potential which are applied to the at least one ion controlling element in the second condition.

In another aspect, the apparatus may be further adapted such that the alternating means comprises a switching means that is connectable to the at least one ion controlling element for providing a rapidly alternating potential to the at least one ion controlling element. In this case, the at least one ion source is adapted to generate ion pulses.

The apparatus may further comprise a plurality of ion sources and a plurality of ion controlling elements in which case the apparatus may further comprise an electrode means that is located centrally with respect to the plurality of ion sources. In use, a potential is applied to the electrode means for isolating each ion source from the potentials applied to ion controlling elements mounted relative to other ion sources from the plurality of ion sources. The apparatus may further comprise a power supply means to provide a separate potential to each of the plurality of ion sources.

In a further aspect, the apparatus comprises a sprayer mount having a plurality of sprayer mounting means for adjustably mounting each of the ion sources. The apparatus also includes a biasing means for applying a potential to each ion source and each ion controlling element, and a sample delivery means for providing a sample to each ion source.

In yet a further aspect, the apparatus may further comprise an attachment piece which is removably connectable to the sprayer mount for connecting additional ion sources to the apparatus.

In another aspect, the invention provides a method for controlling ion generation from a sample. The method comprises:

a) supplying the sample to at least one ion source;
b) generating ions from the sample;
c) applying a potential to at least one ion controlling element mounted relative to the at least one ion source; and,
d) alternating the at least one ion controlling element between a first condition where ion generation by the at least one ion source is enabled and a second condition where ion generation by the at least one ion source is disabled.

Alternating the at least one ion controlling element between the first condition and the second condition may be effected by applying an enabling potential to the at least one ion controlling element in the first condition and applying a disabling potential to the at least one ion controlling element in the second condition.

Alternatively, alternating the at least one ion controlling element between the first condition and the second condition may be effected by moving the at least one ion controlling element to an enabling position in the first condition and moving the at least one ion controlling element to a disabling position in the second condition.

Alternatively, alternating the at least one ion controlling element between the first condition and the second condition may be effected by a combination of applying an enabling potential and moving the at least one ion controlling element to an enabling position in the first condition and a combination of applying a disabling potential and moving the at least one ion controlling element to a disabling position in the second condition.

In a further aspect, the method may comprise generating pulses of ions by rapidly applying the enabling potential and the disabling potential to the at least one ion controlling element in an alternating fashion.

Alternatively, the method may further comprise providing a potential to an electrode means located centrally with respect to a plurality of ion sources for isolating each ion source from the potentials applied to the ion controlling elements that are mounted relative to other ion sources from said plurality of ion sources.

The method may further comprise providing a different potential to each ion source that is enabled for increasing the number of ions generated therefrom.

In addition, the method may further comprise generating ions of one polarity from at least one of the plurality of ion sources and generating ions of the opposite polarity from at least one other ion source from the plurality of ion sources to investigate ion-ion chemistry.

BRIEF DESCRIPTION OF THE DRAWINGS

For a better understanding of the present invention and to show more clearly how it may be carried into effect, reference will now be made, by way of example only, to the accompanying drawings which show preferred embodiments of the present invention and in which:

FIG. 17a is a simulation result for a dual sprayer ion source with both sprayers operational;

FIG. 17b is a simulation result for a dual sprayer ion source with one operational sprayer and one disabled sprayer;

DETAILED DESCRIPTION OF THE INVENTION

In this description, all applied potentials are DC voltages. The ion lenses described herein are also referred to as ion controlling elements and are generally known to those skilled in the art as lens electrodes or ring electrodes. Furthermore, the sprayers referred to herein may also be considered to be ion sources. In addition, all simulation results shown herein were obtained using the MacSIMION version 2.0 simulation program.

Furthermore, an ion spray will be understood by those skilled in the art to be a spray of ionized or charged droplets which are generated by a sprayer. In addition, the measured ion signals in the experiments described herein and the graphs shown herein are understood to have come from the ion spray(s) generated by operational or enabled sprayer(s).

Figure 1:
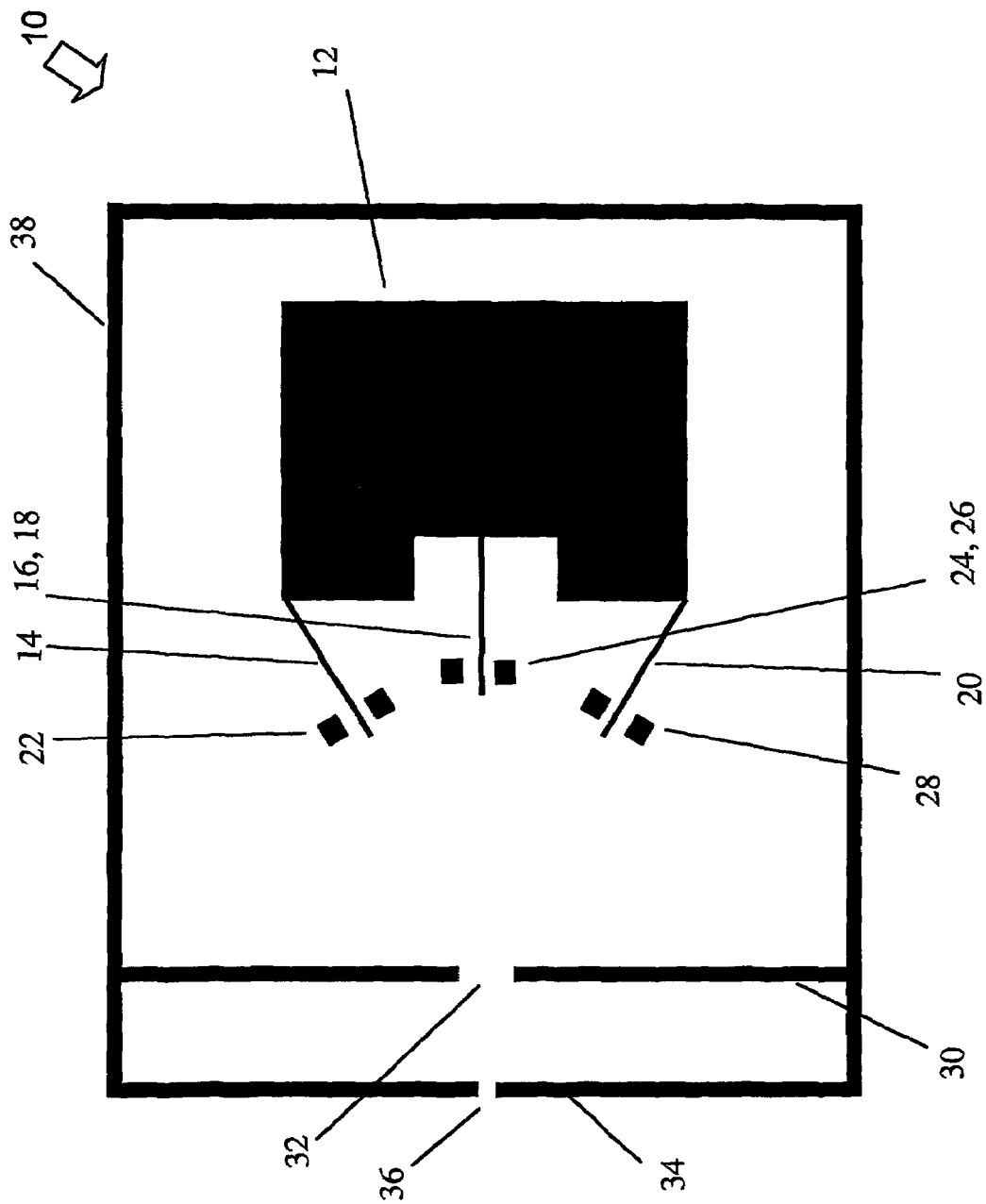
FIG. 1 is a schematic of a multisprayer ion source in accordance with the present invention.

Referring now to FIG. 1, shown therein is an embodiment of a multisprayer ion source 10 in accordance with the present invention. The multisprayer ion source 10 comprises a sprayer mount 12, sprayers 14, 16, 18 and 20 each mounted on the sprayer mount 12 and ion controlling elements such as ion lenses 22, 24, 26 and 28 each mounted relative to a respective sprayer 14, 16, 18 and 20 as will be further discussed below. The multisprayer ion source 10 further comprises a curtain plate 30 having an aperture 32, an orifice plate 34 having an orifice 36 and a housing 38. There are also power supplies (not shown) that are used to apply potentials to various components of the multisprayer ion source 10 as further discussed below. It will be understood by those skilled in the art that the curtain plate 30 and the orifice plate 34 may be replaced with a heated capillary or other type of inlet.

The curtain plate 30, the orifice plate 34, and the housing 38 serve as counter electrodes for the multisprayer ion source 10. Furthermore, any other ion lenses or detectors downstream of the ion source may serve as counter electrodes if the ion lenses or detectors are at a potential lower than the potential applied to the sprayers 14, 16, 18 and 20. Alternatively, any of the ion lenses 22, 24, 26 and 28 may serve as counter-electrodes if the potentials applied to these ion lenses are lower in magnitude than the potential applied to the sprayers 14, 16, 18 and 20 on which they are mounted.

The region between the curtain plate 30 and the orifice plate 34 may be at atmospheric pressure and may be flushed with a gas such as nitrogen. The rest of the interior of the housing 38 may also be at atmospheric pressure. The orifice plate 34 further acts to separate the atmospheric pressure region in the housing 38 from any elements downstream from the multisprayer ion source 10 such as the first stage of a mass spectrometer or the like. Preferably, the interior of the housing 38 is at atmospheric pressure, but this is not essential.

In FIG. 1, four sprayers 14, 16, 18 and 20 are shown for illustrative purposes only (sprayer 18 and ion lens 26 are not visible in FIG. 1). In practice, the multisprayer ion source 10 may have as little as two sprayers or may have more than four sprayers. The number of sprayers in the multisprayer ion source 10 may vary depending upon the physical dimensions of the various components of the multisprayer ion source 10 as well as the intended applications for the multisprayer ion source 10. However, in each embodiment an ion lens would be mounted relative to each sprayer in the multisprayer ion source 10.

Furthermore, although the embodiments shown herein illustrate multisprayer ion sources, the ion controlling scheme of the subject invention may also be applied to a single sprayer ion source having an ion lens mounted relative to the sprayer. This is supported by experimental results shown further below.

Figure 2:
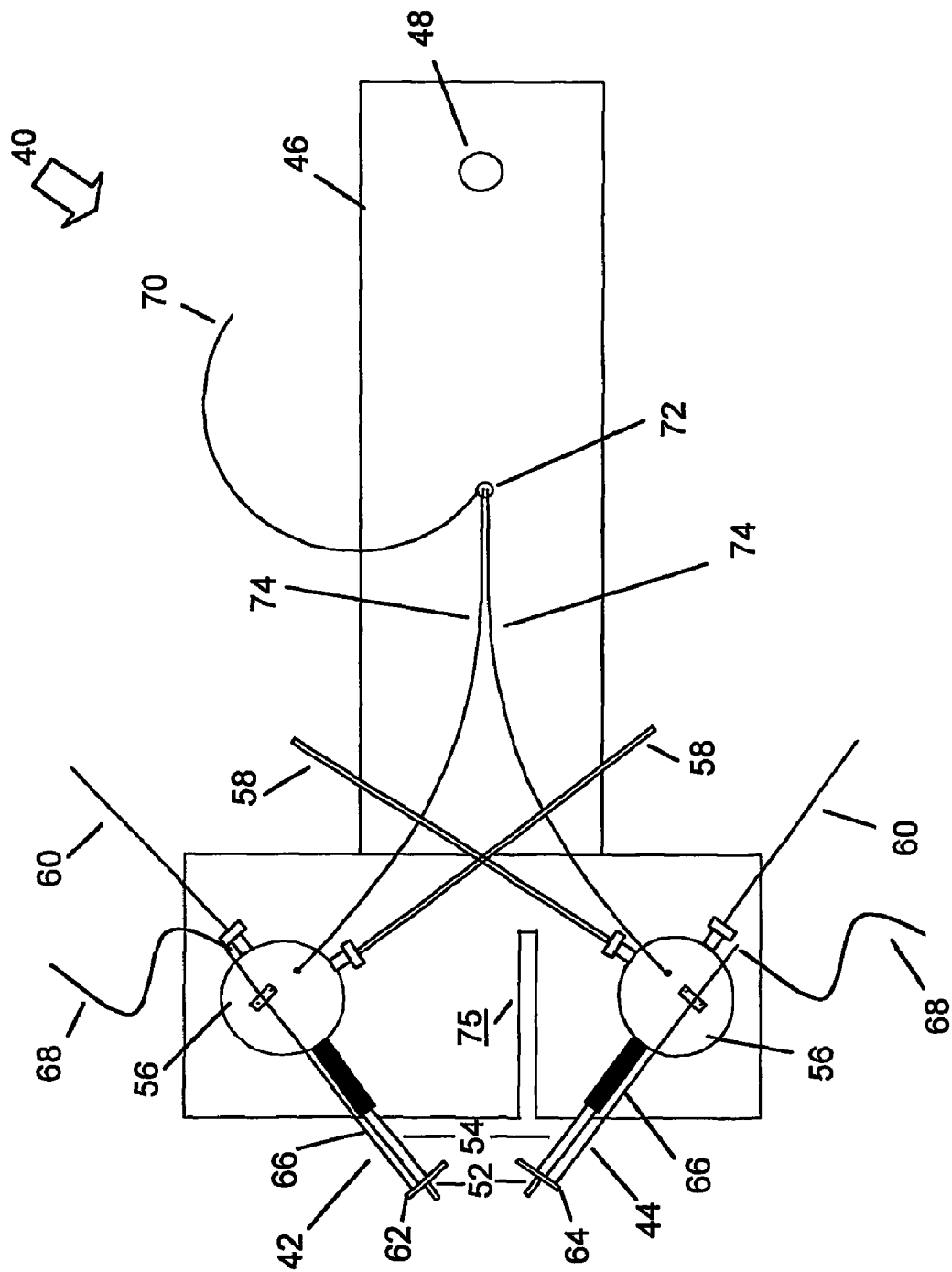
FIG. 2 is a top view of a dual sprayer apparatus.

The sprayers 14, 16, 18 and 20 are each mounted on the sprayer mount 12 so that the ion spray generated by each sprayer is directed towards the aperture 32 and the orifice 36. Accordingly, the sprayers 14, 16, 18 and 20 may be aligned in a parallel fashion or they may be angled towards the aperture 32 and the orifice 36 on an angle such as, but not limited to, 45 degrees. It will be apparent to those skilled in the art that the sprayers 14, 16, 18 and 20 could have straight shafts, as illustrated in FIGS. 1 and 2, or curved shafts with a straight end piece on which an ion lens may be mounted. The curved sprayer could then be oriented so that the ion spray generated by the curved sprayer is directed towards the aperture 32 and the orifice 36.

In addition, the position of the sprayer mount 12 may be adjusted with respect to the aperture 32 in the curtain plate 30 to improve the transmission of the generated ion spray(s) to a downstream device such as a mass spectrometer. This adjustment may comprise moving the sprayers 14, 16, 18 and 20 closer to the aperture 32, further away from the aperture 32, to the left of the aperture 32, to the right of the aperture 32, above the aperture 32, or below the aperture 32.

The sprayer mount 12 may have an electrically conductive base so that a power supply means may be used to apply the same potential to all the sprayers 14, 16, 18 and 20. Alternatively, there may be more than one sprayer mount in the multisprayer ion source 10. In the extreme, there may be a separate sprayer mount for each sprayer 14, 16, 18 and 20 which would be beneficial for utilizing a power supply means to apply different potentials to each sprayer 14, 16, 18 and 20 to individually adjust each ion spray generated therefrom. In this case, the power supply means may be separate power supplies for each sprayer 14, 16, 18 and 20 and ion lens 22, 24, 26 and 28. Alternatively, a variable resistance means such as a potentiometer may be employed by connecting different potentiometers in series with each sprayer 14, 16, 18 and 20 and then connecting each potentiometer/sprayer combination in parallel to one power source to facilitate the power supply means. The resistance of each potentiometer may then be adjusted to apply an appropriate potential to the associated sprayer. In a further alternative, one sprayer mount 12 that is nonconductive may be used and separate insulated wires may be attached to each sprayer 14, 16, 18 and 20 to apply the same potential thereto from one power supply. Alternatively, a nonconductive mount may be used with many power supplies to apply different potentials to the sprayers.

The preferred embodiment of the present invention provides ion lenses 22, 24, 26 and 28 mounted relative to each sprayer 14, 16, 18 and 20 respectively. Each ion lens 22, 24, 26 and 28 is electrically insulated from the sprayer 14, 16, 18 and 20 upon which it is mounted. Furthermore, a separate power supply may be connected to each ion lens 22, 24, 26 and 28 to apply a potential thereto or a single power supply and a means of independently varying the voltage to each ion lens 22, 24, 26 and 28 as previously described may be used.

The ion lenses 22, 24, 26 and 28 are adapted for the selective disabling of a sprayer that is generating an ion spray (i.e. the sprayer is operational) or the selective re-enabling of a previously disabled sprayer regardless of whether the sample solution flow through each sprayer 14, 16, 18 and 20 is continuous or discontinuous. More than one sprayer may be enabled or disabled at the same time. Disabling a sprayer 14, 16, 18 or 20 is achieved by increasing the potential, applied to the associated ion lens 22, 24, 26 and 28 to a magnitude great enough to inhibit the ion spray generated from the selected sprayer(s). Conversely, re-enabling a sprayer 14, 16, 18 or 20 that had been previously disabled, involves decreasing the potential applied to the associated ion lens 22, 24, 26 or 28 until an ion spray is once more generated.

The potential applied to the ion lenses 22, 24, 26 and 28 may be controlled in a manual or automatic fashion by electrical, mechanical or software means such as Labview™. The ability to use electric potential applied to one or more of the ion lenses 22, 24, 26 and 28 to selectively enable or disable certain sprayers in the multisprayer ion source 10 eliminates the need for expensive and complicated mechanical means for selecting between sprayers as described in the prior art.

Depending on the changes in the magnitude of the potentials applied to each ion lens 22, 24, 26 and 28, ion sprays may be sequentially generated from the sprayers 14, 16, 18 and 20. Alternatively, ion sprays may be simultaneously generated from the sprayers 14, 16, 18 or 20. The ion lenses 22, 24, 26 and 28 may further be used to increase the stability of each generated ion spray and the number of ions detected from each ion spray as disclosed by the inventors of the present invention in PCT application PCT/CA01/00728.

In use, typical potential differences on the order of 0 to 20,000 V may occur between one of the sprayers 14, 16, 18, and 20 and a counter-electrode (i.e. the curtain plate 30, the orifice plate 34 or the housing 38). Preferably the potential difference between one of the sprayers 14, 16, 18 and 20 and the associated ion lens 22, 24, 26 and 28 is approximately in the range of 0 to 20,000 V. However, it must be noted that the absolute magnitudes of the applied potentials are not important. Rather, it is the differences between various applied potentials that are important. For example, the sprayers 14, 16, 18 and 20 may be operated at a potential of 0 V while the curtain plate 30 and the orifice plate 34 are operated at a high negative potential and the ion lenses 22, 24, 26 and 28 are operated at separate potentials so that the ion sprays generated by each operational sprayer contain positive ions. If all applied potentials are reversed in polarity, then each operational sprayer may generate ion sprays containing negative ions, although typically, the magnitude of the potential difference between the sprayer 14, 16, 18 or 20 and the curtain plate 30 is different for negative ions.

Referring now to FIG. 2, shown therein is an embodiment of a dual sprayer apparatus 40 comprising two sprayers 42 and 44 and a sprayer mount 46 with a mounting hole 48. Each sprayer 42 and 44 comprises three concentric capillaries: an inner capillary, a middle capillary 52 and an outer capillary 54 mounted on a sprayer mounting means such as sprayer tee 56 having a nebulizer gas delivery means such as tubing 58 and a sample delivery means such as sample delivery capillary 60. In this embodiment, the sample delivery capillary 60 forms the inner capillary. The dual sprayer apparatus 40 further comprises an ion lens 62 mounted on sprayer 42 and an ion lens 64 mounted on sprayer 44. Each ion lens 62 and 64 also has a biasing means (i.e. an electrical biasing means to provide an electric potential) comprising mounting bracket 66 and a wire 68. The dual sprayer apparatus 40 also comprises a wire 70, a stud 72 and shielded wires 74. The dual sprayer apparatus 40 further comprises a slot 75 that may be used to convert the dual sprayer apparatus 40 into a four sprayer apparatus as described below.

The dual sprayer apparatus 40 may be mounted in a housing 38 (as shown in FIG. 1) with a curtain plate 30 having an aperture 32 and an orifice plate 34 having an orifice 36. Alternatively, it may be mounted in other types of ion source housings. The dual sprayer apparatus 40 is mounted by applying a fastening means (not shown), such as a nut, onto a receiving means, such as a stud mount (not shown) through the mounting hole 48 in the sprayer mount 46. Accordingly, the mounting hole 48 is positioned on the sprayer mount 46 such that the dual sprayer apparatus 40 may be installed on a commercial type of stud mount in commercial equipment such as a mass spectrometer or the like. Alternatively, for mass spectrometers that have an orifice plate with an orifice, the dual sprayer apparatus 40 may be placed in a housing 38 having only a curtain plate 30 with an aperture 32 and then bolted onto the mass spectrometer. This arrangement creates a region between the curtain plate 30 and the orifice plate of the mass spectrometer in which curtain gas may be placed. The housing 38 may also be adapted to be connectable with a mass spectrometer having an inlet capillary. In this case, the housing 38 does not require the orifice plate 34 or the curtain plate 30. Furthermore, the inlet capillary may be heated.

The sprayers 42 and 44 are oriented on the sprayer mount 46 such that the ion spray generated by each sprayer 42 and 44 is directed towards a downstream orifice or aperture. Accordingly, each sprayer 42 and 44 is mounted on the sprayer mount 46 using the sprayer tee 56, which is a turnable mount that may be rotated through 360 degrees to allow for the precise positioning of each sprayer 42 and 44. The sprayer tee 56 may be held in place with set screws or the like. The sprayer tee 56 is also adapted to provide a sample solution, via the sample delivery capillary 60, and nebulizer gas, via the tubing 58, to each sprayer 42 and 44. The sample solution is sent to the inner capillary and the nebulizer gas is sent to the annular region between the middle capillary 52 and the outer capillary 54. Alternatively, another mounting means may be used to fixedly mount each sprayer 42 and 44 to the sprayer mount 46.

In this embodiment, the inner capillary is preferably made from fused silica with an outer diameter of 150 µm and an inner diameter of 50 µm. The middle capillary 52 is preferably made from 21 gauge stainless steel syringe tubing and the outer capillary 54 is preferably made from 17 gauge stainless steel syringe tubing. Furthermore, the middle capillary 52 is adapted to extend past the outer capillary 54. It would be apparent to those skilled in the art that the dimensions of the inner capillary (not shown), the middle capillary 52 and the outer capillary 54 may be increased or decreased as well as the length of the protrusion of the middle capillary 52 and the exact positioning of the inner capillary 50 without deviating from the general spirit of this invention. It would also be apparent to those skilled in the art that a heated gas, or other heating element or elements may be positioned in the housing 38 to aid in desolvation. For reduced flow rate or nanospray ion sources, the concentric capillaries may be replaced with tapered capillary tips. The tips of the capillaries may be pulled to a fine taper and made as uniform as possible in shape.

The sample delivery capillary 60 may be coupled with syringe pumps, chromatography systems, capillary electrophoresis systems, microfluidic devices or other sample delivery or separation systems to provide a sample solution to the sprayer 42 or 44 to which it is attached. Furthermore, the sample delivery capillary 60 may be coupled with the sprayer 42 or 44 by any means known to those skilled in the art. This may include, but is not limited to, a low dead volume conductive fastener, a liquid junction (Zhang et al., *Anal. Chem.*, 2000, 72, pp. 1015-1022.), or a microdialysis junction (Severs et al., *Anal. Chem.*, 1997, 69, pp. 2154-2158).

The ion lenses 62 and 64 and their positions relative to the sprayers 42 and 44 will now be discussed by making reference only to the ion lens 62 and the sprayer 42 for simplicity. Referring now to FIG. 3a, shown therein is the ion lens 62 having an aperture 76 that is non-adjustable. The ion lens 62 may preferably have a length of 19 mm and a height of 8 mm. The aperture 76 may preferably have a length of 10 mm and a height of 5 mm for reduced flow rate applications. Alternatively, the aperture 76 may have a length ranging from approximately 2 mm up to approximately 17 mm and a height ranging from 2 mm up to approximately 17 mm. The ion lens 62 has a thickness of 1 mm. In general, the smallest size for the ion lens 62 is dictated by the onset of arcing to the sprayer 42 and the largest size for the ion lens 62 is dictated by spatial limitations and decrease in effectiveness.

The ion lens 62 is preferably constructed from inert, conductive materials such as stainless steel. Furthermore, the ion lens 62 may have a solid or hollow cross section and may be continuous or discontinuous in its circumference (i.e. the ion lens 62 may not be a complete ring). In the latter case, the discontinuity in the circumference of ion lens 62 is preferably small such that the ion lens 62 substantially surrounds the tip of the sprayer 42. The ion lens 62 may further have a cross-section in the shape of a circle, an oval, a square, a rectangle, a triangle or any other regular or irregular polygonal shape or other two-dimensional shape.

Figure 3B:
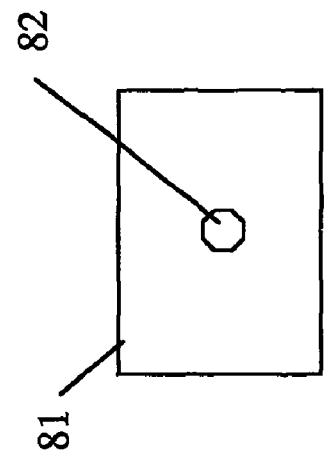
FIG. 3b is a front view of an ion lens having a variable aperture.

Referring now to FIG. 3b, an alternative embodiment is shown in which an ion lens 62' has a variable aperture 76' in the horizontal direction due to a slotted window piece 78. To increase (decrease) the size of the variable aperture 76', the slotted window piece 78 is moved to the right (left). The size of the variable aperture 76' of the ion lens 62' is adjustable so that the ion spray generated by the sprayer 42 is improved. In this embodiment, the vertical dimension of the ion lens 62' is non-adjustable, however, a vertical adjustment could be built into the ion lens 62' in an alternate embodiment.

Figure 3D:
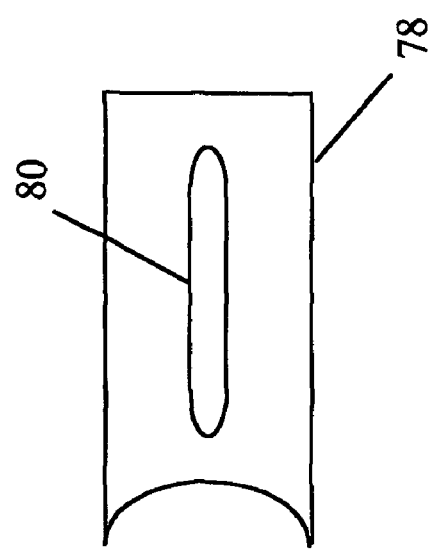
FIG. 3d is a front view of the cover piece used in the variable aperture ion lens.
Figure 3A:
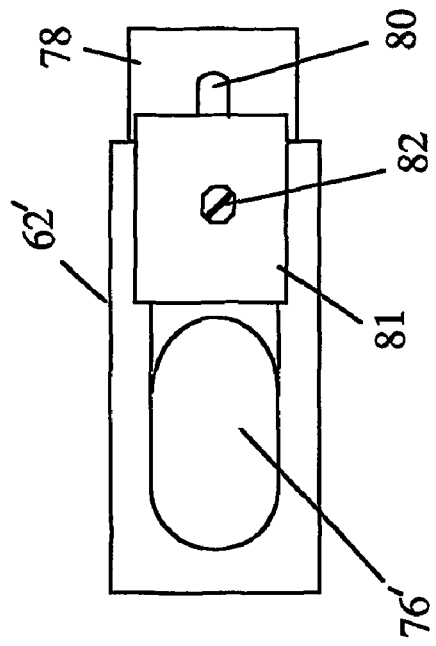
FIG. 3a is a front view of an ion lens.
Figure 3C:
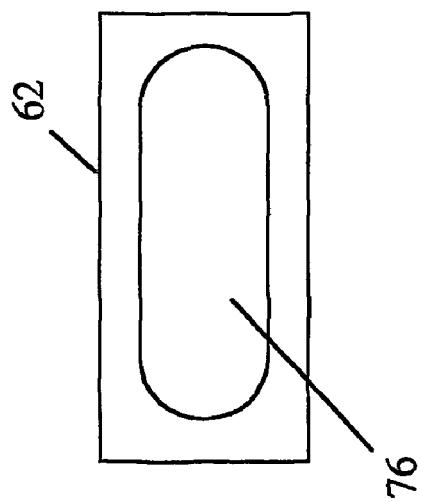
FIG. 3c is a front view of the slotted window piece used in the variable aperture ion lens.

The slotted window piece 78 is shown in more detail in FIG. 3c. The slotted window piece 78 has a groove 80 which is used to permit horizontal movement of the slotted window piece 78 in a groove (not shown) in the ion lens 62' to change the size of the aperture 76'. The length of the aperture 76' may be adjustable from a length of 7 mm to a length of about 14 mm although a length of approximately 9 mm may be preferable. A cover piece 81, shown in FIG. 3d, is placed over the slotted window piece 78 and a screw, placed through aperture 82, holds the cover piece 81 and the slotted window piece 78 in place on the ion lens 62'.

Figure 4C:
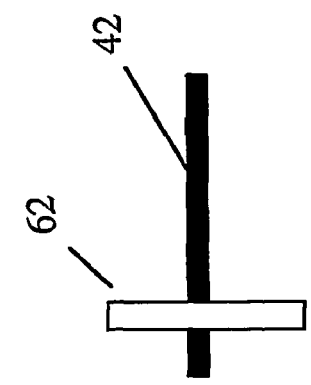
FIG. 4c is a side view showing an orientation of a sprayer within an ion lens.
Figure 4B:
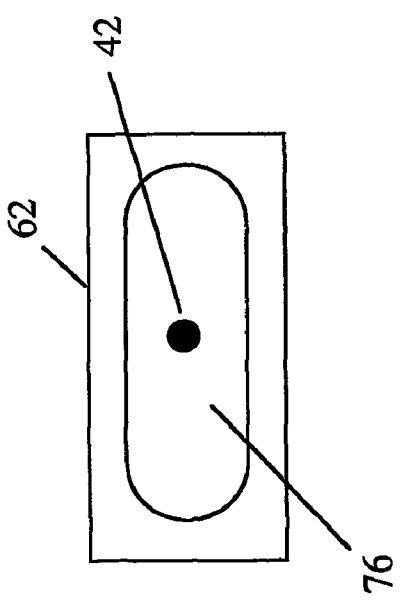
FIG. 4b is a front view showing another orientation of a sprayer within an ion lens.
Figure 4E:
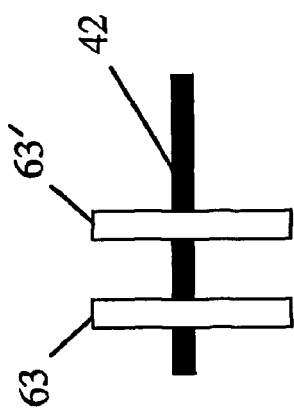
FIG. 4e is a partial side view of a sprayer of a further alternative embodiment of the multisprayer ion source wherein more than one ion lens is oriented along the longitudinal axis of a sprayer.
Figure 4A:
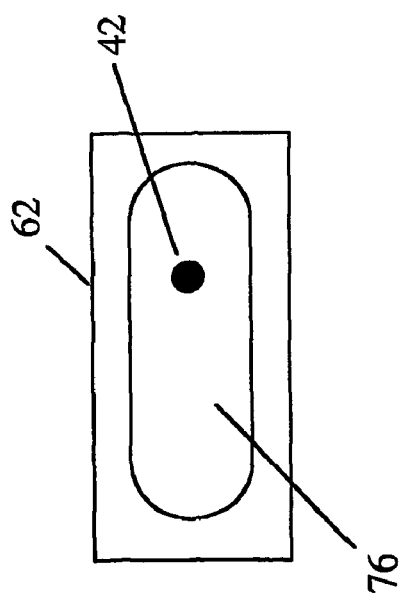
FIG. 4a is a front view showing one orientation of a sprayer within an ion lens.

Referring now to FIGS. 4a to 4c, the ion lens 62 is positioned in circumferential proximity to the surface of the sprayer 42 and in axial proximity to the tip of the sprayer 42. FIG. 4a shows that the sprayer 42 may be vertically centered in the ion lens 62 and horizontally offset. FIG. 4b shows an alternative embodiment in which the sprayer 42 is horizontally and vertically centered within the ion lens 62. Alternatively, the sprayer 42 may be asymmetrically placed, both horizontally and vertically, within the ion lens 62.

Referring now to FIG. 4c, the plane defined by the ion lens 62 is positioned substantially perpendicular to the longitudinal axis of the sprayer 42. However, the ion lens 62 does not need to be exactly perpendicular to the longitudinal axis of the sprayer 42 and may be slightly angled with respect to the longitudinal axis of the sprayer 42. The tip of the sprayer 42 intersects the plane of the ion lens 62. The position of the ion lens 62 is adjustable along the longitudinal axis of the sprayer 42. However, the position of the ion lens 62 along the longitudinal axis of the sprayer 42 is preferably adjusted to improve the transmission of ions within the generated ion spray into a downstream device such as a mass spectrometer. As disclosed by the inventors in PCT application PCT/CA01/00728, the ion lens 62 may be placed 0.1 to 5 mm behind the tip of the middle capillary 52 of the sprayer 42. More preferably, the ion lens 62 may be placed approximately 1 to 3 mm behind the tip of the middle capillary 50 of the sprayer 62. Most preferably, the ion lens 62 may be placed approximately 2 mm behind the tip of the middle capillary 50 of the sprayer 42. Further improvement in the generated ion spray would involve adjusting the position of each sprayer 42 and 44 and adjusting the potentials applied to the various components of the dual sprayer apparatus 40 during use.

Figure 4D:
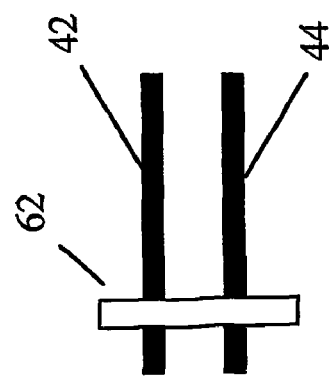
FIG. 4d is a partial side view of a sprayer of an alternative embodiment of the multisprayer ion source wherein an ion lens surrounds more than one sprayer.

FIG. 4d shows a partial side view of an alternate embodiment of the multisprayer ion source 10 in which the ion lens 62 surrounds more than one sprayer 42 and 44. This alternate embodiment may be preferable in systems where the same analyte is provided to more than one sprayer to increase the throughput or the sensitivity of a downstream mass analysis system. The remainder of the multisprayer ion source 10 would need to be designed to move the sprayers 42 and 44 close enough to each other such that one ion lens 62 could surround both sprayers 42 and 44. Alternatively, ion lens 62 could be enlarged to surround both sprayers 42 and 44. Furthermore, although FIG. 4d shows two sprayers in one ion lens, there may be alternative embodiments where there are more than two sprayers surrounded by one ion lens. In this case, there would likely be several ion lenses with each ion lens surrounding a plurality of sprayers. In this case, the same analyte, mass calibrant or internal standard may be provided to each sprayer that is surrounded by a given ion lens. This embodiment is particularly suited to increasing the amount of ions generated for a given analyte, mass calibrant or internal standard.

There may also be further alternative embodiments of the multisprayer ion source 10 in which there is more than one ion lens mounted on a sprayer. Referring to FIG. 4e, ion lenses 63 and 63' are mounted on the same sprayer 42 and are spaced along the longitudinal axis of the sprayer 42. In this case, the potential applied to the ion lens 63 mounted closest to the tip of the sprayer 42 may be used to enable or disable the sprayer 42 and the other ion lens 63' may be used to optimize the generation of the ions from the sprayer 42 when the sprayer 42 is operational.

Referring again to FIG. 2, two external power supplies (not shown) are used to apply potentials to the ion lenses 62 and 64 via the wires 68 which are attached to the mounting brackets 66. The mounting brackets 66 are shielded and conductive. Alternatively, other types of bracketry or mounting arrangements could be used to mount each ion lens 62 and 64 proximal to the appropriate sprayer 42 and 44. The potential applied to the ion lenses 62 and 64 may be adjusted depending on the sample solution carried in the sprayers 42 and 44, the sample solution flow rate, the mass to charge ratio of the ions generated from each sample, the potential applied to the sprayers 42 and 44, the curtain plate potential, the proximity of the sprayers 42 and 44 to each other and to the curtain plate 30, the position of the ion lens 62 or 64 relative to the tip of the associated sprayer 42 or 44, the charge of the generated ions, or sample solvent properties such as surface tension.

Figure 5:
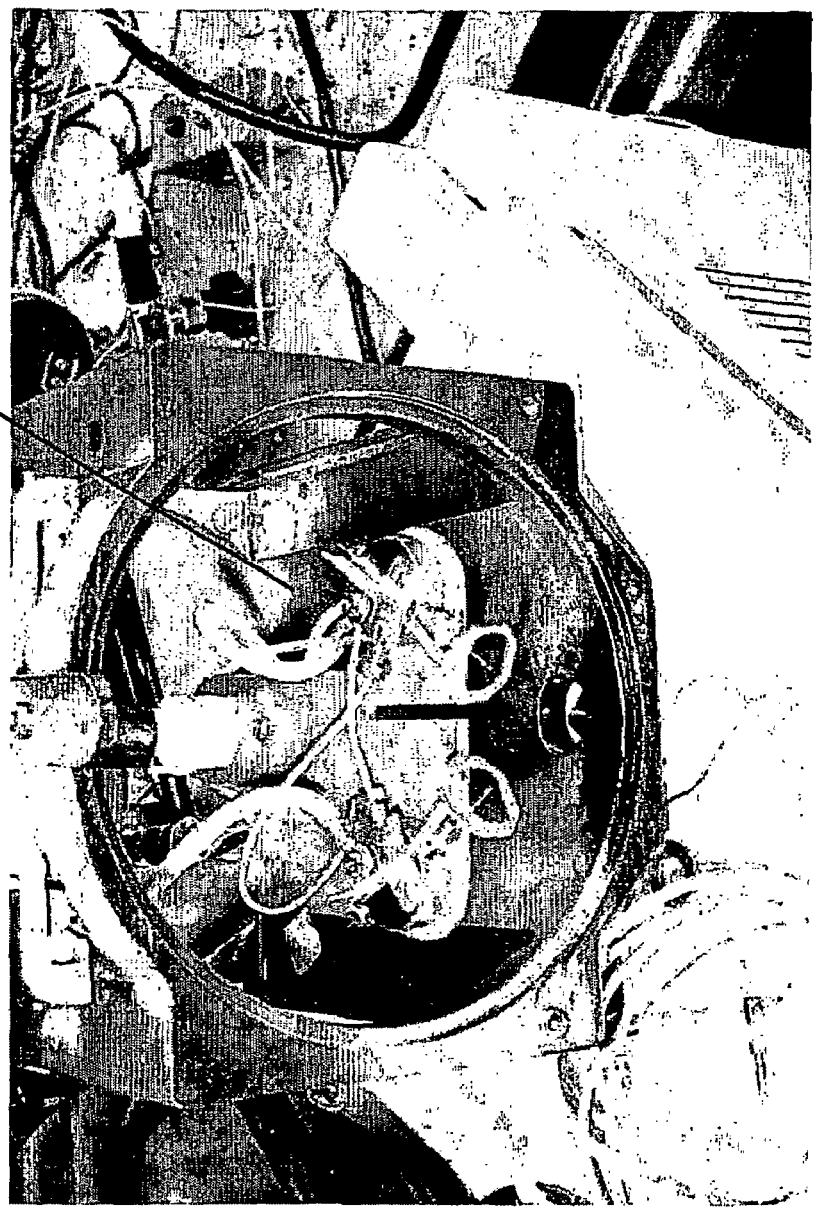
FIG. 5 is a photograph of a dual sprayer ion source prototype.

In this embodiment, the sprayer mount 46 is made from electrically insulating material such as plexiglass, polyvinyl chloride or the like. The potential to be applied to the sprayers 42 and 44 from a power supply is provided via the wire 70 which is fastened to the stud 72. Shielded wires 74 are also fastened to the stud 72, which is conductive, to convey the potential to each sprayer tee 56. Thus, the same potential is applied to the sprayers 42 and 44. Alternatively, the sprayer mount 46 may be made of a conductive material such as aluminum or the like to eliminate the need for the shielded wires 74. The applied potential is therefore directly applied to the sprayer mount 46 by fastening wire 70 to the stud 72 which is also in direct electrical contact with each of the sprayer tees 56. This ensures that each sprayer 42 and 44 is biased at the same potential and that separate power supplies are not needed for each sprayer 42 and 44. However, the use of a conductive mount may lead to increased occurrence of arcing. An example of a dual sprayer ion source 84 based on the embodiment just discussed (using a non-conductive sprayer mount) is shown in FIG. 5.

Figure 6:
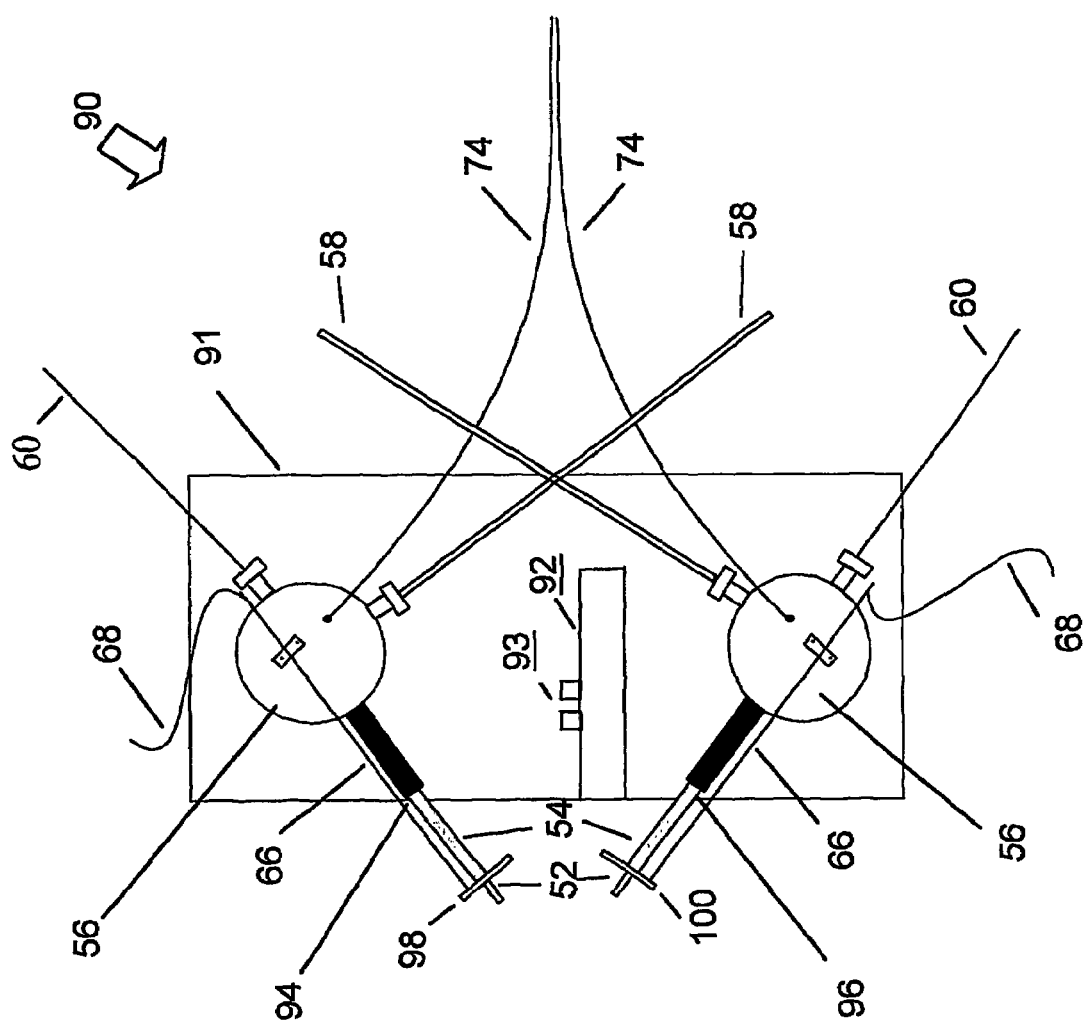
FIG. 6 is a top view of an attachment piece having two extra sprayers.
Figure 7:
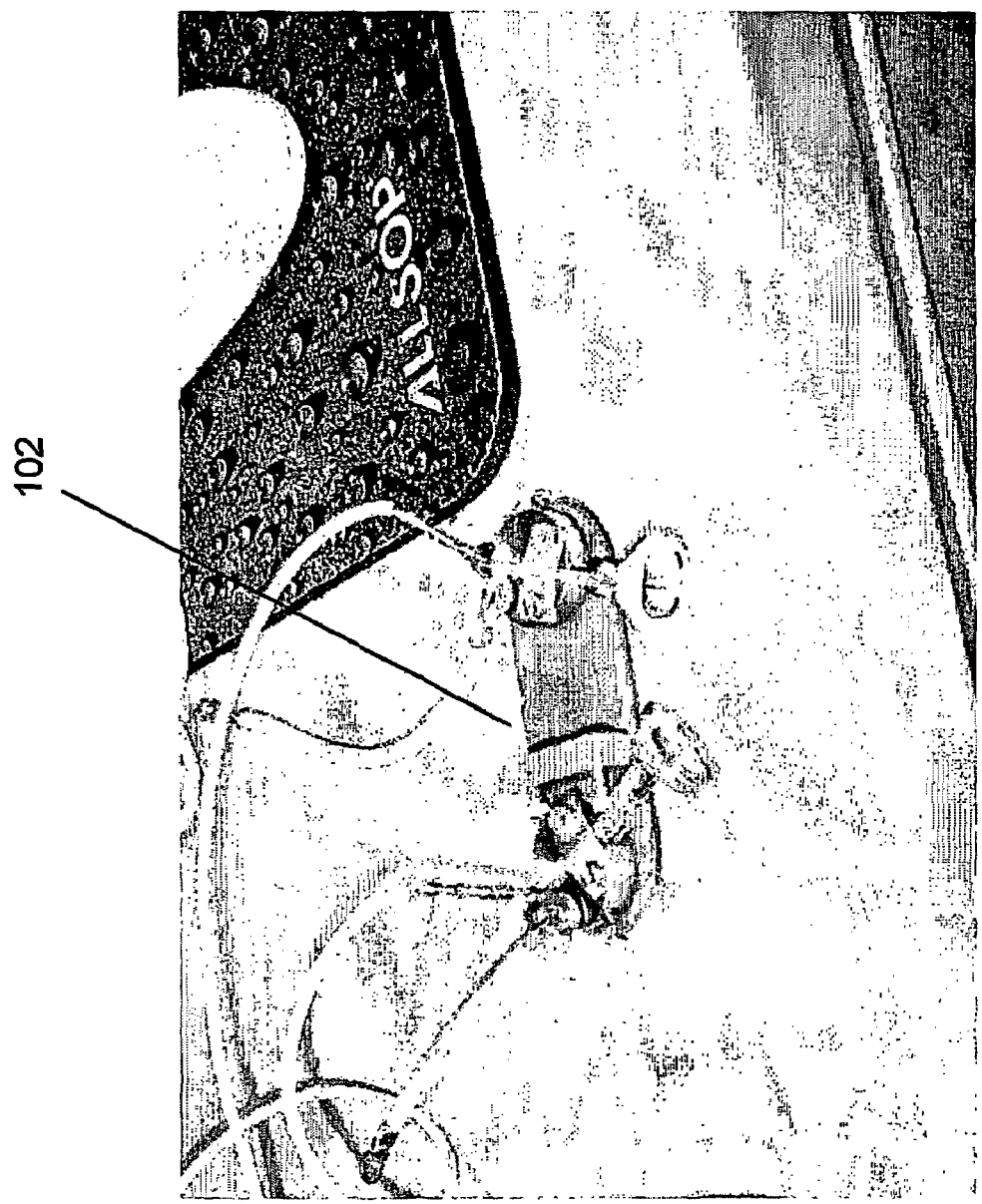
FIG. 7 is a photograph of an attachment piece prototype with two extra sprayers.

In an alternative embodiment, the dual sprayer apparatus 40 may be converted into a four sprayer apparatus by combining the dual sprayer apparatus 40 with an attachment piece 90 as shown in FIG. 6. The attachment piece 90 comprises a plate 91 and retaining means comprising a ridge 92 and fastening means 93. Fastening means 93 may be screws or the like. The rest of the components for the attachment piece 90, as well as the means to apply potentials, are similar to those shown for the dual sprayer apparatus 40 and have therefore been identified using similar reference numerals and will not be discussed. However, the sprayers 94 and 96 and the ion lenses 98 and 100 have been given unique reference numerals for the sake of clarity in the description below. An example of an attachment piece prototype 102 is shown in FIG. 7 in which the plate 91 is non-conductive.

Figure 8:
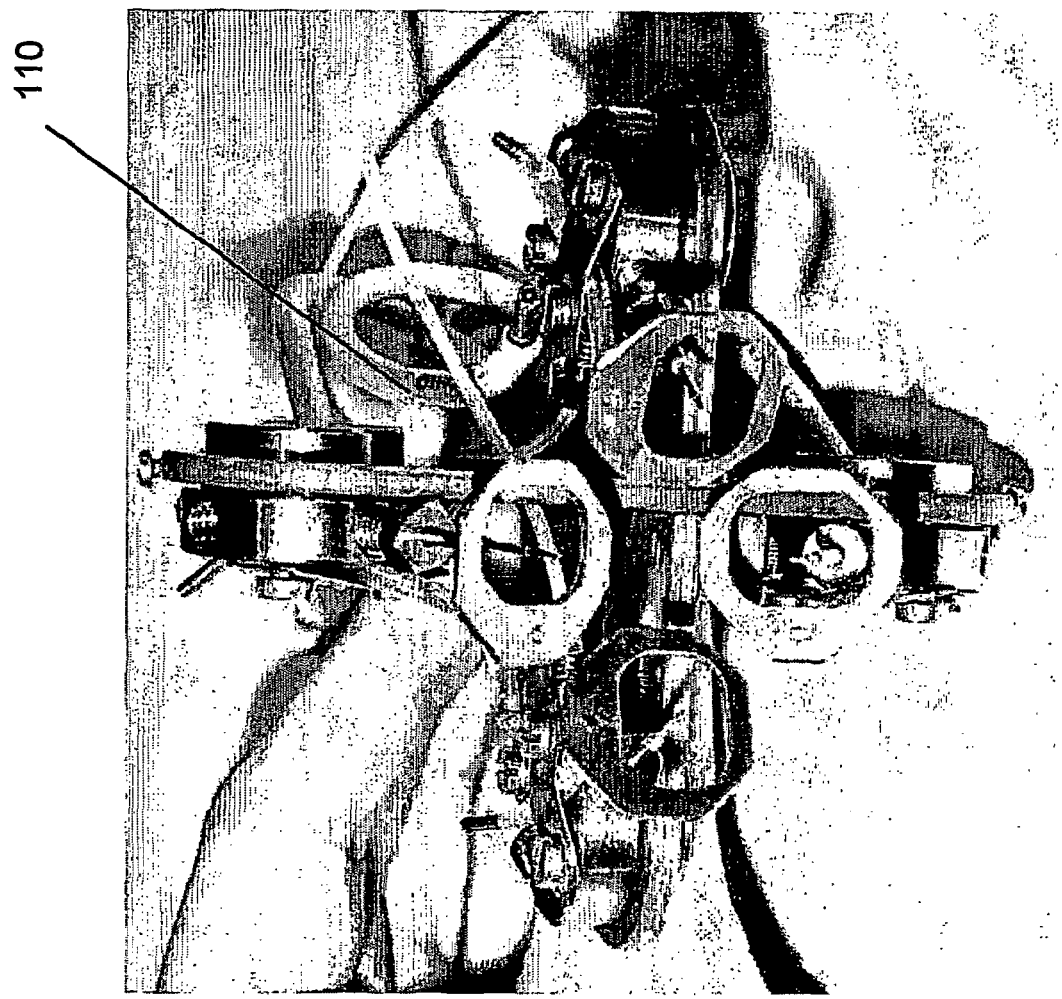
FIG. 8 is a photograph of a four sprayer prototype.

The attachment piece 90 is attached to the dual sprayer apparatus 40 by sliding the plate 91 into the slot 75 of the sprayer mount 46 such that the bottom of the ridge 92 (i.e. the side of the ridge 92 opposite the fastening means 93) sits on the sprayer mount 46. The fastening means 93 are then fastened to mounting apertures in the sprayer mount 46. These mounting apertures are not shown in FIG. 2, however, these mounting apertures are visible on the dual sprayer ion source 84 shown in FIG. 5. An example of a four sprayer apparatus 110 resulting from the combination of the attachment piece prototype 102 and a prototype of the dual sprayer apparatus is shown in FIG. 8. In this case, the tips of the sprayers are arranged symmetrically and a single power supply is used to apply the same potential to each sprayer. However, each ion lens may be attached to a separate power supply.

In use, the four sprayer apparatus 110 is installed in an ion source housing such as housing 38 shown in FIG. 1. A sample solution (or a solution containing a mass calibrant or a solution containing an internal standard) travels via the sample delivery capillary 60 to the sprayer tee 56 of each sprayer 42, 44, 94 and 96. A nebulizer gas is then sent to the stainless steel tee 56 of each sprayer via the tubing 58 of each sprayer at which point the nebulizer gas flows coaxially in the annular space between the middle capillary 52 and the outer capillary 54. The nebulizer gas consists of compressed air, but may be replaced with nitrogen, oxygen, sulphur hexafluoride, or other gases. In particular, nebulizer gases such as oxygen and sulphur hexafluoride may be useful as electron scavenging gases when operating in negative ion mode. The sample solution and the nebulizer gas travel to the tip of each sprayer 42, 44, 94 and 96. The nebulizer gas assists in breaking up charged droplets at the tip of each sprayer 42, 44, 94 and 96. The nebulizer gas also allows for much higher sample solution flow rates to be used and may help to evaporate the solvent in the sample solution. The nebulizer gas may also help to disperse samples with high surface tension, such as water.

Potentials are then applied to the sprayers 42, 44, 94 and 96 and the counter-electrodes in the housing 38 (i.e. the curtain plate 30 and the orifice plate 34) such that an ion spray is generated at each sprayer that is to be operational. A potential is then preferably applied to the ion lens 62, 64, 98 or 100 that corresponds to an operational sprayer to improve the ion signal magnitude and stability detected by a downstream mass spectrometer. Alternatively, each ion lens 62, 64, 98 or 100 may be kept at ground or floating. In either of these cases an "enabling potential" is applied to the ion lens 62, 64, 98 or 100 such that the sprayers that are to be operational remain operational. The enabling potential is therefore defined as a potential which allows a sprayer 42, 44, 94 or 96 to remain operational and may be chosen from a range of appropriate potentials. As mentioned previously, the enabling potential may also be adjusted to improve the ion spray generated by an operational sprayer and to increase the resulting ion signal that may be measured by a downstream mass analyzer. When the ion spray generated by an operational sprayer must be turned off (i.e. the sprayer must be disabled), the potential applied to the ion lens mounted on that sprayer is increased until the ion spray is no longer being generated. In this case, a "disabling potential" is applied to the ion lens 62, 64, 98 or 100 such that operational or enabled sprayers which are to be turned off are then disabled. The disabling potential is therefore chosen from a range of potentials which allow a sprayer 42, 44, 94 or 96 to be disabled. To re-enable a disabled sprayer, the potential applied to the ion lens mounted on that sprayer is decreased until the ion spray is generated once more (i.e. an enabling potential is applied to the ion lens).

In use, one may generate an ion spray from one sprayer, then disable the sprayer and generate an ion spray from another sprayer and so on and so forth. In this fashion, sequential analysis of the sample solutions supplied to each sprayer 42, 44, 94 and 96 may be performed. Alternatively, any other combination of enabling and disabling each sprayer and/or groups of sprayers may be carried out by changing the potential applied to the ion lenses mounted on these sprayers. For instance, for higher sample throughput, all four of the sprayers may be enabled simultaneously presuming that all samples produce ions that have substantially different mass to charge ratios.

In use, typical potentials which may be applied to the sprayers 42, 44, 94 and 96 may range from 4000 to 8500 V. Typical enabling potentials applied to the ion lenses 62, 64, 98 and 100 may range from 0 to 5000 V to optimize the ion spray generated by an operational sprayer and allow an operational sprayer to remain enabled. Typical disabling potentials applied to the ion lenses 62, 64, 98 and 100 may range from 5000 V and above. The disabling potential typically depends on the potential applied to the sprayer which is to be disabled. Furthermore, a potential of 400 to 2000 V may be applied to the curtain plate 30 and the housing may be kept at ground potential. The potential applied to the orifice plate 34 may vary from 0 to 400 V. It is important to note that these potentials are given as examples only and are in no way meant to limit the scope or spirit of this invention.

Furthermore, in use, one may supply a variety of substances to the sprayers 42, 44, 94 and 96 such as various analyte samples, mass calibrants and internal standards to effect a variety of analysis protocols. For instance, different analyte samples may be provided to each sprayer 42, 44, 94 and 96 for higher throughput analysis of the various analyte samples. Alternatively, the same analyte sample may be provided to two or more sprayers 42, 44, 94 and 96 to increase the number of generated analyte ions. In fact, results obtained with the dual sprayer prototype 84 are similar to those obtained by Tang et al. with regards to obtaining increased ion signals when using an increased number of sprayers (Tang et al., *Anal. Chem.,* 2001, 73, pp. 1658-1663). Alternatively, an analyte sample may be provided to one sprayer 42, 44, 94 or 96 and at least one mass calibrant may be provided to the other sprayers. Each sprayer may then be operated simultaneously to generate analyte ions and mass calibrant ions which may then be provided to a downstream mass spectrometer so that the mass calibrant ions are used to calibrate the mass analyzer. Alternatively, an analyte sample may be provided to one sprayer 42, 44, 94 or 96 and at least one internal standard may be provided to other sprayers. Each sprayer may then be operated simultaneously to generate analyte ions and internal standard ions which may then be provided to a downstream mass spectrometer whereby the internal standard ions are used to assess ion source efficiency and aid in analyte ion quantification. For each of these cases, the sample solution flow rates may be variable, ranging from a few nL/min up to approximately 1 µL/min for nanospray and reduced flow-rate applications, respectively, and 1 µL/min up to approximately 2 mL/min for ion spray, and heated nebulizer ion spray sources.

A number of experiments were conducted on a single sprayer ion source employing an ion lens, the dual sprayer ion source 84, and an ion source employing the four sprayer apparatus 110. In each case, a quadrupole mass spectrometer was used to detect the ions generated by the various ion sources. In these experiments, the sample solutions contained either cyctochrome c, reserpine or bradykinin. The cytochrome c sample solution comprised 10 µM cytochrome c in a solution of 10%/90% v/v methanol/water. The bradykinin sample solution comprised $10^{-4}$ M bradykinin in a solution of 39.5% methanol, 1% acetic acid, and 59.5% water. The reserpine solution comprised $10^{-5}$ M reserpine in a solution of 10% water and 90% acetonitrile.

Figure 9:
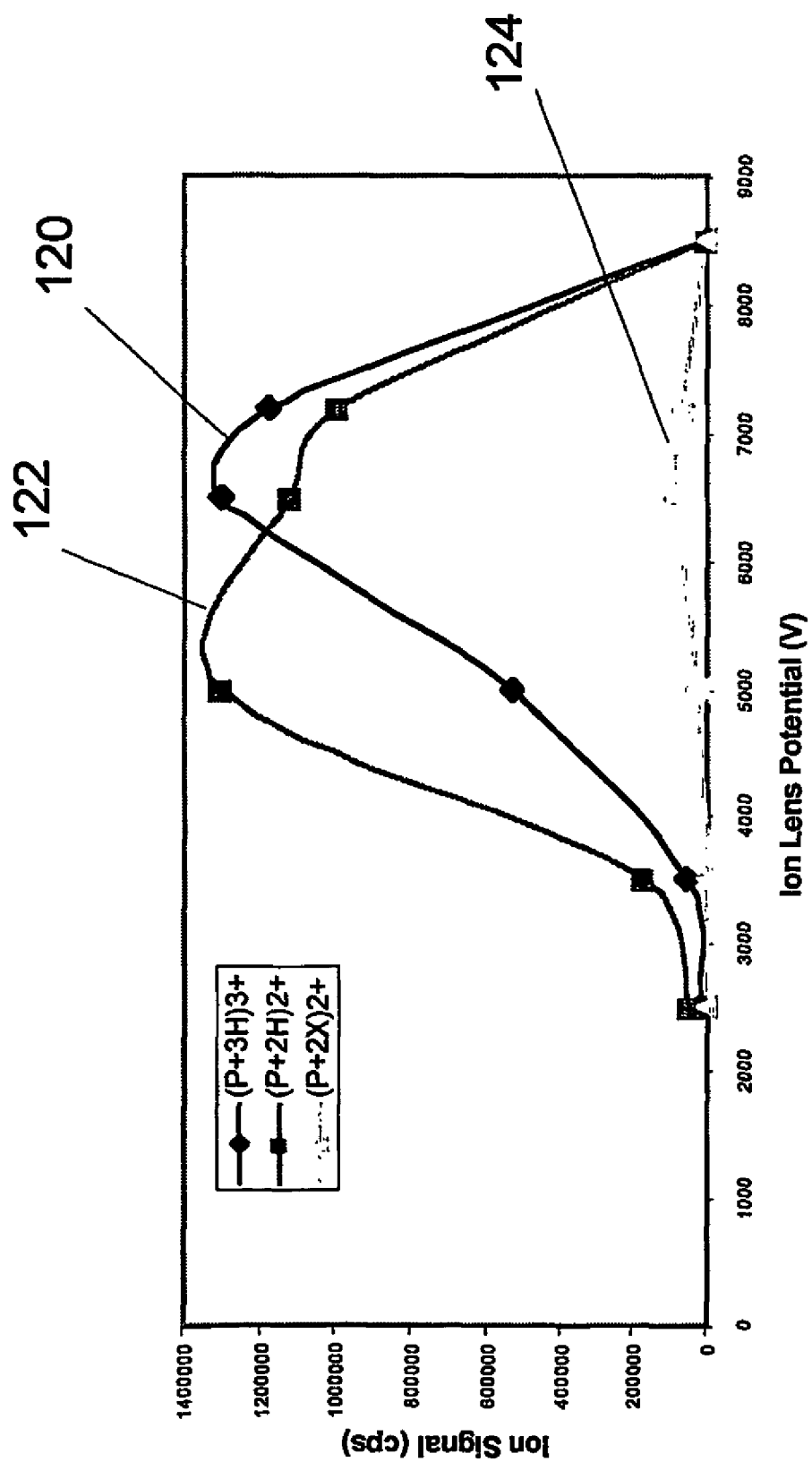
FIG. 9 is a graph of ion signal magnitude versus the potential applied to an ion lens for a single sprayer ion source having an ion lens mounted proximate to the sprayer tip.

Referring now to FIG. 9, the illustrated experimental results were obtained from a single sprayer ion source having an ion lens mounted in close proximity to the sprayer. The results indicate that the ion spray from the single sprayer can be enabled or disabled depending on the potential applied to the ions lens. In this experiment, the sample solution contained bradykinin. The potentials applied to the sprayer, curtain plate and orifice plate were 7600 V, 1850 V and 180 V respectively. The potential applied to the ion lens ranged from 2500 V to 8500 V. The generated ion spray contained doubly and triply protonated bradykinin peptide ions. The maximum ion signal obtained for the triply protonated bradykinin peptide ions occurred with a potential of 6500 V applied to the ion lens. This can be seen in curve 120. Further increases in the potential applied to the ion lens terminates the generated ion spray (i.e. the sprayer becomes disabled). However, if the potential applied to the ion lens is then decreased, the ion signal is re-generated (i.e. the sprayer is re-enabled). Similar results are seen for doubly protonated bradykinin ions as shown in curves 122 and 124.

This experiment was also conducted using one sprayer in the dual sprayer ion source 84 and one sprayer in the four sprayer apparatus 110. In both cases, the potential applied to the sprayers was typically close to 5200 V and the enabling potential applied to the ion lens mounted on the operational sprayer was typically 1000-2500 V to optimize the generated ion spray. No potential was applied to the other ion lenses. Increasing the potential applied to the ion lens, mounted on the operational sprayer, above 4000 V destabilized the generated ion spray and a further increase in applied potential to 5000 V disabled the sprayer. Accordingly, for single and multisprayer ion sources having ion lenses mounted proximal to each sprayer, the potential applied to the ion lens required to disable a sprayer is close in value to the potential applied to the sprayer.

In another experiment, the magnitude of the ion signal generated by a single sprayer ion source without an ion lens mounted proximal to the sprayer was compared to the magnitude of the ion signal generated from one sprayer of the four sprayer apparatus 110 for a sample of bradykinin. This experiment was conducted since it was not obvious whether a single sprayer of a multisprayer ion source could generate an ion spray having a magnitude comparable to that which could be generated by a single sprayer ion source with no ion lens. In fact, it has been shown that when one sprayer of a commercial multisprayer ion source is used there is a decrease in ion signal magnitude (Yang et al., *Anal. Chem.,* 2001, 73, pp. 1740-1747) compared to the magnitude of the ion signal generated by a commercial single sprayer ion source under similar experimental conditions (there were no ion lenses mounted on the sprayers in the commercial multisprayer or the single sprayer ion sources). Accordingly, in cases where high-throughput analysis is not required, investigators may find it necessary to use a single sprayer ion source instead of one sprayer of the commercial multisprayer ion source in order to avoid a loss of ion signal.

The results of this experiment are shown in Table 1 for doubly protonated bradykinin. The magnitude of the ion signal was measured during 10 scans of the quadrupole mass spectrometer. The results indicate that the ion signal magnitude is comparable with both ion sources. Accordingly, one sprayer of a multisprayer ion source in which each sprayer has an ion lens mounted proximally thereto may be used in place of a single sprayer ion source, and produce comparable sensitivity. For the single sprayer ion source, 5200 V and 1000 V were applied to the sprayer and the curtain plate respectively. For the four sprayer ion source, 5500 V was applied to each sprayer, 1000 V was applied to the ion lens mounted on the sprayer that was generating the ion spray, no voltage was applied to the other ion lenses and 1000 V was applied to the curtain plate. The sprayers that had ion lenses with no applied potential were not provided with a sample solution and therefore did not generate an ion spray.

TABLE 1

Ion Magnitude (counts per second) measured from various ion sources

| Ion source | Ion Signal Magnitude (cps) |
| --- | --- |
| Single sprayer ion source | $1.11 \times 10^6$ |
| Single sprayer from four sprayer ion source | $1.12 \times 10^6$ |

Figure 10:
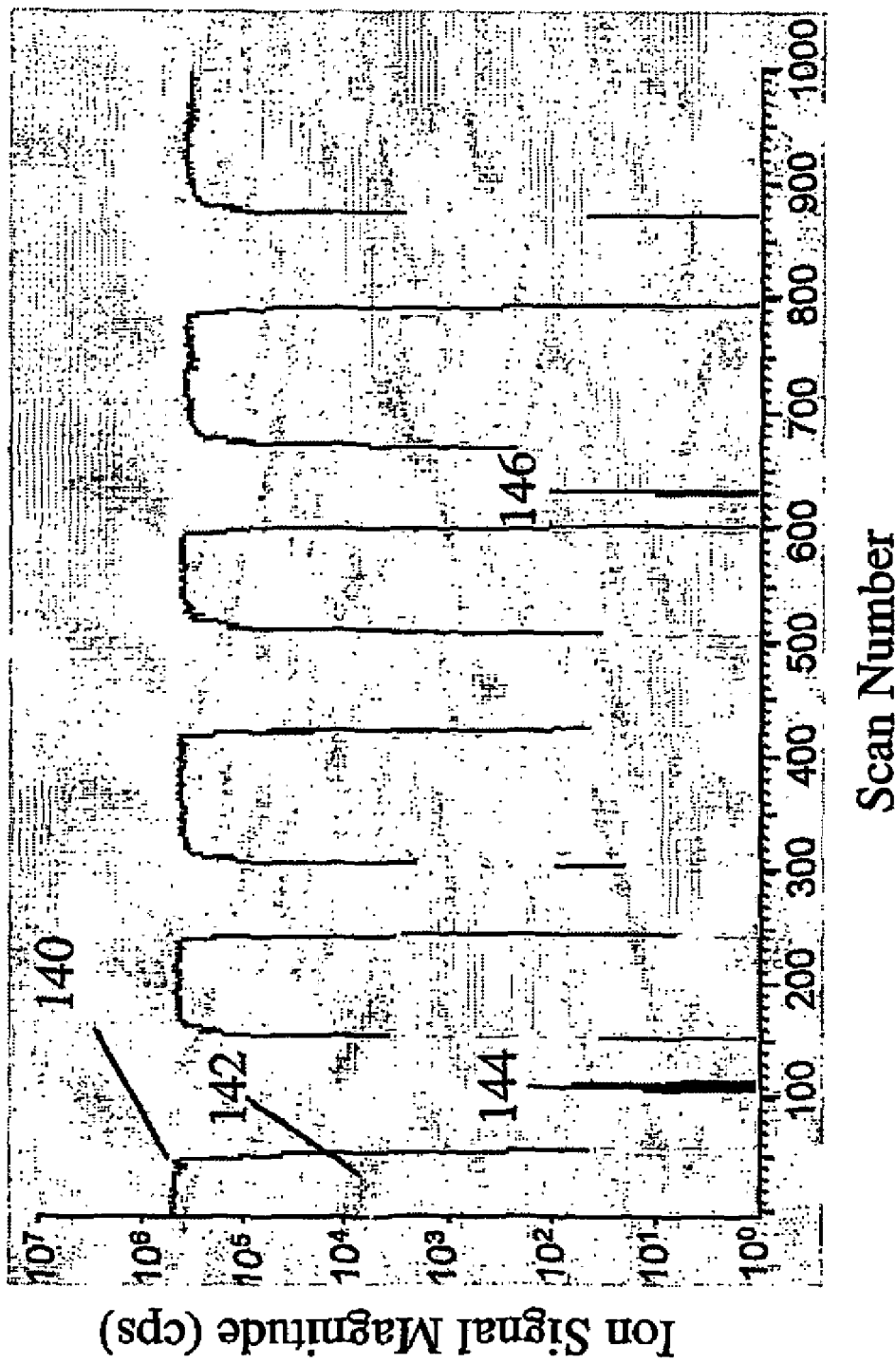
FIG. 10 is a graph of ion signal magnitude versus scan number as the potential applied to an ion lens mounted on an operational sprayer in a dual sprayer ion source is varied.

Referring now to FIG. 10, an experiment was conducted to determine the change in ion signal magnitude as the potential applied to the ion lens mounted on a sprayer generating an ion spray is quickly cycled between an enabling potential and a disabling potential. A dual sprayer ion source was used. FIG. 10 shows the measured ion intensity vs scan number. Each of the scans required 50 ms. The experiment demonstrated the ion spray generated by one of the sprayers in a multisprayer ion source can be reproducibly enabled or disabled by applying an appropriate potential to the ion lens mounted on the operational sprayer. The sample solution contained bradykinin. Potentials of 1961 V and 6000 V were applied to the curtain plate and the operational sprayer respectively. The potential applied to the ion lens mounted on the operational sprayer was initially at 600 V (i.e. the enabling potential) and cycled to 8000 V (i.e. the disabling potential). Curve 140 (i.e. the curve with the higher amplitude) shows the ion signal magnitude from the ion spray for doubly protonated bradykinin and curve 142 (i.e. the curve with the lower amplitude) shows the ion signal magnitude from the ion spray for triply protonated bradykinin. A downward movement on each curve 140 and 142 indicates that the potential applied to the ion lens was increased to the disabling voltage and an upward movement on each curve indicates that the potential applied to the ion lens was decreased to the enabling potential. The curves 140 and 142 show that the ion signal restabilizes within approximately 200 ms as the applied potential on the ion lens is decreased to the enabling voltage. Furthermore, when a disabling voltage of 7500 V was used, there were minor noise spikes 144 and 146. However, increasing the disabling voltage to 8000 V, was effective in removing these noise spikes.

In this experiment, the potential applied to the ion lens mounted on the operational sprayer was controlled manually. Hence, approximately 1 second was required to increase the potential applied to the ion lens on the operational sprayer from the enabling potential to the disabling potential or to decrease the applied potential from the disabling potential to the enabling potential. Alternatively, the applied potential may be manipulated using software means (i.e. Labview™) and data acquisition/control means (i.e. an A/D card and a D/A card) to reduce the time required to change the potential applied to the ion lens. It will be apparent to those skilled in the art that there are many different means to rapidly and reproducibly switch this potential. It should be mentioned that even though the applied potential was manually controlled, the ion spray could be eliminated within 0.2 to 0.5 seconds of increasing of the potential applied to the ion lens with this embodiment. This is approximately 5 times faster than using the potential applied to the sprayer to terminate the ion spray. Alternatively, a high speed switch may be used, as described further below, to rapidly vary the potential applied to the ion lens. The use of a high speed switching device should decrease the length of time required to enable/disable a sprayer dramatically.

Figure 11:
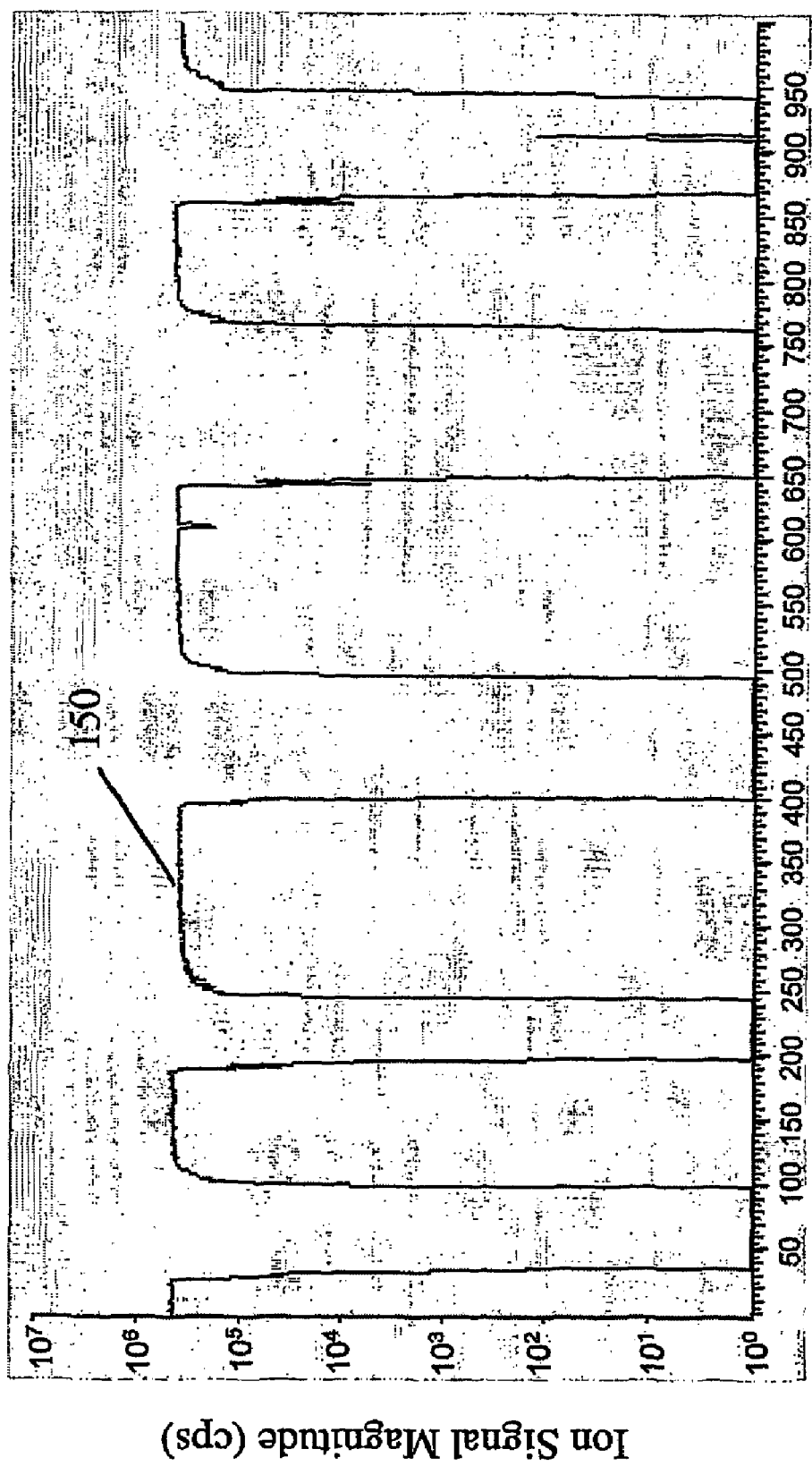
FIG. 11 is a graph of ion signal magnitude versus scan number as the potential applied to an ion lens mounted on an operational sprayer in a dual sprayer ion source is varied while a high disabling potential is applied to the ion lens mounted on the disabled sprayer.

Referring now to FIG. 11, another experiment was conducted using the dual sprayer ion source 84 in which the potential applied to the ion lens mounted on one sprayer was cycled between enabling and disabling potentials, as described above, and the potential applied to the ion lens mounted on the other sprayer was maintained at a disabling potential. In the experiment, the sample solution contained bradykinin. Potentials of 1961 V and 6000 V were applied to the curtain plate and the operational sprayer respectively. An enabling potential of 600 V and a disabling potential of 8000 V was alternately applied to the ion lens mounted on the operational sprayer. A disabling potential of 8000 V was applied to the ion lens mounted on the other sprayer. The experiment shows that the ion spray generated by the operational sprayer (i.e. curve 150) could be selectively enabled and disabled in a reproducible manner even though a large disabling potential was applied to the ion lens mounted on the other sprayer.

Figure 12:
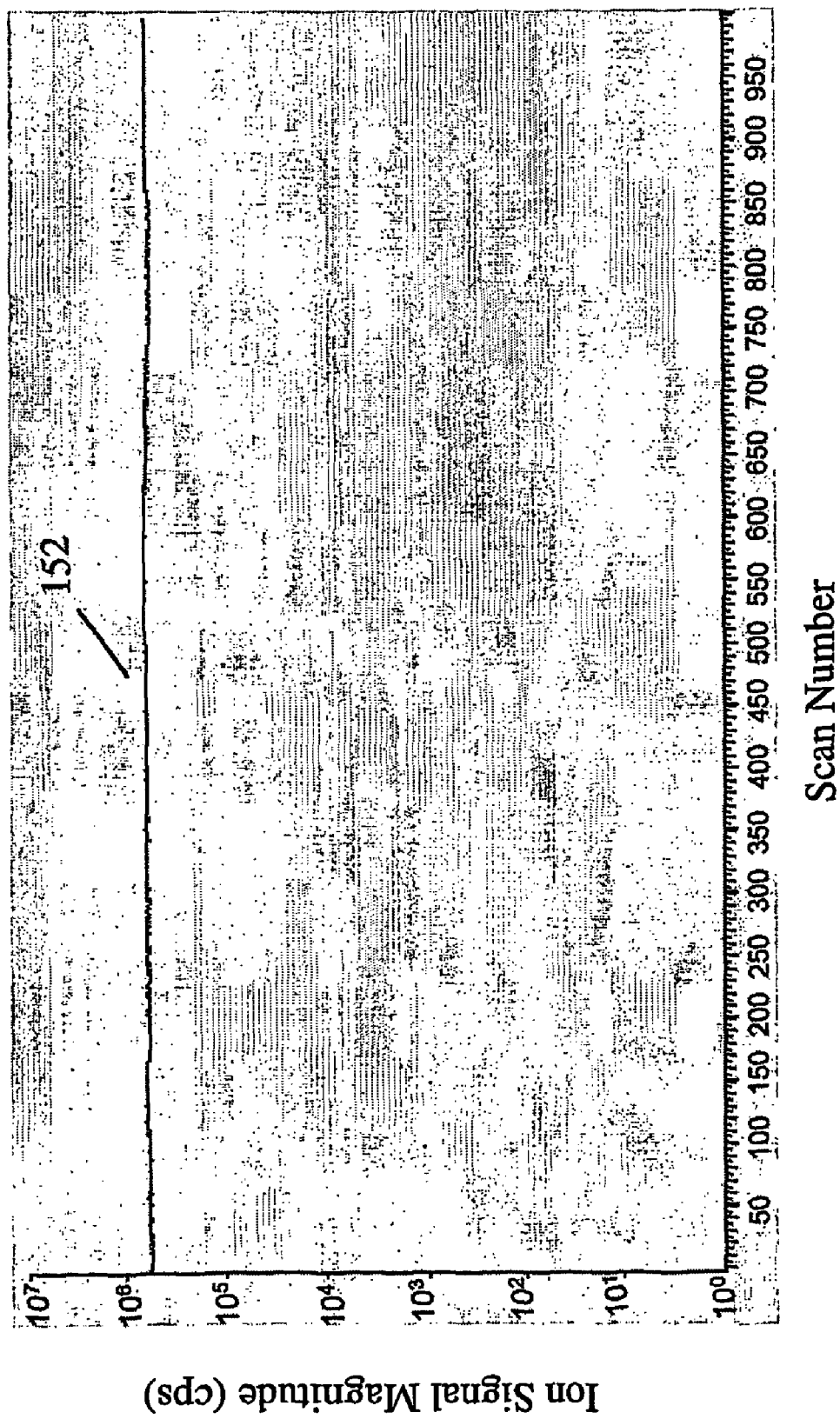
FIG. 12 is a graph of ion signal magnitude versus scan number measured from an operational sprayer in a dual sprayer ion source while the potential applied to the ion lens mounted on the other sprayer is cycled between an enabling potential and a disabling potential.

Referring now to FIG. 12, an experiment was conducted using the dual sprayer ion source 84 to show that the magnitude of an ion signal resulting from an enabled sprayer (i.e. hereafter referred to as the first sprayer) is not significantly affected when the potential applied to the ion lens mounted on the other sprayer (i.e. hereafter referred to as the second sprayer) is cycled between disabling and enabling potentials. In the experiment, the solution sample contained bradykinin. A potential of 6000 V was applied to each sprayer and a potential of 1961 V was applied to the curtain plate. The potential applied to the ion lens mounted on the first sprayer was 600 V and the potential applied to the ion lens mounted on the second sprayer is cycled between 600 V and 8500 V. Initially the potential applied to the ion lens mounted on the second sprayer is set at 8000 V. At approximately scans 150 and 650 the potential applied to the ion lens mounted on the second sprayer is ramped down to 600 V and at scans 500 and 850 the potential applied to the second lens is increased to 8500 V.

Figure 13:
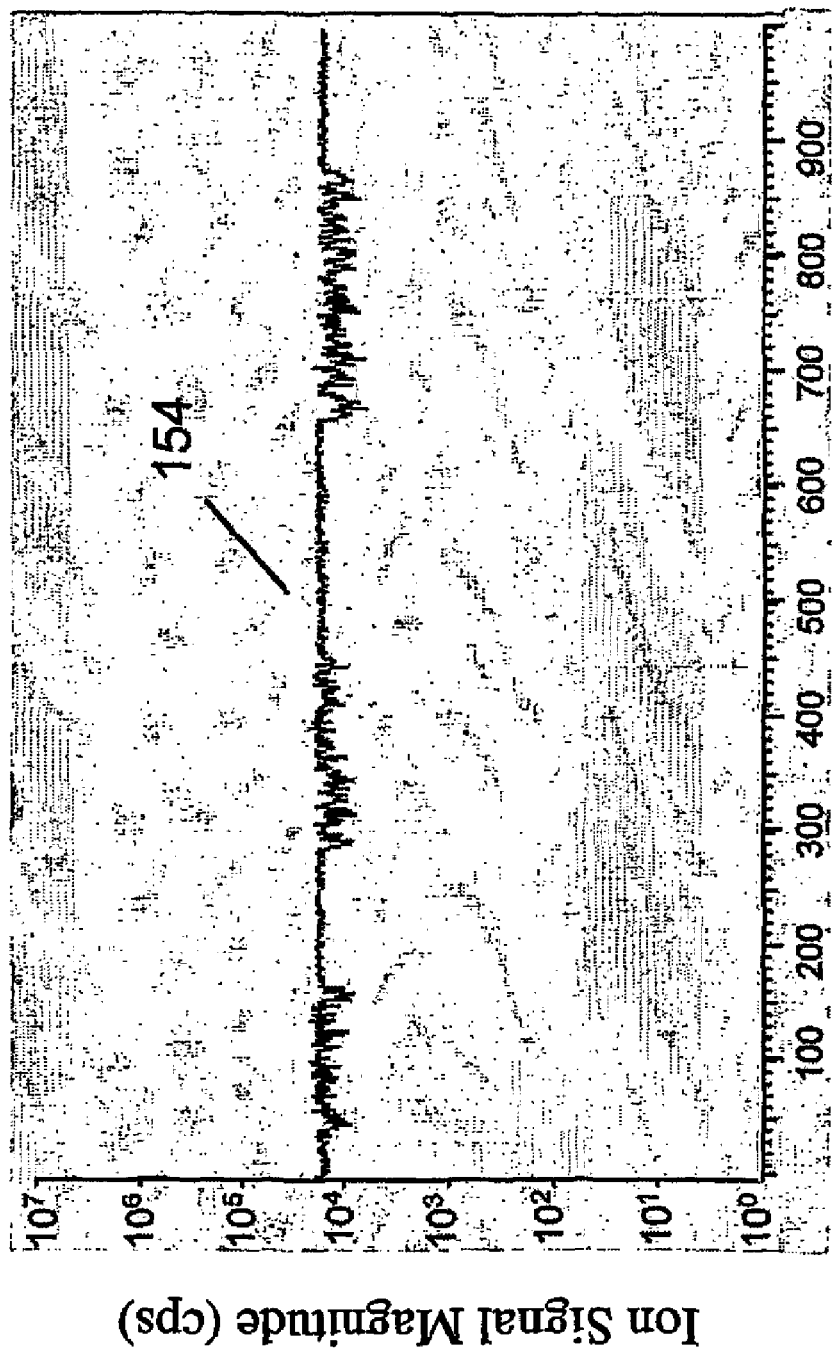
FIG. 13 is a graph of ion signal magnitude versus scan number measured from an operational sprayer in a dual sprayer ion source having a non-symmetrical sprayer mounting arrangement while the potential applied to the ion lens mounted on the other sprayer is cycled between an enabling potential and a disabling potential.

Referring now to FIG. 13, the aforementioned experiment was repeated with two changes. The positions of the two sprayers were not optimized with respect to a downstream orifice and the orientation of the sprayers was non-symmetrical. Curve 154 is the magnitude of the ion signal resulting from the ion spray generated by the first sprayer. The potential applied to the ion lens mounted on the second sprayer was initially set to 0 V and at approximately scan 40 the potential applied to the ion lens on the second sprayer was increased to a disabling potential (in this case 8500 V). The ion signal magnitude 154 is approximately the same, however, the stability of the ion signal was degraded. The reproducibility of this trend is evident in curve 154 as the potential applied to the ion lens mounted on the second sprayer was cycled between enabling (at approximately scans 180, 440, and 880) and disabling potentials (at approximately scans 40, 290, and 660).

All of the above experiments involve using a single power supply to control the potential applied to the sprayers in the dual and four sprayer ion sources. The use of one power supply results in a less expensive ion source, however, the sensitivity of the ion source system is compromised since the same potential is applied to each sprayer. If the location of the sprayers and the ion lenses mounted on the sprayers is symmetrical with respect to the entrance aperture of the mass spectrometer, one may expect that it is sufficient to apply the same potential to each sprayer. However, the inventors of the present invention have found experimentally that this is not the case. It is difficult to build identical sprayers, but it is possible to compensate for this with the potential applied to the sprayers. Therefore, lower precision sprayers may be used if the potential applied to each sprayer can be adjusted. Therefore, the use of a single power supply limits the effectiveness of the multisprayer ion source because the applied potential is not optimized for each sprayer but is rather a compromise when all sprayers are taken into account. However, experiments have shown that it is possible to compensate for this by altering the potential applied to each ion lens.

Figure 14A:
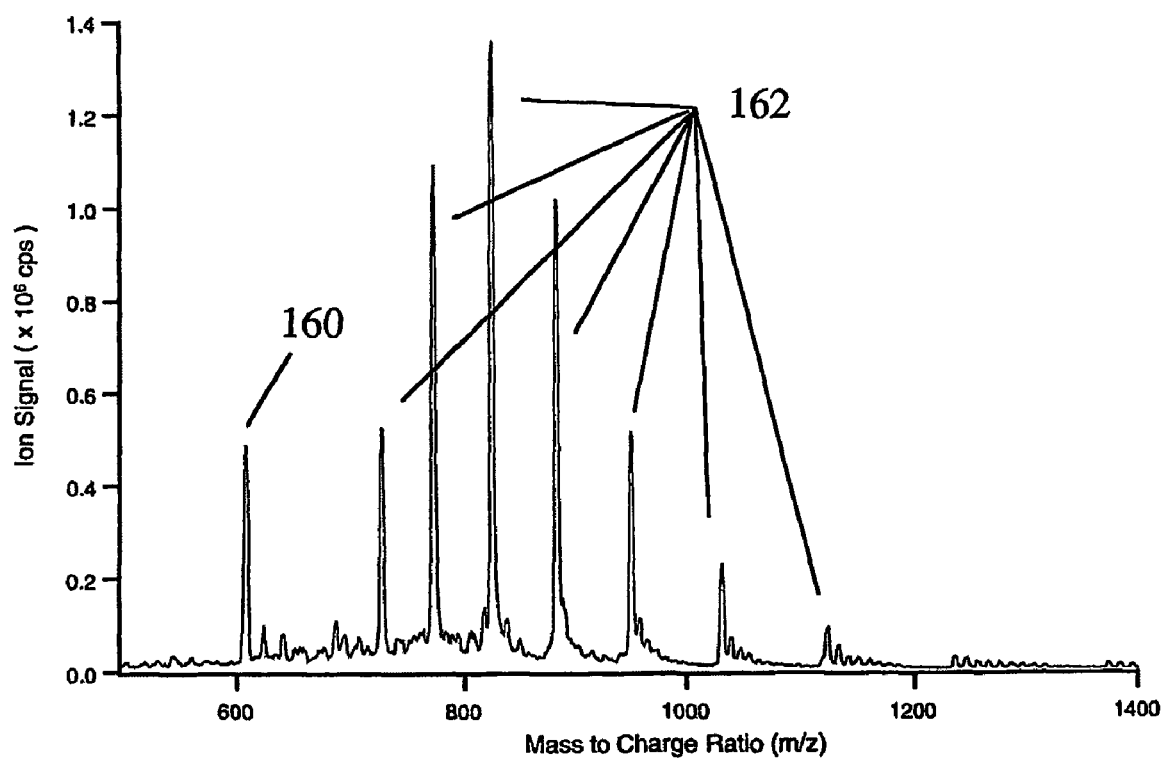
FIG. 14a is a mass spectrum obtained from a dual sprayer ion source in which both sprayers are operational and one sprayer is given a cyctochrome c sample solution and the other sprayer is given a reserpine sample solution.
Figure 14B:
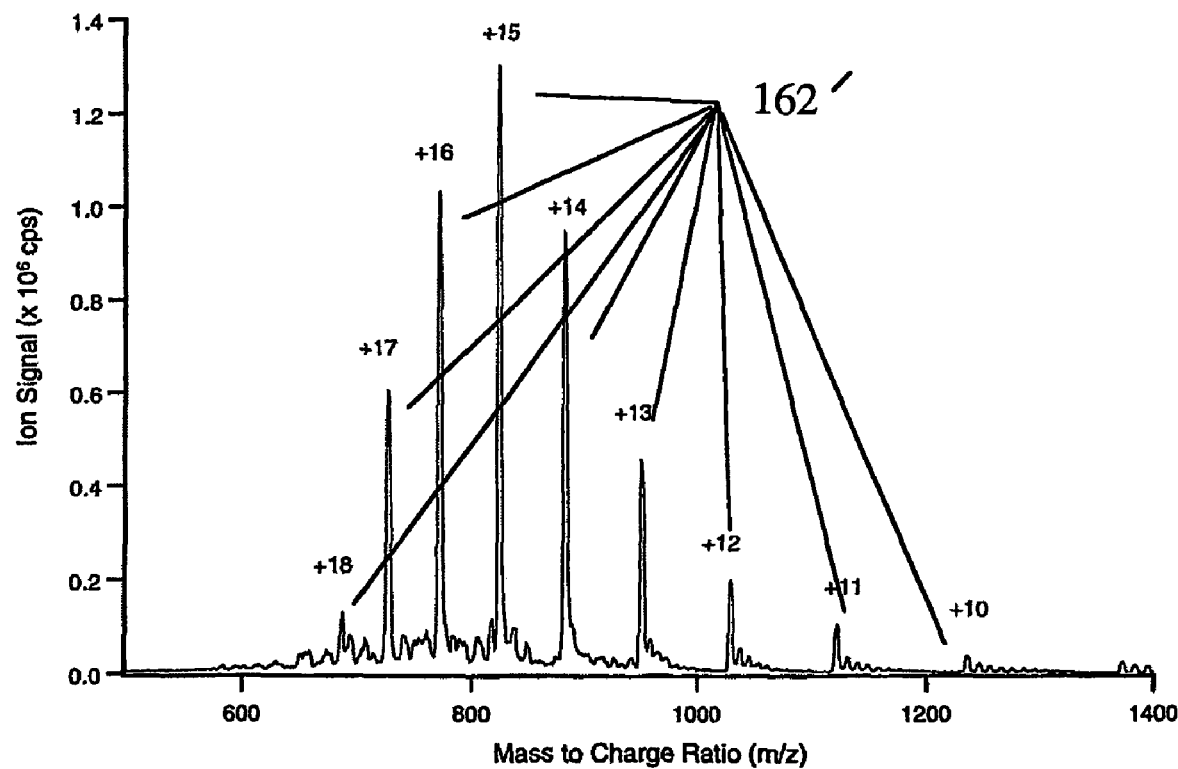
FIG. 14b is a mass spectrum obtained from the dual sprayer ion source of FIG. 14a in which the sprayer receiving the cytochrome c sample solution is operational and the sprayer receiving the reserpine sample solution is disabled.
Figure 14C:
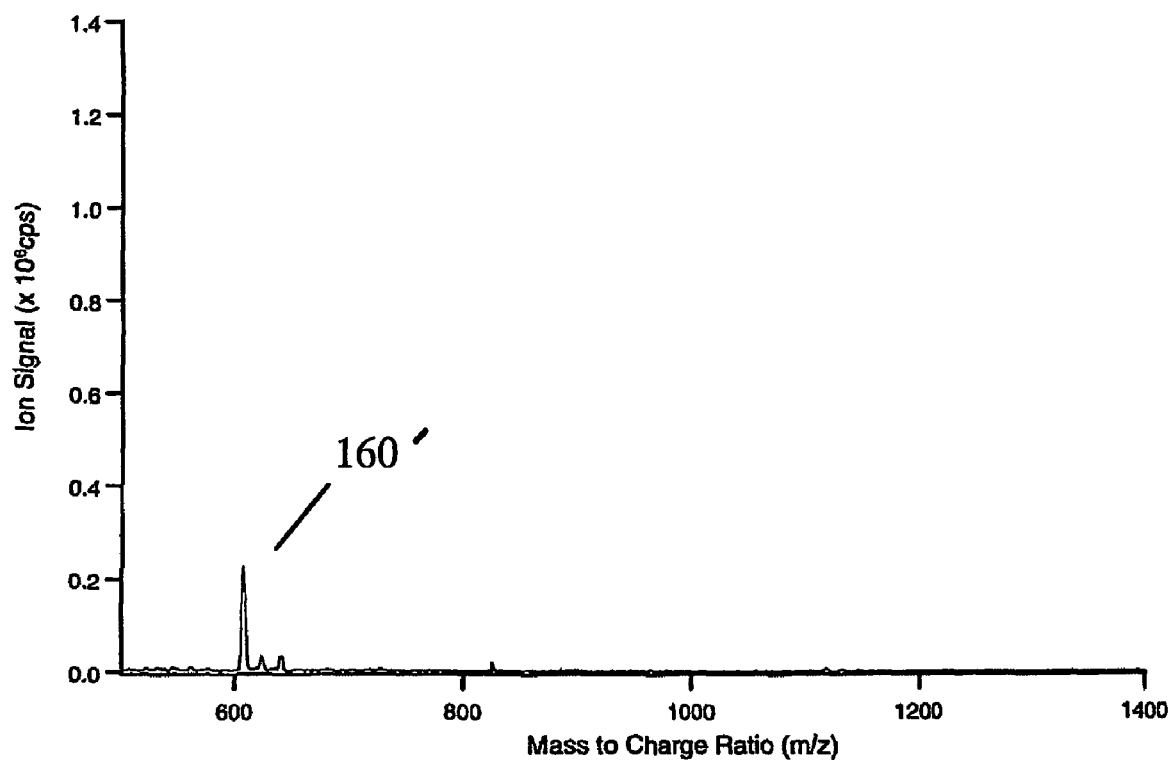
FIG. 14c is a mass spectrum obtained from the dual sprayer ion source of FIG. 14a in which the sprayer receiving the cytochrome c sample solution is disabled and the sprayer receiving the reserpine sample solution is re-enabled.

Referring now to FIGS. 14a, 14b and 14c, an experiment was conducted with the dual sprayer ion source 84 using one power supply to apply the same potential to each sprayer. One sprayer (i.e. the first sprayer) was given a sample solution containing reserpine and the other sprayer (i.e. the second sprayer) was given a sample solution containing cytochrome c. FIG. 14a shows the resulting mass spectrum when both sprayers are operational. The mass spectrum contains a peak 160 representing reserpine and a series of peaks 162 representing the various charge states of cytochrome c. In this case, the applied potentials were 6500 V for both sprayers, 1800 V for the curtain plate, 4000 V for the ion lens mounted on the first sprayer and 2500 V for the ion lens mounted on the second sprayer. These data demonstrate that two different analytes can be sprayed simultaneously from the two sprayers, and ions from each can be detected. For example, one sprayer may contain a sample solution, and the other may contain mass calibrants, internal standards, or other samples.

The potential applied to the ion lens mounted on the first sprayer was then set to a disabling potential (i.e. 8000 V) to effectively shut off the first sprayer. FIG. 14b shows the resulting mass spectrum which only contains the peaks 162' corresponding to the various charge states of cytochrome c. The magnitude of these peaks 162' is very similar to the magnitude of the peaks 162 shown in FIG. 14a. This indicates that the ion spray generated by the second sprayer is hardly affected by the disabling potential applied to the ion lens mounted on the first sprayer.

The potential applied to the ion lens mounted on the first sprayer was then set to the enabling potential (i.e. 4000 V) and the potential applied to the ion lens mounted on the second sprayer was then set to the disabling potential (i.e. 8000 V). FIG. 14c shows the resulting mass spectrum in which the peaks corresponding to the various charge states of cytochrome c have been eliminated and the peak 160' corresponding to reserpine reappears. However, the magnitude of the peak 160' is 50% that of the peak 160 shown in FIG. 14a. This attenuation is due to the fact that a single power supply is used to apply the same potential to both of the sprayers. If a second power supply were available then the potential applied to each sprayer could be further optimized.

Figure 15A:
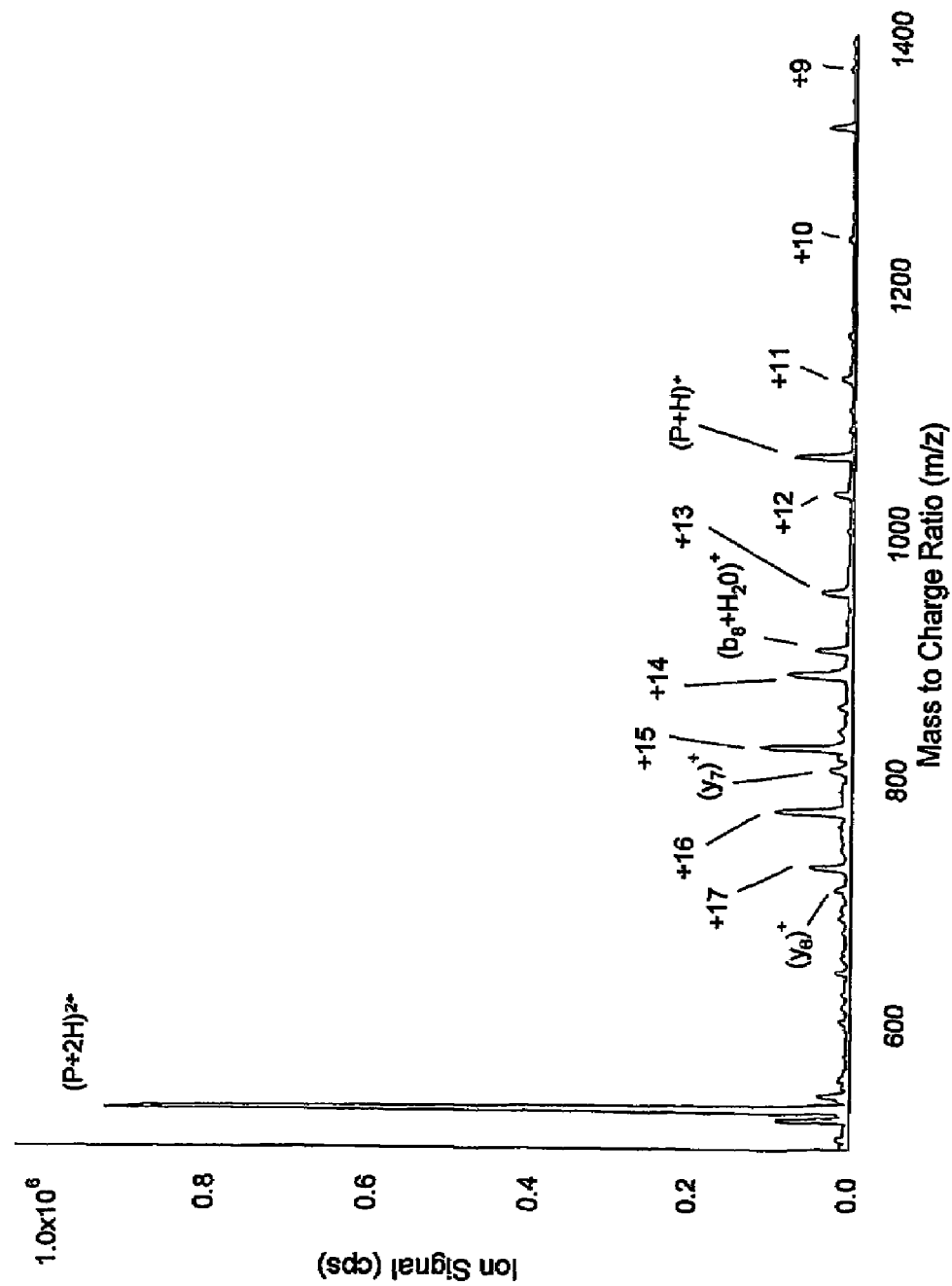
FIG. 15a is a mass spectrum obtained from a dual sprayer ion source in which both sprayers are operational and one sprayer is given a bradykinin sample solution and the other sprayer is given a cytochrome c sample solution.
Figure 15B:
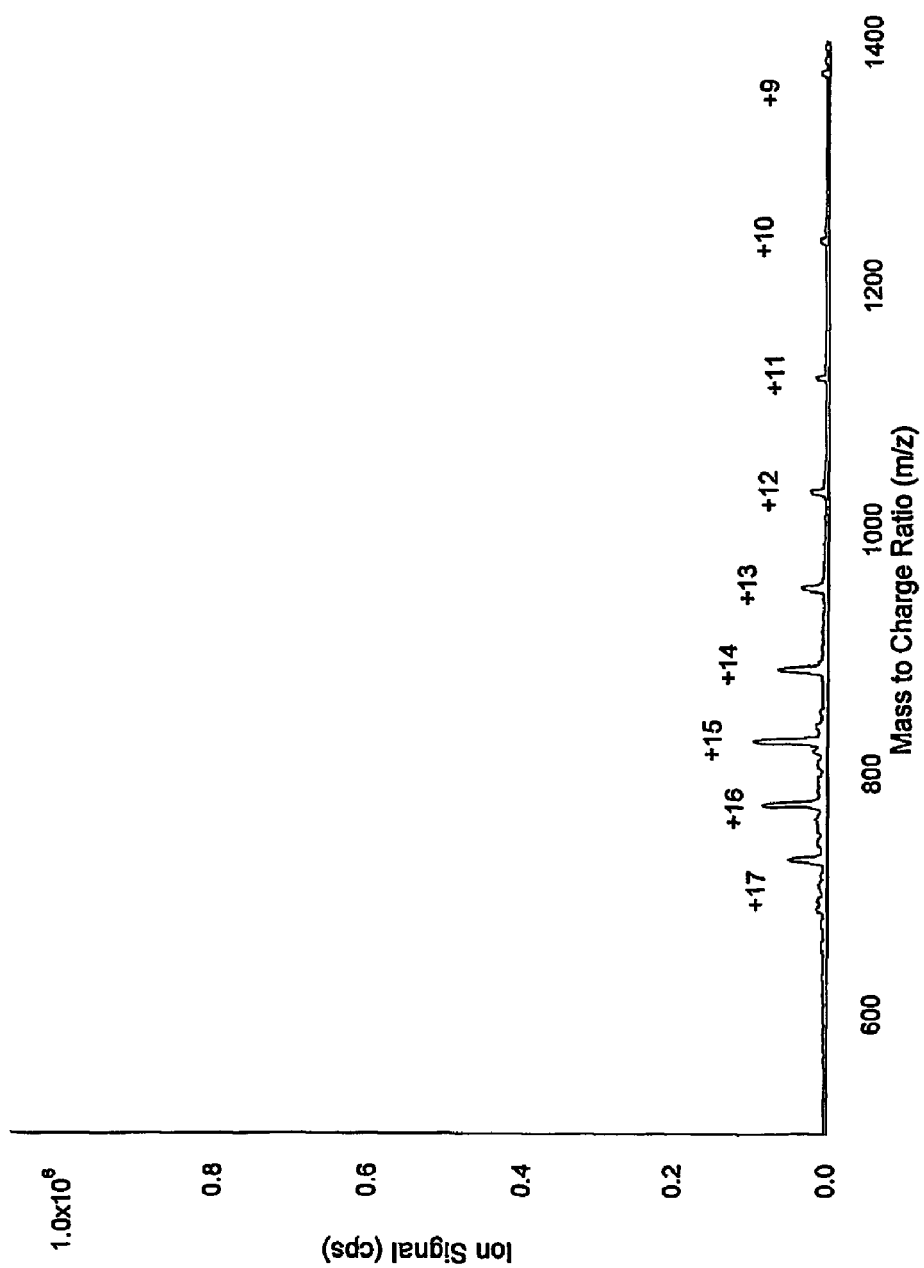
FIG. 15b is a mass spectrum obtained from the dual sprayer ion source of FIG. 15a in which the sprayer receiving the bradykinin sample solution was disabled and the sprayer receiving the cyctochrome c sample solution was enabled.
Figure 15C:
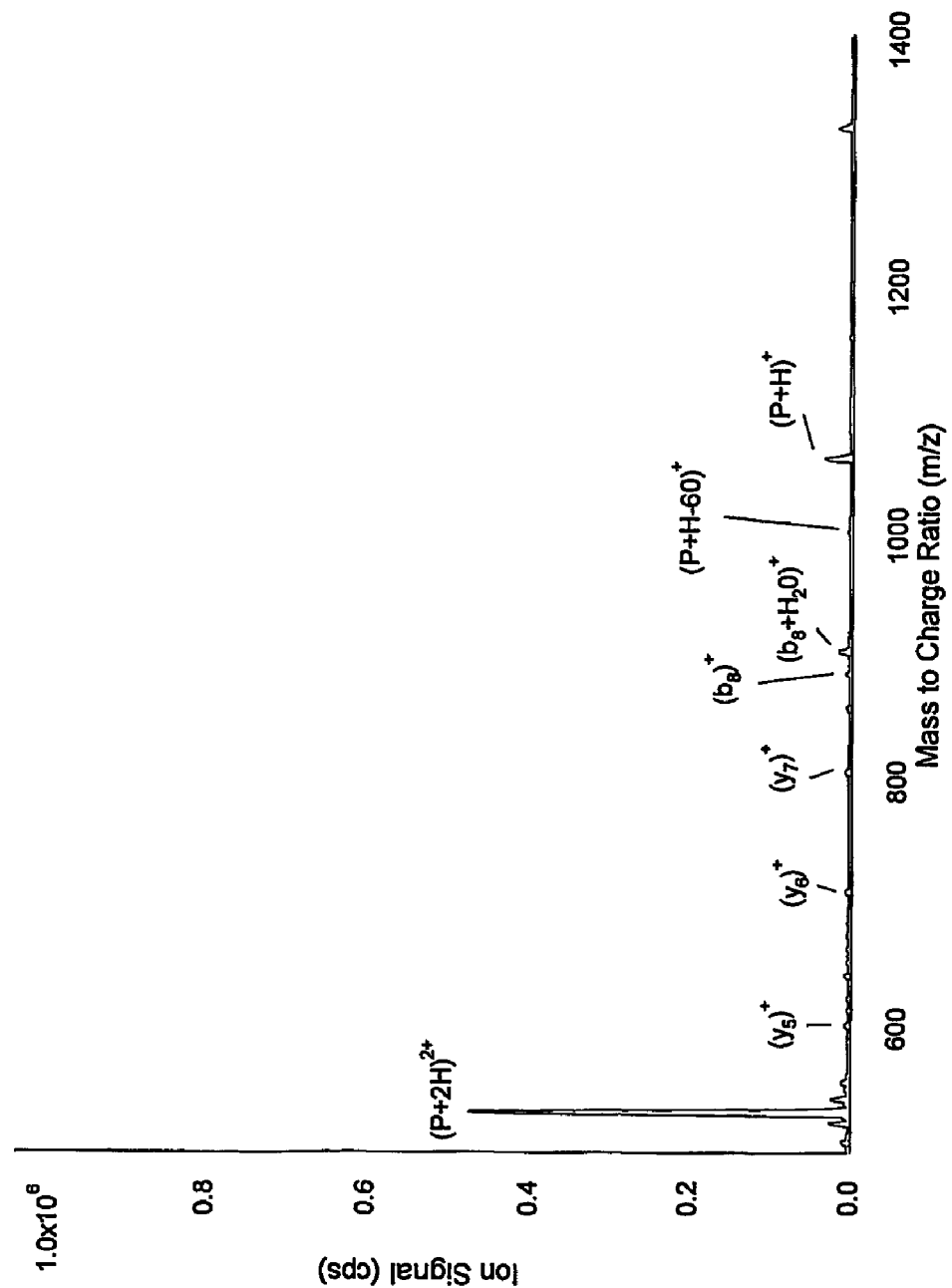
FIG. 15c is a mass spectrum obtained from the dual sprayer ion source of FIG. 15a in which the sprayer receiving the bradykinin sample solution was re-enabled and the sprayer receiving the cytochrome c sample solution was disabled.

Referring now to FIGS. 15a, 15b and 15c, an experiment similar to that just discussed was conducted using the same experimental setup and the same applied potentials. In this case, the first sprayer was provided with a sample solution containing bradykinin and the second sprayer was provided with a sample solution containing cytochrome c. FIG. 15a shows the resulting mass spectrum, with both sprayers operational, having peaks corresponding to singly protonated bradykinin $(P+H)^+$, doubly protonated bradykinin $(P+2H)^{2+}$, and bradykinin fragments labeled $(y_5)^+$, $(y_6)^+$, $(y_7)^+$, $(b_8)^+$, $(b_8+H_2O)^+$, and $(P+H-60)^+$ and peaks corresponding to various charge states of cytochrome c labeled +9, +10, +11, +12, +13, +14, +15, +16 and +17. The most intense peak in the mass spectrum corresponds to doubly protonated bradykinin. However, there are also smaller peaks corresponding to singly protonated bradykinin, bradykinin fragments and a wide range of charge states for cytochrome c. FIG. 15b shows the mass spectrum obtained while the first sprayer was disabled. The magnitude of the peaks corresponding to the various charge states of cytochrome c have decreased by 10% compared to the magnitude of those same peaks shown in FIG. 15a. FIG. 15c shows the mass spectrum obtained after the first sprayer was re-enabled and the second sprayer was disabled. The magnitudes of the peaks corresponding to bradykinin have decreased 50% compared to the magnitudes of those same peaks shown in FIG. 15a. These experimental results show that even though the potentials applied to the two sprayers are identical and the sprayers are similarly aligned with the entrance aperture of the downstream mass spectrometer, the sprayers do not behave identically.

Figure 16:
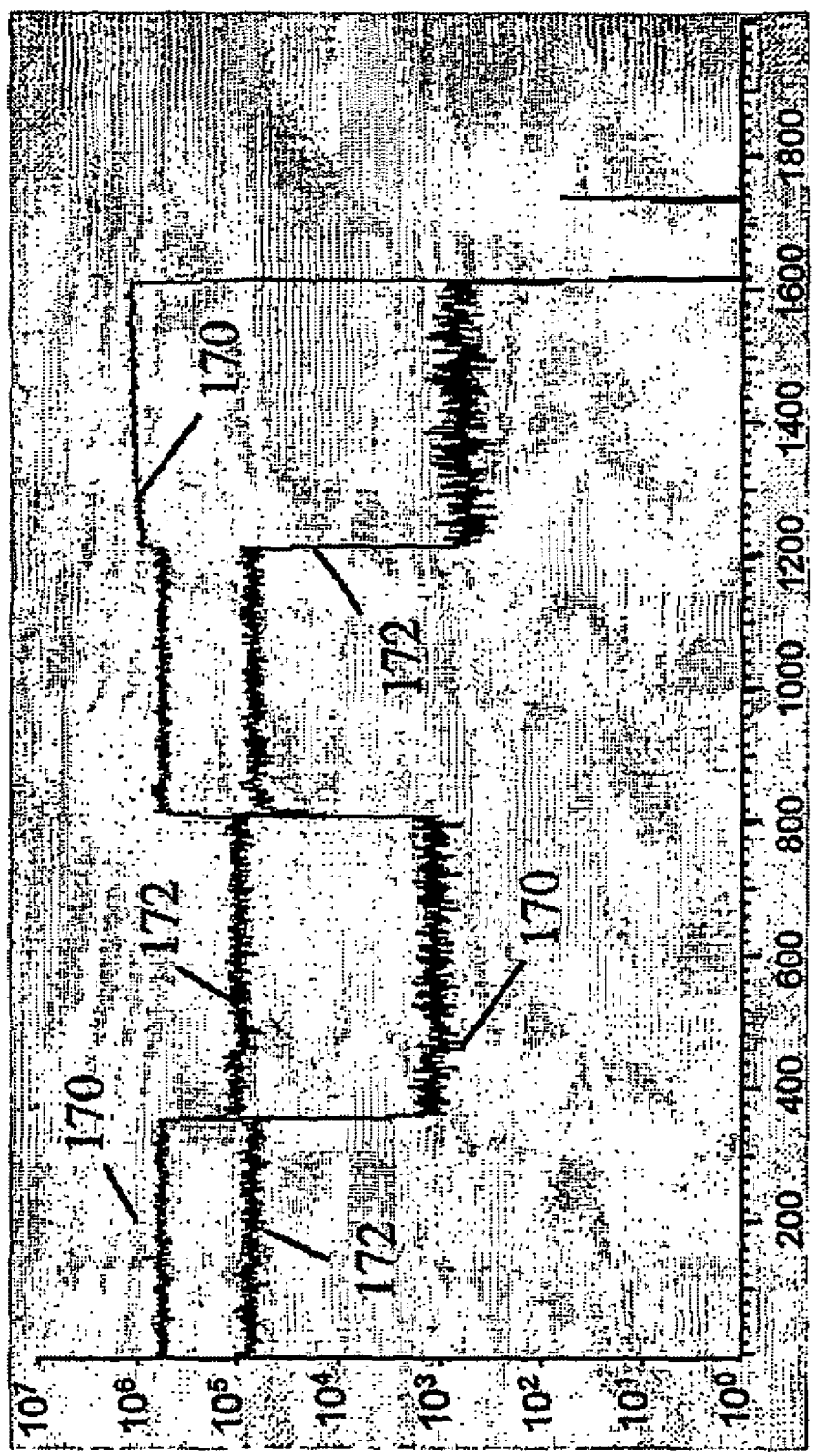
FIG. 16 is a graph of ion signal magnitude versus scan number measured for a dual sprayer ion source in which the potential applied to the ion lens mounted on each sprayer is varied and separate power supplies are used for each sprayer.
Figure 18B:
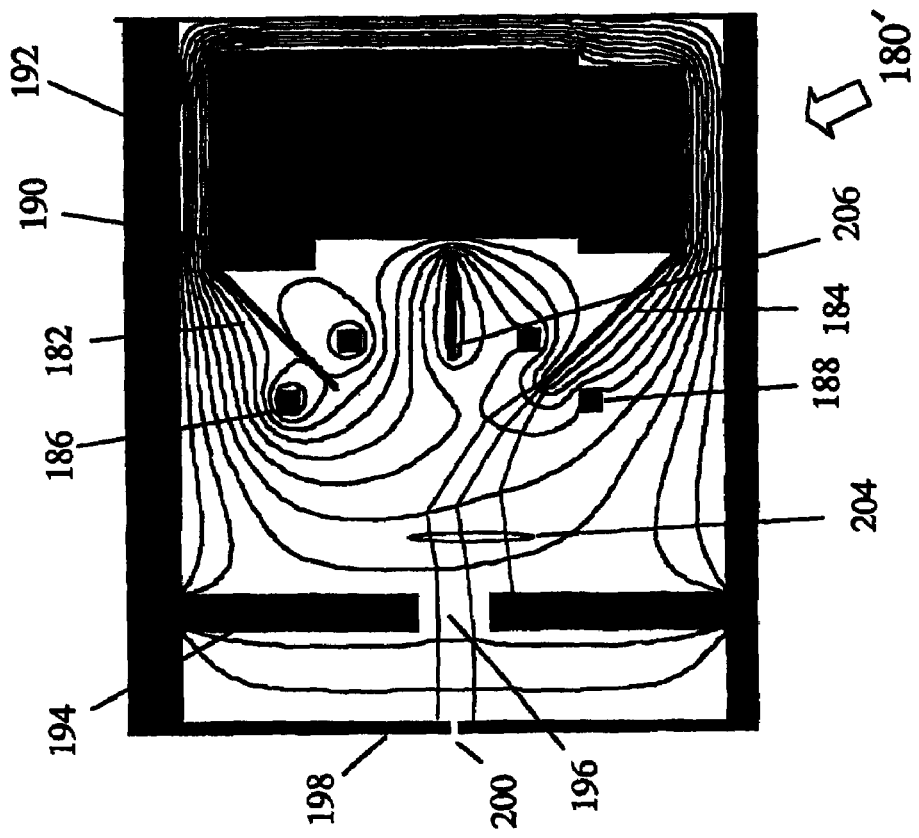
FIG. 18b is a simulation result for a dual sprayer ion source having an additional electrode means with one operational sprayer and one disabled sprayer.
Figure 18A:
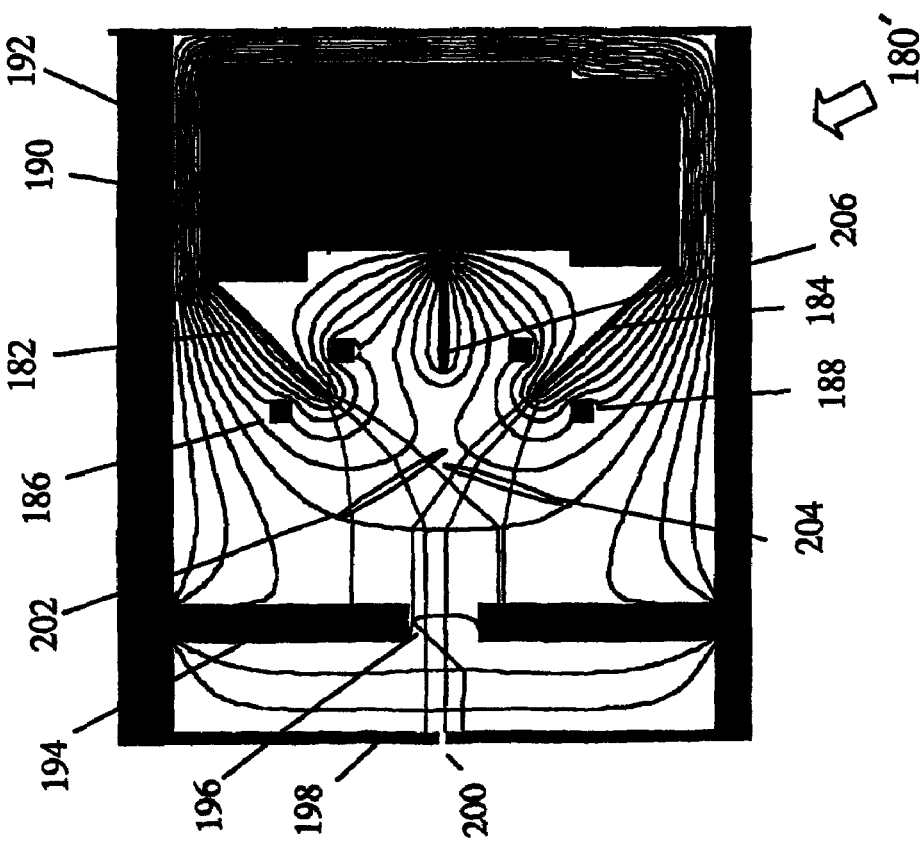
FIG. 18a is a simulation result for a dual sprayer ion source having an additional electrode means with both sprayers operational.
Figure 19:
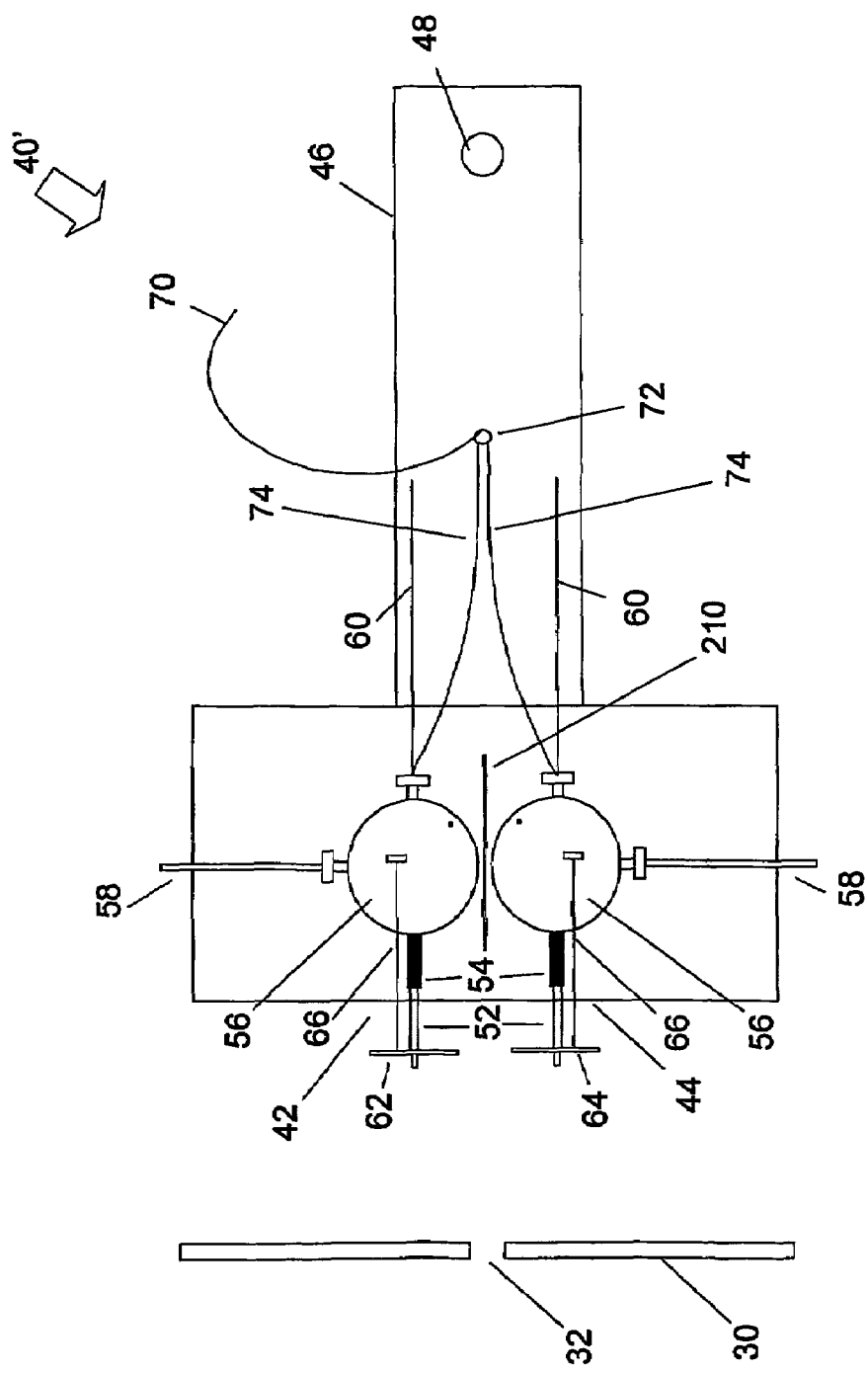
FIG. 19 is an alternative embodiment of the dual sprayer apparatus.

In another experiment, a different embodiment of the dual sprayer ion source 84 was used in which there were four power supplies. Each sprayer and ion lens was connected to a separate power supply which made it possible to improve the ion spray generated by each sprayer. The potential applied to the first sprayer was 6000 V and the potential applied to the second sprayer was 6918 V. The potential applied to the ion lens mounted on the first sprayer was 1800 V and the potential applied to the ion lens mounted on the second sprayer was 3000 V. A potential of 1835 V was applied to the curtain plate. The potentials applied to the sprayers and the ion lenses were adjusted to provide the maximum ion signal for the situation in which neighboring ion lenses were maintained at a high potential (i.e. a disabling potential). The sample solution provided to the first sprayer contained bradykinin and the sample solution provided to the second sprayer contained reserpine. The experimental results are shown numerically in Table 2 and graphically in FIG. 16. In Table 2, columns 1 and 2 indicate the type of ion in each analyzed sample and the mass to charge ratio of each ion, respectively. Column 3 indicates the magnitude of each ion signal when both sprayers were enabled. Column 4 indicates the magnitude of each ion signal when the potential applied to the ion lens on the first sprayer was increased to 6500 V to disable the first sprayer. In this case, the ion signal for bradykinin was eliminated and the ion signal for reserpine increased. Column 5 indicates the magnitude of each ion signal when the potential applied to the ion lens on the first sprayer is decreased to 1800 V to re-enable the first sprayer and the potential applied to the ion lens on the second sprayer is increased to 8000 V to disable the second sprayer. In this case, the ion signal for reserpine was eliminated and the ion signal for the bradykinin sample reappeared and increased relative to the value shown in column 3 when both sprayers were operational. These experimental results show that the use of separate power supplies for each sprayer and each ion lens makes it possible to adjust the potentials applied to these elements to improve the detection of the resulting generated ions within a downstream mass spectrometer.

TABLE 2

Ion Signal magnitude for Bradykinin and Reserpine with separate
power supplies for each sprayer and ion lens

| Ion | m/z ratio | Both sprayers 1 and 2 are on | sprayer 1 is off | sprayer 2 is off |
|---|---|---|---|---|
| Bradykinin + 2H$^+$ | 531 | 8.088E05 | 4.20E02* | 1.283E06 |
| Reserpine + H$^+$ | 609 | 1.224E05 | 1.577E05 | 9.80E02* |

*magnitude approximately equals the instrument noise

These experimental results also show that when a sprayer is disabled, the ion signal produced by the sprayer should decrease to less than the residual background noise level which is due to the sprayer that is operational. This feature is shown in Table 2 where the measured signals marked with an asterisk are purely background noise from the operational sprayer. No peak from bradykinin was observed in the mass spectrum of reserpine, and no peak from reserpine was observed in the mass spectrum of bradykinin. This feature is also shown in FIG. 16 where, the ion signal is plotted vs the scan number. The scans were 50 ms long, so the horizontal axis may also be considered to be a time axis. The experiment begins with both sprayers being operational. At approximately scan 290, the potential applied to the ion lens mounted on the first sprayer increases from 1800 V to 6500 V. Accordingly, the magnitude of the detected signal (having a mass to charge ratio of 531) 170 decreases to the residual noise level due to the operational second sprayer. During this time, the reserpine ion signal 172 increases somewhat. At approximately scan 810, the potential applied to the ion lens mounted on the first sprayer was decreased back to 1800 V. Accordingly, the magnitude of the doubly protonated bradykinin ion signal 170 returns to its previous value and the magnitude of the reserpine ion signal 172 decreases a bit to its previous value. At approximately scan 1220, the potential applied to the ion lens mounted on the second sprayer increases from 3000 V to 8000 V. Accordingly, the magnitude of the signal 172, at a mass to charge ratio of 609, decreases to the residual noise level due to the operational first sprayer. During this time, the magnitude of the doubly protonated bradykinin ion signal 170 increases marginally. At approximately scan 1610, the potential applied to the ion lens mounted on the first sprayer increases to 6500 V. Now both sprayers are disabled. The results in FIG. 16 show that the presence of a disabling potential on both ion lenses completely shuts off both sprayers and eliminates the ion signal for both samples except for a spurious noise spike at approximately scan 1740. The data presented in FIG. 16 also demonstrate that the two sprayers behave similarly when separate electrospray power supplies are used to provide potentials to each sprayer.

Referring now to FIGS. 17*a* and 17*b*, two dimensional simulation results for a dual sprayer ion source 180 are shown. The dual sprayer ion source 180 comprises two sprayers 182 and 184 each having an ion lens 186 and 188 (approximated by blocks) mounted thereon. The sprayers 182 and 184 are mounted on a sprayer mount 190 which is installed in a housing 192 having a curtain plate 194 with an aperture 196 and an orifice plate 198 with an orifice 200. In FIG. 17*a*, both sprayers 182 and 184 and lenses 186 and 188 have potentials applied to them that simulate the potentials that would be used during operation. A potential of 6500 V is applied to each sprayer 182 and 184 and a potential of 3500 V is applied to each ion lens 186 and 188. Potentials of 1800 V, 190 V and 0 V are applied to the curtain plate 194, the orifice plate 198 and the housing 190 respectively. The solid lines are the equipotential lines (the contour interval between adjacent equipotential lines is 600 V) that exist due to the applied potentials. However, the solid lines emanating from the tip of the sprayer 182 are the approximate trajectories 202 that ions from the ion spray generated from the sprayer 182 would travel along in the absence of a nebulizer gas flow. Likewise, the solid lines emanating from the tip of the sprayer 184 are the trajectories 204 that ions from the ion spray generated from the sprayer 184 would travel along. The trajectories 202 and 204 were included to qualitatively show the direction and spread of the ions generated from each sprayer 182 and 184. However, the results are approximate since the simulation cannot account for nebulizer gas, space charge, and the exact location of ion generation.

Referring now to FIG. 17*b*, the applied potentials are the same as those used to obtain the results shown for FIG. 17*a* except that the potential applied to the ion lens 186 has been increased to 8000 V to disable the sprayer 182. As can be seen from a comparison between FIGS. 17*a* and 17*b*, the increase in the potential applied to the ion lens 186 has a detrimental effect on the trajectories 204 for the ions in the ion spray generated by the sprayer 184. In fact, this effect may have previously been observed in FIGS. 14*a-c* and 15*a-c*.

Further modeling suggests that the detrimental ion trajectory effect seen in FIG. 17*b* may be alleviated by incorporating another electrode means into the dual sprayer ion source 180. Referring now to FIG. 18*a*, shown therein are simulation results for a dual sprayer ion source 180' that contains the same components as the dual sprayer ion source 180 along with an additional electrode means 206. The electrode means 206 is mounted on the non-conductive sprayer mount 190 (the attachment is not shown) and is placed approximately halfway between the sprayers 182 and 184. The potential applied to the electrode means 206 may be optimized to help isolate a sprayer from the potential applied to the ion lenses mounted on the other sprayers. The potentials applied to the dual sprayer ion source 180' to obtain the simulation results shown in FIG. 18*a* were the same as those used to obtain the results shown in FIG. 17*a*. The potential applied to the electrode means 206 is 1800 V.

Referring now to FIG. 18*b*, shown therein are simulation results for the dual sprayer ion source 180' with the sprayer 182 disabled. Once again, a potential of 8000 V is applied to the ion lens 186 to disable the sprayer 182. The rest of the applied potentials are similar to those used to obtain the simulation results shown in FIG. 18*a*. In contrast to the difference between the simulation results shown in FIG. 17*a* and 17*b*, the equipotential lines near the tip of the sprayer 184 appear to be similar in FIGS. 18*a* and 18*b*. Thus, the incorporation of the electrode means 206, which is placed in a centered fashion between the sprayers 182 and 184, aids in shielding the sprayer 184 from the disabling potential applied to the ion lens 186. The electrode means 206 also improves the ion trajectory 204 (as compared to the degrading effect seen in FIG. 17*b*). Furthermore, initial experiments with a prototype based on the dual sprayer ion source 180' have shown that it is possible to vary the ion signal magnitude by varying the potential applied to the electrode means 206. This may be generalized to a multisprayer ion source having more than two sprayers in which case the electrode means would again be placed in a centered fashion between all of the sprayers.

Referring now to FIG. 19, shown therein is a partial view of an alternative embodiment of the dual sprayer apparatus 40' mounted in front of a curtain plate 30. The elements of the dual sprayer apparatus 40' are similar to the elements of the dual sprayer apparatus 40 shown in FIG. 2 except for the addition of an electrical insulation means 210. Accordingly, the elements in common between the dual sprayer apparatus 40 and the dual sprayer apparatus 40' have been given the same reference numbers and will not be discussed further. The main difference between the dual sprayer apparatus 40' and the dual sprayer apparatus 40 is the orientation of the sprayers 42 and 44. The dual sprayer apparatus 40' has a substantially parallel orientation of the sprayers 42 and 44 with both sprayers oriented generally orthogonally with respect to the curtain plate 30. This is in contrast to the dual sprayer apparatus 40 which had the sprayers 42 and 44 aligned towards the curtain plate 30 on an angle, such as a 45 degree angle, so that the sprayers 42 and 44 were oriented to point past the aperture 32 of the curtain plate 30. An additional difference between the dual sprayer apparatus 40' and the dual sprayer apparatus 40 is that the sprayer tees 56 have been moved very close to one another which requires an electrical insulation means 210, which may be a Teflon spacer, to electrically insulate each sprayer 42 or 44 from the potentials applied to the other sprayer 44 or 42. An insulating mount is used so that separate potentials can be applied to each sprayer 42 or 44.

Figure 20:
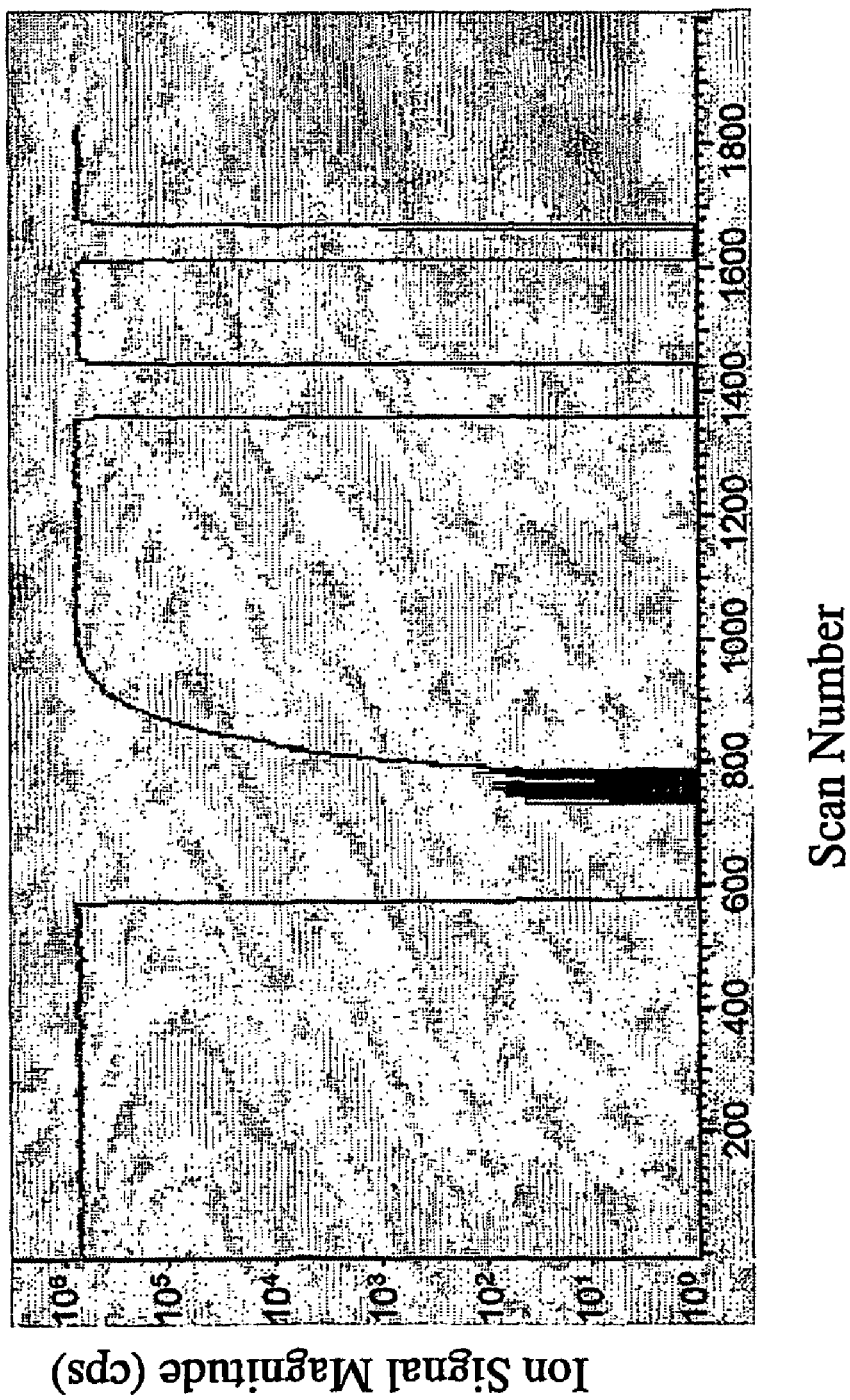
FIG. 20 is a graph of ion signal magnitude versus scan number measured using the dual sprayer apparatus of FIG. 19 with one of the sprayers being operational.

Referring now to FIG. 20, shown therein are experimental results obtained with the dual sprayer apparatus 40'. In the experiment, a $10^{-5}$ M bradykinin sample solution was provided to the sprayer 42. A sample solution was not provided to the sprayer 44. Potentials of 6268 V, 4300 V, 1835 V, and 190 V were applied to the sprayer 42, the ion lens 62, the curtain plate 30, and the orifice plate 34 respectively. Nebulizer gas was initially not provided to the dual sprayer apparatus 40'. Furthermore, the spacing between the tips of the sprayers 42 and 44 and the curtain plate 30 was approximately 1.8 cm and the horizontal spacing between the tips of the sprayers 42 and 44 was approximately 2 cm. Furthermore, the sprayer 42 was oriented approximately 0.5 to 0.8 cm to the left of the aperture 32 in the curtain plate 30.

The data in FIG. 20 show that a stable ion signal results from the ion spray generated by the sprayer 42. The plot shows ion signal vs the scan number. Each scan required 50 ms, so the x axis is proportional to time. The magnitude of the ion signal was found to be independent of the potential applied to the sprayer 44. At approximately scan 577, nebulizer gas was provided to the sprayer 42 which resulted in the disabling of the sprayer 42. The introduction of the nebulizer gas may blow the charged droplets in the ion spray generated by the sprayer 42 into the curtain plate 30 since prior to the introduction of the nebulizer gas to the sprayer 42, the ions and charged droplets in the generated ion spray moved towards and through the aperture 32 in the curtain plate 30. At approximately scan 728, the nebulizer gas was no longer provided to the sprayer 42 which resulted in the enabling of the sprayer 42. The magnitude of the ion signal then slowly returned to its previous value before the introduction of the nebulizer gas. At approximately scan 1360, the potential applied to the ion lens 62 was then rapidly increased from 4300 V to 8000 V which resulted in the disabling of the sprayer 42. The ion signal terminated approximately 50 ms after the disabling potential was applied to the ion lens 62. At approximately scan 1440, the potential applied to the ion lens 62 was decreased back to 4300 V which resulted in the enabling of the sprayer 42. The magnitude of the ion signal then returned to its previous value within approximately 50 ms. Once again, the ramping of the potential applied to the ion lens 62 was manually performed within a time period of approximately 1 second. The potential applied to the sprayer 42 was turned off on scan 1610, and then back on at scan 1630.

This experimental data illustrates that the dual sprayer apparatus 40' is capable of operating in a similar fashion as the dual sprayer apparatus 40. However, a nebulizer gas must not be provided to the operational sprayer in order to obtain an ion signal from the operational sprayer. This data also shows that an ion lens may be used with other types of sprayer arrangements as well as different types of sprayers (i.e. without a nebulizer gas flow, the sprayers 42 and 44 behave as electrospray ion sources rather than ion spray ion sources). The data further illustrates that a quicker response time in terms of disabling and enabling an ion signal can be achieved by using the potential applied to an ion lens rather than nebulizer gas flow.

Figure 21:
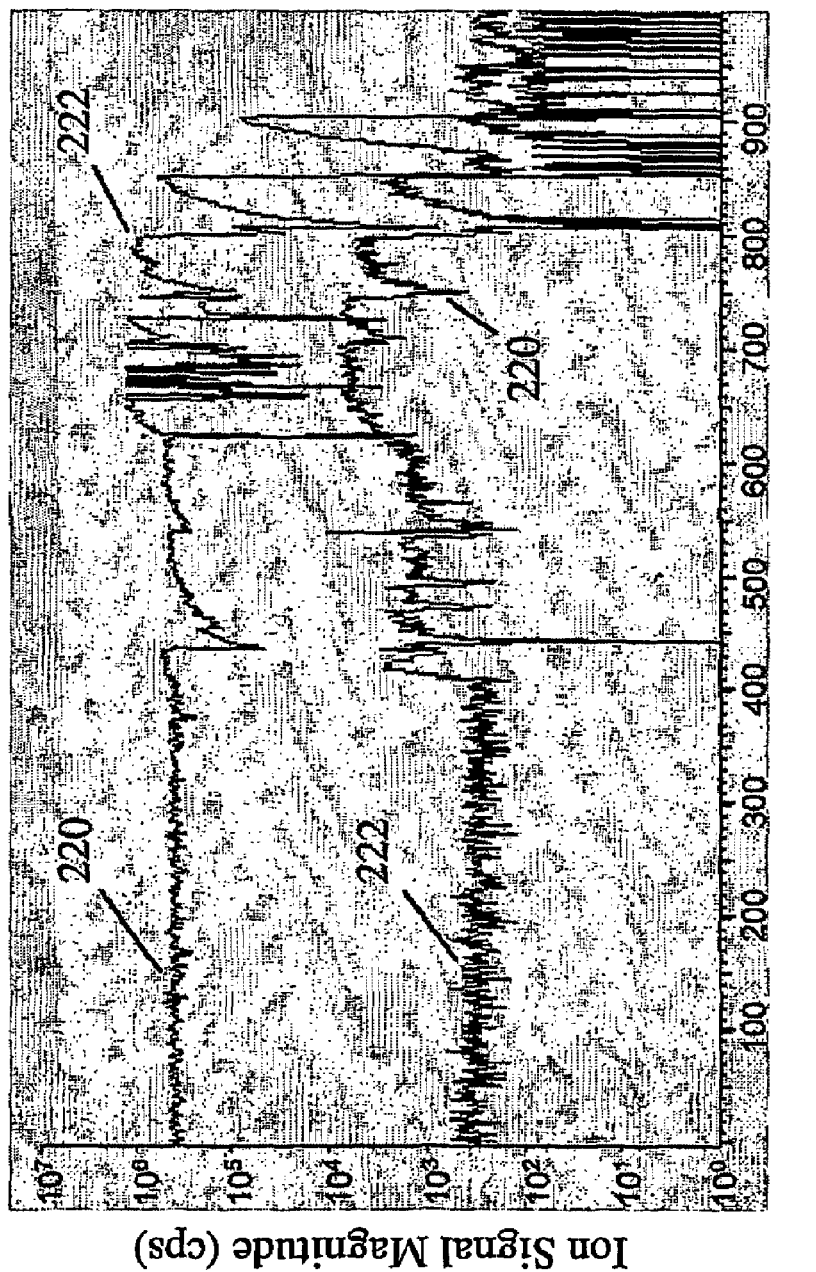
FIG. 21 is a graph of ion signal magnitude versus scan number-measured using a modified version of the dual sprayer apparatus of FIG. 19 with a bradykinin sample solution provided to one of the sprayers and a reserpine sample solution provided to the other sprayer.

Referring now to FIG. 21, shown therein are experimental results obtained after some modifications were made to the dual sprayer apparatus 40'. In particular, the sprayers 42 and 44 were moved closer together. The ion lenses 62 and 64 were spaced approximately 4 mm apart from each other. Furthermore, the sprayers 42 and 44 were oriented approximately 5 mm to either side of the aperture 32 in the curtain plate 30. In this experiment, a bradykinin sample solution was provided to the sprayer 42 and a reserpine sample solution was provided to the sprayer 44. Potentials of 6725 V and 3000 V were applied to the sprayer 42 and the ion lens 62 while no potentials were applied to the sprayer 44 and the ion lens 64.

The data in FIG. 21 illustrates that initially a strong ion signal 220 was obtained for doubly protonated bradykinin (having an m/z of 531) from the sprayer 42 and that noise 222 was observed at the mass to charge ratio of reserpine (i.e. an m/z of 609). At approximately scan 400, the potential applied to the sprayer 44 was increased to 6381 V. As a result the ion signal from the sprayer 42 destabilizes for a while before restabilizing and the magnitude of the ion signal from the sprayer 44 increases slightly but then destabilizes. At approximately scan 640, the potential applied to the ion lens 64 was increased to 3000 V which initially increased the magnitude of the ion signal from the sprayer 44 but eventually the ion signal from both sprayers 42 and 44 destabilize and drop off. Thereafter, an ion signal was not successfully re-obtained with both sprayers 42 and 44 operational.

The experimental results shown in FIG. 21 indicate that the dual sprayer apparatus 40' is not as effective as the dual sprayer apparatus 40 in generating ions because the potential applied to each ion lens 62 and 64 appears to repel the charged droplets generated by the other sprayer 42 and 44 so that these charged droplets do not pass through the aperture 32 in the curtain plate 30. Accordingly, the dual sprayer apparatus 40' appears to be useful in situations in which only one sprayer is operational at a time. For example, both sprayers may be connected to separate High Performance Liquid Chromatography systems (HPLCs). In this case when one sprayer is operational, the other sprayer may be in a rinse cycle and vice-versa. The sprayer in the rinse cycle would have low potentials applied to it. Furthermore, the sprayers 42 and 44 may have to be moved as close as possible to the aperture 32 in the curtain plate 30. However, although only one sprayer is operational at a time, such a system would still have increased throughput compared to a system having an ion source with a single sprayer. The dual sprayer apparatus 40' may also be useful for operating as a pulsed electrospray ion source or in systems like those disclosed by Covey (WO 01/44795) or Kato (JP2000357488) in which each sprayer, from a multi-sprayer ion source, is placed in front of each inlet aperture of a downstream mass spectrometer. In addition, this data suggests that for the dual sprayer apparatus 40', with the curtain plate 30 and the aperture 32, it is advantageous to have the sprayers 42 and 44 oriented so that the generated ion sprays pass in front of the aperture 32, or so that the generated ion sprays are as close to the aperture 32 as possible.

Figure 22A:
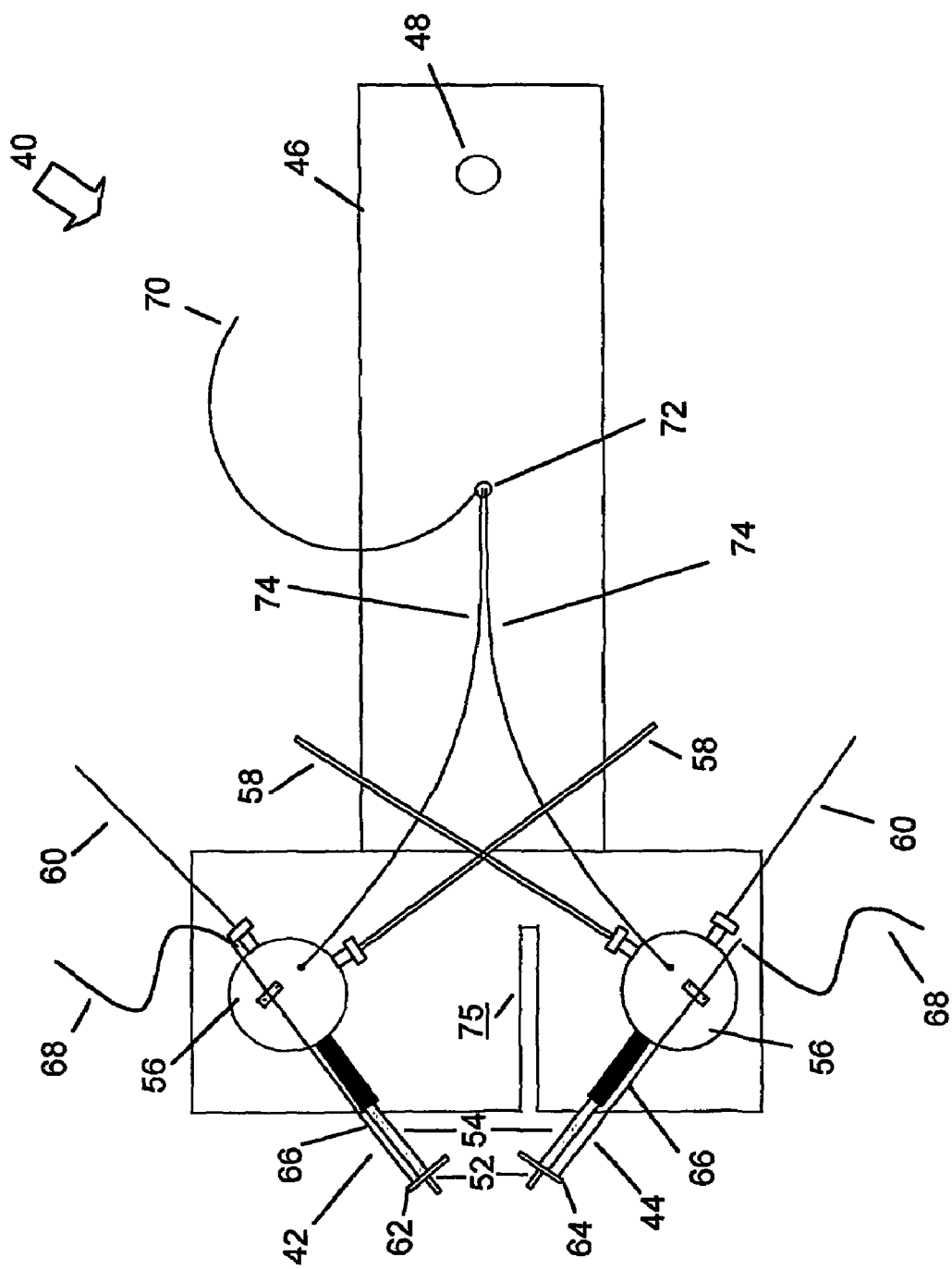
FIGS. 22a and 22b illustrate an alternative method of enabling and disabling a sprayer by moving the ion lens to the tip of the sprayer to disable the sprayer (FIG. 22b) and then moving the ion lens back from the tip of the sprayer to enable the sprayer (FIG. 22a)
Figure 22B:
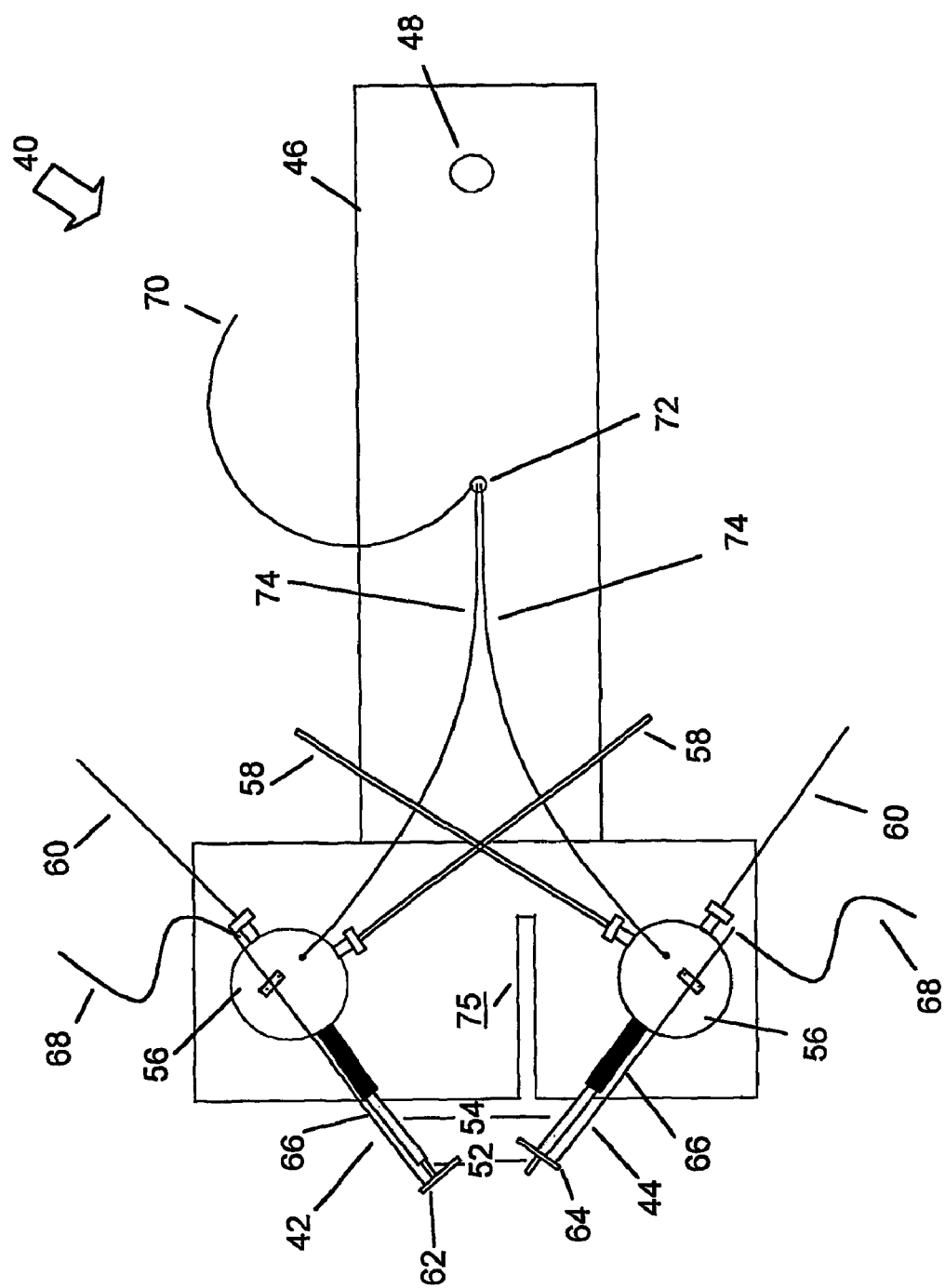

The inventors have also found that another method of enabling and disabling a sprayer involves moving an ion lens along the longitudinal axis of that sprayer. Referring now to FIG. 22a, shown therein is the dual sprayer apparatus 40 with both ion lenses 62 and 64 positioned so that the sprayers 42 and 44 may be operational depending on the potentials applied to these elements. The inventors have found that a sprayer may be disabled by applying a constant or varying potential to the ion lens 62 as it is moved towards the tip of the sprayer 42. Once the ion lens 62 reaches the tip of the sprayer 42, as shown in FIG. 22b, the sprayer 42 will be disabled. To re-enable the sprayer 42, the ion lens 62 may be moved backwards, away from the tip of the sprayer 42. In this method, the movement of the ion lens 62 near the tip of the sprayer 42 appears to decrease the effective electric field near the tip of the sprayer 42 to disable the sprayer 42. Accordingly, using this method, the ion lens 62 may be alternated between an enabling position, preferably 2 mm behind the tip of the sprayer 42, and a disabling position where the ion lens 62 is preferably located at the tip of the sprayer 42. This method of disabling and enabling a sprayer is beneficial since a large disabling potential does not need to be applied to the ion lens mounted on that sprayer. Consequently, if two or more sprayers are moved close together, there should not be much of an interference effect on a given sprayer from the potential applied to the ion lens mounted on the other sprayer since a high disabling potential is not required to disable a sprayer. However, a potential may still be applied to the ion lens as the ion lens is translated to various positions along the longitudinal axis of the sprayer. The translation of the ion lens 62 along the sprayer 42 may be effected by any means known in the art such as applying a stepper motor to the ion lens 62.

Figure 23:
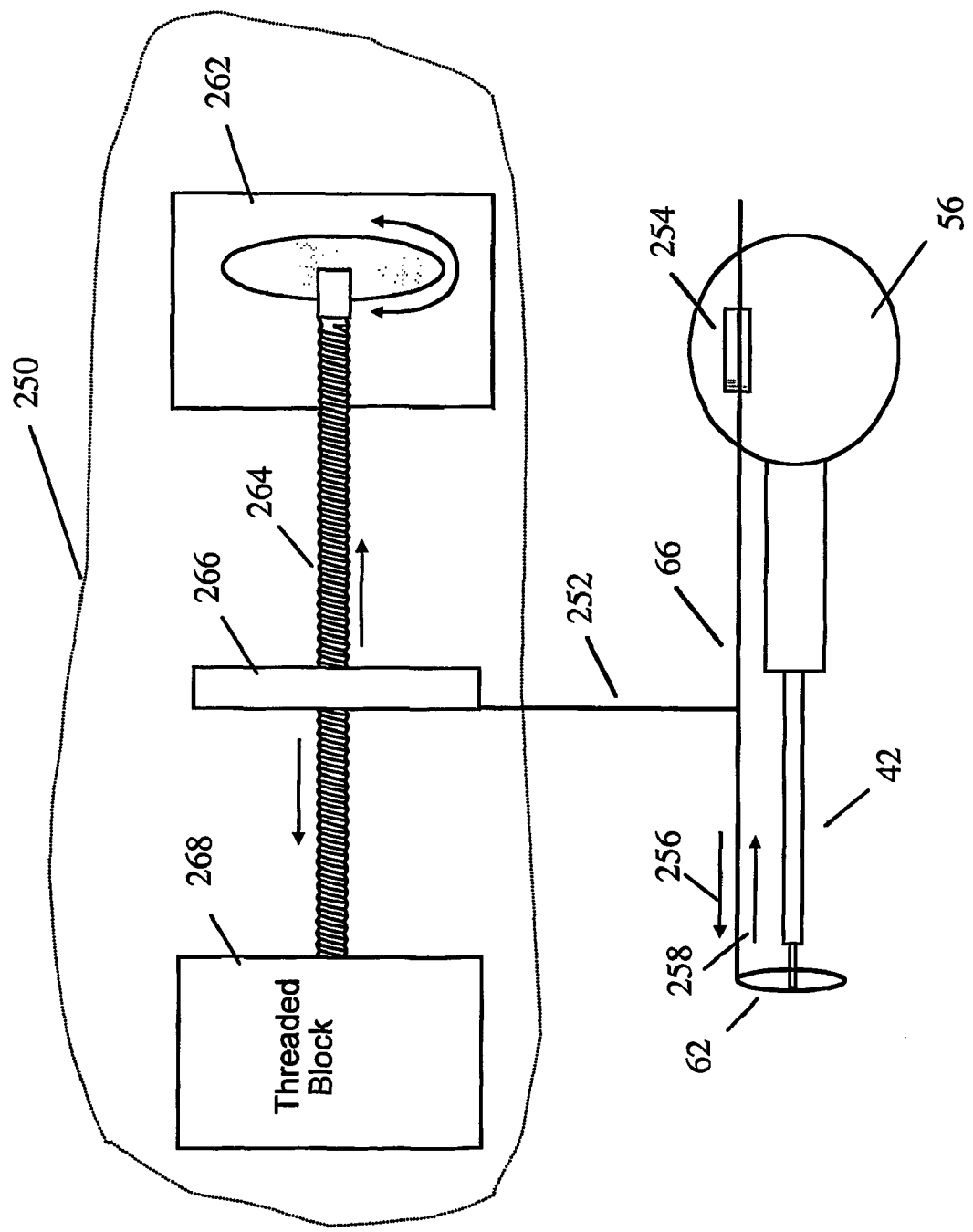
FIG. 23 is a partial view of an alternate embodiment of the dual sprayer apparatus of FIG. 2 with a translation means to alternate the ion lens between an enabling position and a disabling position.

Referring now to FIG. 23, shown therein is a partial view of an alternative embodiment of the dual sprayer apparatus 40 having a moveable ion lens 62 mounted on the sprayer 42. A translation means 250 is coupled to the mounting bracket 66 of the ion lens 62 via a coupling element 252. The mounting bracket 66 has also been modified to incorporate a sliding mount 254. The sliding mount 254 is adapted to hold the ion lens 62 in place while allowing the mounting bracket 66 to slide through the sliding mount 254 so that the ion lens 62 may be alternately located at an enabling position and a disabling position. The translation means 250 is adapted to move the mounting bracket 66 in a forwards and backwards motion illustrated by arrows 256 and 258. In this fashion, the ion lens 62 may be moved to the tip of the sprayer 42 (i.e. the disabling position) to disable the sprayer 42 and the ion lens 62 may be moved away from the tip of the sprayer 42 to enable the sprayer 42.

The translation means 250 may be implemented by any means known in the art. In particular, referring to FIG. 23, the translation means 250 may comprise a rotation means 262, a threaded shaft 264 that is operatively coupled to the rotation means 262, a moveable plate 266 that is mounted on the threaded shaft 264 and a threaded block 268 that is operatively coupled to the threaded shaft 264. The rotation means 262 may comprise a stepper motor having a rotating chuck into which the threaded shaft 264 is mounted. The moveable plate 266 is coupled to the coupling element 252 to impart a forward or rearward motion to the mounting bracket 66. The moveable plate 266 is fastened onto the threaded shaft 266 by any means known in the art including, but not limited to, double nut fastening or welding. Furthermore, in this embodiment, the mounting bracket 66 is preferably made from non-conductive material. Alternatively, the mounting bracket 66 may comprise a rod having a shielded coating.

In operation, the rotation means 262 provides a rotational force to the threaded shaft 264 to rotate the threaded shaft 264 in a clockwise or counter-clockwise direction. As the threaded shaft 264 is rotated in the clockwise direction, the threaded shaft 264 screws into the threaded block 268 and forces the moveable plate 266 to move towards the threaded block 268. This in turn causes the ion lens 62 to move towards the tip of the sprayer 42. Conversely, when the threaded shaft 264 is rotated in the counter-clockwise direction, the threaded shaft 264 un-screws itself from the threaded block 268 and forces the moveable plate 266 to move away from the threaded block 268. This in turn causes the ion lens 62 to move away from the tip of the sprayer 42. The maximum speed of the movement of the ion lens 62 from the enabling position to the disabling position and vice-versa is dictated by the speed of the stepper motor used in the rotation means 262. Since the total movement required for the ion lens 62 is on the order of millimeters, the ion lens 62 should move fairly quickly. If a large enough stepper motor was used in the rotation means 262, then the ion lens 62 should move quite rapidly from one position to the next. However, this method of sprayer control will likely be slower than the method of using the potential applied to the ion lens 62 to enable or disable the sprayer 42. It should also be mentioned that the translation means 250 may be adapted to vary the angle that the plane of the ion lens 62 makes with the longitudinal axis of the sprayer 42. This may be beneficial in altering the trajectories of the ions generated by the sprayer 42.

The subject invention may also be used for the development of a pulsed electrospray ion source. Recently, a pulsed electrospray ion source was described by Lu et al (*Analytical Chemistry*, 2001, 73, pp. 4748-4753). It was shown that pulses of ions could be generated by rapidly turning the potential applied to a sprayer off and on. However, this type of device is limited by the time required to stabilize the generated ion spray in the time period between the pulses in the potential applied to the sprayer. However, the results shown for the subject invention indicate that using one or more sprayers with ion lenses and applying a potential to the ion lenses to disable and enable the sprayers may be much more effective for generating small pulses of ions than the method disclosed by Lu et al., since using the potential applied to an ion lens disables and enables a sprayer much more quickly than using the potential applied to a sprayer (as taught by Lu et al.). Accordingly, a high speed switch, with a switching speed on the order of microseconds or nanoseconds, may be incorporated into the subject invention between a power supply for an ion lens and the biasing means for that ion lens. The high speed switch may be automatically controlled via software means, such as a LABVIEW™ program, and AID and D/A means to provide a rapid alternating potential to the ion lens. Alternatively, it may be controlled by other means. It will be apparent to those skilled in the art that there are many methods for installing a high speed switch into a high voltage circuit. The potential applied to the ion lens would rapidly alternate between enabling and disabling potentials. The application of such a potential to an ion lens should result in the generation of ion pulses from the sprayer on which the ion lens is mounted.

Figure 24:
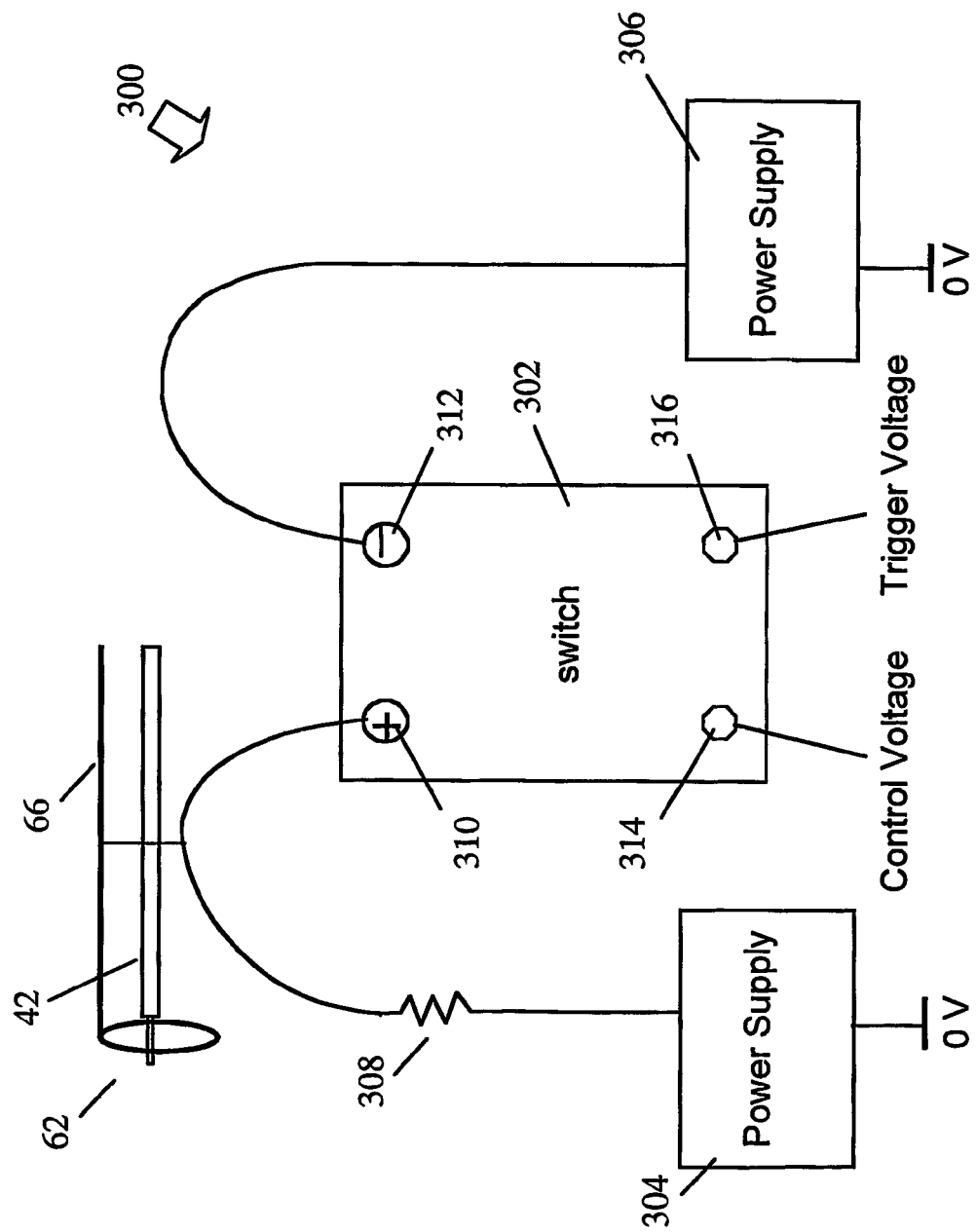
FIG. 24 is a partial view of an alternate embodiment of the dual sprayer apparatus of FIG. 2 having a switching means to implement a pulsed electrospray ion source; and, FIG. 25 is a partial view of an alternate embodiment of the dual sprayer apparatus of FIG. 2 having an alternate switching means to implement a pulsed electrospray ion source.

Referring now to FIG. 24, shown therein is a partial view of the dual sprayer apparatus 40' of FIG. 2 modified to include a switching means 300 to implement a pulsed ion spray ion source. The switching means 300 comprises a switch 302, two power supplies 304 and 306 that are connected to the switch 302 and a resistive element 308 that couples the power supply 304 to the switch 302 and to the mounting bracket 66. The power supply 304 may be used to apply a disabling potential, such as 8000 V for example, to the mounting bracket 66 and the power supply 306 may be used to provide an enabling potential, such as 4500 V for example, to the mounting bracket 66. The power supplies 304 and 306 are connected to the positive and negative terminals 310 and 312 of the switch 302. The switch 302 also has input terminals 314 and 316 for the reception of a control voltage and a trigger voltage respectively. The switch 302 is chosen to withstand high potentials and may preferably be chosen to have a tolerance of 10 kV. The switch 302 may be a commercially available high speed switch preferably capable of switching on the order of tens of nanoseconds. The resistive element 308 may be a resistor or any resistive network having a high resistance preferably on the order of 100 MΩ. In use, the switch 302 may initially be in the open position in which case the disabling potential is applied through the resistive element 308 to the mounting bracket 66. The switch may then be closed to provide the enabling potential to the mounting bracket 66.

Figure 25:
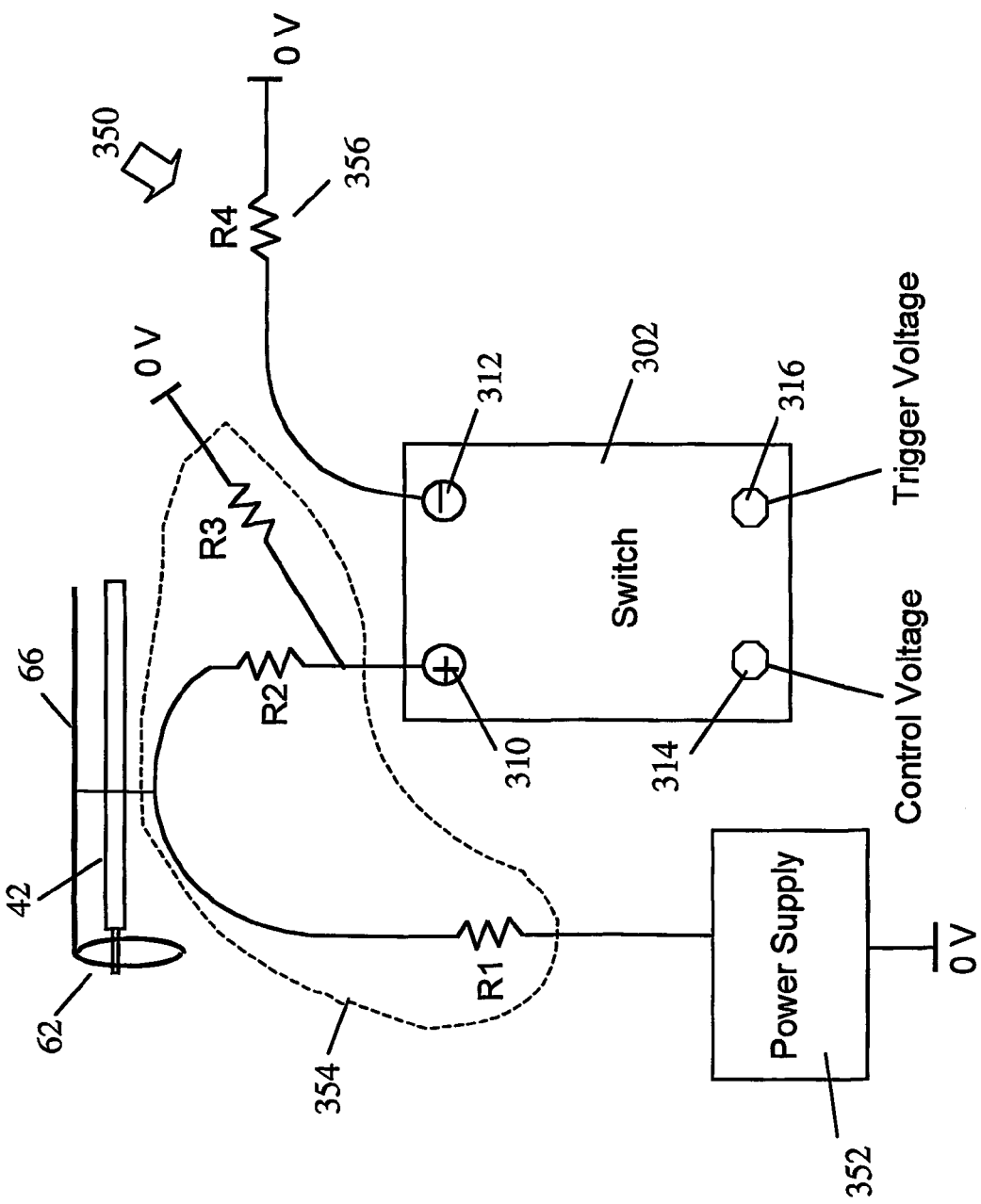

Referring now to FIG. 25, shown therein is a partial view of another alternative embodiment of the dual sprayer apparatus 40 of FIG. 2 modified to include an alternative switching means 350 to implement a pulsed ion spray ion source. In this embodiment, the switching means 350 comprises a power supply 352, a resistive element 354, the switch 302 and a resistive element 356. The power supply 352 is connected to the positive terminal 310 of the switch 302 and the mounting bracket 66 through the resistive element 354. The resistive element 356 is connected between ground and the negative input 312 of the switch 302. In this embodiment, the resistive element 354 is a resistor network comprising resistors R1, R2 and R3, and the resistive element 356 is a resistor R4. The potential applied to the mounting bracket 66 is dependent on the voltage provided by the power supply 352, and the resistances of the resistors R1, R2, R3 and R4. These values may be chosen depending on the desired magnitude of the enabling and disabling potentials. For instance, the voltage provided by the power supply 352 may be chosen to be 18000 V and the resistances for R1, R2, R3 and R4 may be chosen to be 214.3 MΩ, 71.4 MΩ, 100 MΩ and 1 KΩ respectively. In this case, the enabling potential would be 4500 V and the disabling potential would be 8000 V.

In use, assuming the resistance values and the power supply value given above, with the switch 302 initially open, the potential applied to the mounting bracket 66 is 8000 V. When the switch 302 is triggered to close, the potential applied to the mounting bracket 66 decreases to 4500 V. The current, which in this case is 4.66 A, will rapidly dissipate through the switch 302 and the resistor R4 to ground when the switch closes. Accordingly, the resistor R4 is chosen to withstand high current. However, since the current will dissipate quickly when the switch 302 closes, the resistor R4 only needs to withstand the high current briefly. In addition, because the switch 302 is not subjected to high potentials, a 5 kV switch is sufficient for this embodiment, unlike the embodiment described in FIG. 24.

The multiple sprayer ion source 10 may thus be considered to have an alternating means for alternating an ion controlling element (i.e. ion lens) between a first condition, where the ion controlling element enables ion generation by one or more ion sources (i.e. sprayers) that the ion controlling element is mounted relative to, and a second condition, where the ion controlling element disables ion generation by the, one or more ion sources that the ion controlling element is mounted relative to. As previously described herein, the alternating means may comprise an enabling potential applied to the ion controlling element in the first condition and a disabling potential applied to the ion controlling element in the second condition. Alternatively, the alternating means may comprise a translation means that translates the ion controlling element to an enabling position in the first condition and to a disabling position in the second condition. In a further alternative, the alternating means may comprise a combination of a translation means, to move the ion controlling element to the enabling position, and applying an enabling potential to the ion controlling element in the first condition and a combination of a translation means, to move the ion controlling element to the disabling position, and applying a disabling potential to the ion controlling element in the second condition. In addition, the alternating means, may comprise a switching means that is connectable to the ion controlling element for providing a rapidly alternating potential to the ion controlling element to effect the generation of ion pulses. As previously mentioned, each of these concepts may be applied to a single sprayer ion source having an ion lens mounted relative to the sprayer.

The multiple sprayer ion source 10 may also be used to investigate ion-ion chemistry. For instance, one or more of the sprayers may be-enabled to generate positive ions such as protein ions. These positive ions would travel through the atmospheric pressure source region in the source housing and enter the inlet aperture of a downstream mass spectrometer. One or more of the other sprayers may then be enabled in negative ion mode to generate negative ions. The negative ions would not enter the downstream mass spectrometer but would rather be attracted to the large positive potential applied to the sprayer generating the positive ions. The positive ions and the negative ions would then mix and result in the generation of complexes. Accordingly, if positively charged proteins and negatively charged ligands were generated simultaneously, it may be possible to investigate the type of complexes that would form or to reduce the overall charge of the generated proteins. However, the placement of a grid between the sprayers and the entrance aperture of a downstream mass spectrometer may be necessary to isolate the sprayers from each other and the downstream mass spectrometer.

In a further alternative embodiment, the multisprayer ion source 10 may use multiple reduced flow-rate sprayers or multiple nanosprayers. In these two cases, the orientations of these sprayers will likely be different than the orientations of the sprayers of the dual sprayer apparatus 40 to achieve acceptable ion transmission through any downstream apertures. For instance, the reduced flow-rate sprayers or the multiple nanosprayers will likely need to be positioned close to any apertures in the source housing. In addition, the use of reduced flow-rate sprayers or nanosprayers may result in a droplet forming at the tip of disabled sprayers. In this case, a nebulizer gas may be used to blow away these droplets before the disabled sprayer is re-enabled.

The multisprayer ion source 10 may also be applied to a mass spectrometer having multiple inlet orifices in which the ion lenses mounted on each sprayer could be used to enable or disable the sprayers and to allow any downstream ion lenses within the mass spectrometer to be tuned for maximum transmission of ions generated from each ion spray. This should increase the sensitivity of the mass spectrometer system. In this case, a single sprayer or multiple sprayers may be located in front of each inlet orifice.

Other uses for the multisprayer ion source 10 include, but are not limited to, investigating controlled deposition of reagents, inks, or paints. This invention may also be applied to other applications in which ions are generated by other ion sources, as previously mentioned, including, but not limited to, electrospray sources, reduced liquid flow rate electrospray sources, reduced liquid flow rate ion spray sources, Turbo IonSpray™ sources, other heated electrospray or ion spray sources, and nanospray sources.

It should be understood that the specific embodiments described herein are provided for illustrative purposes only and in no way are intended to limit the spirit or scope of the invention. Various modifications can be made to the preferred embodiments described and illustrated herein, without departing from the present invention, the scope of which is defined in the appended claims.

The invention claimed is:

1. An apparatus for controlling generation of ions, said apparatus comprising: a) at least one ion source adapted for generating said ions from a sample; b) at least one counter electrode located downstream from said at least one ion source, said at least one ion source and said at least one counter electrode adapted to enable downstream movement of said ions upon application of a first potential difference there between; and, c) at least one ion controlling element mounted relative to said at least one ion source, said at least one ion controlling element having, in use, a potential applied thereto to provide a second potential difference between the at least one ion controlling element and the at least one ion source, wherein said at least one ion controlling element is operable in a first condition where said at least one ion controlling element allows ion generation by said at least one ion source and a second condition where said at least one ion controlling element disables ion generation by said at least one ion source, wherein, the apparatus includes alternating means for alternating said at least one ion controlling element between said first condition and said second condition.

2. The apparatus of claim 1, wherein said alternating means is configured to provide the second potential difference as an enabling potential applied to said at least one ion controlling element in said first condition and as a disabling potential applied to said at least one ion controlling element in said second condition.

3. The apparatus of claim 1, wherein said alternating means comprises a translation means operatively coupled to said at least one ion controlling element to translate said at least one ion controlling element to an enabling position in said first condition and to a disabling position in said second condition.

4. The apparatus of claim 1, wherein said alternating means comprises a switching means connectable to said at least one ion controlling element for providing a rapidly alternating potential to said at least one ion controlling element, whereby said at least one ion source is adapted to generate ion pulses.

5. The apparatus of claim 2, wherein said apparatus comprises a plurality of ion sources and said at least one ion controlling element is mounted relative to at least one of said plurality of ion sources.

6. The apparatus of claim 2, wherein said apparatus comprises a plurality of ion sources and a plurality of ion controlling elements, wherein at least two of said plurality of ion controlling elements are mounted relative to one of said plurality of ion sources.

7. The apparatus of claim 2, wherein said apparatus comprises a plurality of ion sources and a plurality of ion controlling elements, wherein each of said plurality of ion controlling elements is mounted relative to each of said plurality of ion sources.

8. The apparatus of any one of claims 2, 3 or 4, wherein said apparatus comprises one ion source and one ion controlling element, said ion controlling element is mounted relative to said ion source.

9. The apparatus of any one of claims 5, 6 or 7, wherein said apparatus further comprises at least one electrode means located centrally with respect to said plurality of ion sources, said at least one electrode means being adapted for isolating each ion source from potentials applied to other ion sources and ion controlling elements mounted relative to the other ion sources.

10. The apparatus of claim 1, wherein said at least one ion controlling element comprises an ion lens and an attachment means, said attachment means is adapted to provide a potential to said ion lens.

11. The apparatus of claim 10, wherein said ion lens is mounted to substantially surround said at least one ion source.

12. The apparatus of claim 10, wherein said at least one ion source has a tip and said ion lens is located behind said tip.

13. The apparatus of claim 12, wherein said ion lens is located 0.1 mm to 5 mm behind said tip.

14. The apparatus of claim 12 wherein said ion lens is located 1 to 3 mm behind said tip.

15. The apparatus of claim 12, wherein said ion lens is located 2 mm behind said tip.

16. The apparatus of any one of claims 10 to 15, wherein said ion lens has an aperture having at least one adjustable dimension.

17. The apparatus of claim 1, wherein said at least one ion source, said at least one ion controlling element, and said at least one counter electrode are mounted in a housing.

18. The apparatus of claim 17, wherein said housing provides said at least one counter electrode.

19. The apparatus of claim 17 or 18, wherein said apparatus includes an orifice plate having an orifice, and a curtain plate having an aperture, said orifice plate is adapted for closing off said housing.

20. The apparatus of claim 17 or 18, wherein said apparatus includes a curtain plate having an aperture, said curtain plate is adapted for closing off the housing, and said apparatus is removably connectable to a mass spectrometer having an orifice plate as part of an inlet.

21. The apparatus of claim 17 or 18, wherein said apparatus is removably connectable to a mass spectrometer having an inlet capillary.

22. The apparatus of any one of claims 1 to 7, 10 to 15, 17 or 18, wherein said apparatus further comprises at least one power supply connectible in use to said at least one ion source, said at least one ion controlling element, and said at least one counter electrode, said at least one power supply being adapted to provide different DC potentials thereto.

23. The apparatus of any one of claims 5, 6 or 7, wherein said apparatus further comprises a power supply means to provide a separate potential to each of said plurality of ion sources.

24. The apparatus of any one of claims 5, 6 or 7, wherein said apparatus further comprises: a) a sprayer mount; b) a plurality of sprayer mounting means for adjustably mounting each of said plurality of ion sources to said sprayer mount; c) a biasing means for applying a potential to each of said plurality of ion sources; and, d) a sample delivery means for providing a sample to each of said plurality of ion sources.

25. The apparatus of claim 24, wherein each sprayer mounting means is a sprayer tee.

26. The apparatus of claim 24, wherein at least one of said plurality of ion sources is an electrospray ion source.

27. The apparatus of claim 24, wherein at least one of said plurality of ion sources is a nanospray ion source.

28. The apparatus of claim 24, wherein at least one of said plurality of ion sources is a reduced flow-rate electrospray ion source.

29. The apparatus of claim 24, wherein at least one of said plurality of ion sources is an ion spray ion source, said apparatus further comprising a nebulizer gas delivery means for providing nebulizer gas to said ion spray ion source and a heated element to provide heat to said nebulizer gas.

30. The apparatus of claim 24, wherein at least one of said plurality of ion sources is an ion spray ion source, said apparatus further comprising a nebulizer gas delivery means for providing nebulizer gas to said ion spray ion source.

31. The apparatus of claim 30, wherein said ion spray ion source comprises an inner capillary, a middle capillary, and an outer capillary, wherein said sample flows within said inner capillary and said nebulizer gas delivery means is in fluid communication with an annular region defined between said middle capillary and said outer capillary.

32. The apparatus of claim 24, wherein said apparatus further comprises an attachment piece, said attachment piece is removably connectable to said sprayer mount for connecting additional ion sources to said apparatus.

33. The apparatus of claim 32, wherein said sprayer mount further comprises a slot and a plurality of mounting apertures, and said attachment piece comprises: a) a plate; b) at least one of said additional ion sources mounted on said plate; and, c) a retaining means for securably coupling said attachment piece to said sprayer mount, said retaining means being connected to said plate, wherein, said slot is adapted to slidably receive said plate such that said retaining means rests on said sprayer mount and said retaining means connects with said mounting apertures.

34. The apparatus of claim 24, wherein said ion sources are oriented at an angle with respect to a downstream orifice adapted to receive ions generated by said ion sources.

35. The apparatus of claim 24, wherein said ion sources are oriented orthogonally with respect to a downstream orifice adapted to receive ions generated by said ion sources.

36. The apparatus of claim 34, wherein said ion source is a sprayer having a straight shaft.

37. The apparatus of claim 34, wherein said ion source is a sprayer having a curved shaft.

38. The apparatus of any one of claims 5, 6 or 7, wherein said apparatus further comprises an electrical insulation means located centrally with respect to said plurality of ion sources.

39. The apparatus of claim 3, wherein said translation means comprises a rotation means, a threaded shaft operatively coupled to said rotation means, a moveable plate movably mounted onto said threaded shaft and a threaded block operatively coupled to the end of said threaded shaft, wherein, said moveable plate is coupled to said at least one ion controlling element via a coupling element, and said rotation means is adapted to rotate said threaded shaft to translate said moveable plate along the longitudinal axis of said threaded shaft thereby imparting motion to said ion controlling element.

40. The apparatus of claim 4, wherein said switching means comprises a switch, a first power supply, a resistive element having a first terminal coupled to said first power supply and a second terminal coupled to said ion controlling element and said switch, and a second power supply connectable to said switch, wherein, in use, said first power supply is adapted to provide the disabling potential to said ion controlling element and said second power supply is adapted to provide the enabling potential to said ion controlling element.

41. The apparatus of claim 4, wherein said switching means comprises a switch, a power supply, a first resistive element adapted to connect said power supply and said switch to said ion controlling element, and a second resistive element having a first terminal connected to a first terminal of said switch and a second terminal connected to ground, wherein, in use, said first power supply in combination with said first resistive element is adapted to provide the disabling potential to said ion controlling element, and said first power supply in combination with said first and second resistive elements is adapted to provide the enabling potential to said ion controlling element.

42. The apparatus of claim 41, wherein said first resistive element is a resistor network comprising first, second and third resistors, each resistor having a first and a second terminal, and said second resistive element comprises a fourth resistor, wherein said first terminal of said first resistor is coupled to said power supply and said second terminal of said first resistor is coupled to said ion controlling element, said first terminal of said second resistor is coupled to said second terminal of said first resistor and said ion controlling element and said second terminal of said second resistor is coupled to a second terminal of said switch, and said first terminal of said third resistor is coupled to said second terminal of said second resistor and said second terminal of said switch, and said second terminal of said third resistor is coupled to ground.

43. A method for controlling ion generation from a sample, said method comprising: a) supplying said sample to at least one ion source; b) generating ions from said sample by applying a first potential difference between said at least one ion source and at least one counter electrode situated downstream from said at least one ion source; c) applying a potential to at least one ion controlling element, said ion controlling element being mounted relative to said at least one ion source to provide a second potential difference there between; and, d) alternating said at least one ion controlling element between a first condition where ion generation by said at least one ion source is allowed and a second condition where ion generation by said at least one ion source is disabled.

44. The method of claim 43, wherein alternating said at least one ion controlling element between said first condition and said second condition is effected by applying an enabling potential to said at least one ion controlling element in said first condition and applying a disabling potential to said at least one ion controlling element in said second condition.

45. The method of claim 43, wherein alternating said at least one ion controlling element between said first condition and said second condition is effected by moving said at least one ion controlling element to an enabling position in said first condition and moving said at least one ion controlling element to a disabling position in said second condition.

46. The method of claim 44, wherein pulses of ions are generated by rapidly applying said enabling potential and said disabling potential to said at least one ion controlling element in an alternating fashion.

47. The method of claim 44, wherein there are a plurality of ion sources and ion controlling elements, and said method further comprises providing a potential to at least one electrode means located centrally with respect to the plurality of ion sources for isolating each ion source from potentials applied to other ion sources and ion controlling elements mounted relative to the other ion sources.

48. The method of claim 47, wherein a different enabling potential is provided to each of said plurality of ion sources that is allowed to operate for increasing the number of ions generated therefrom.

49. The method of claim 44, wherein there are a plurality of ion sources and ion controlling elements and said method further comprises:
 e) providing similar analyte samples to each of said plurality of ion sources; and, f) simultaneously operating each of said plurality of ion controlling elements in said first condition for simultaneously allowing said plurality of ion sources to generate said ions, whereby, the overall flux of said analyte ions is increased.

50. The method of claim 44, wherein there are a plurality of ion sources and ion controlling elements and said method further comprises:
 e) providing different analyte samples to each of said plurality of ion sources; and, f) sequentially operating each of said plurality of ion controlling elements in said first condition for sequentially allowing said plurality of ion sources to sequentially generate different analyte ions, whereby, higher throughput analysis of said different analyte samples is facilitated.

51. The method of claim 44, wherein there are a plurality of ion sources and ion controlling elements and said method further comprises:
 e) providing different analyte samples to each of said plurality of ion sources; and, f) simultaneously operating each of said plurality of ion controlling elements in said first condition for simultaneously allowing said plurality of ion sources to generate different analyte ions, whereby, higher throughput analysis of said different analyte samples is facilitated.

52. The method of claim 44, wherein there are a plurality of ion sources and ion controlling elements and said method further comprises:
 e) providing an analyte sample to at least one of said plurality of ion sources and providing at least one mass calibrant to at least one other ion source from said plurality of ion sources; f) simultaneously operating each of said plurality of ion controlling elements in said first condition for allowing said plurality of ion sources to simultaneously generate analyte ions and mass calibrant ions; and, g) passing said analyte ions and said mass calibrant ions into a mass analyzer for mass analysis, whereby, said mass calibrant ions are used to calibrate the mass analyzer.

53. The method of claim 44, wherein there are a plurality of ion sources and ion controlling elements and said method further comprises:
 e) providing an analyte sample to at least one of said plurality of ion sources and providing at least one internal standard to at least one other ion source from said plurality of ion sources; f) simultaneously operating each of said plurality of ion controlling elements in said first condition for allowing said plurality of ion sources to simultaneously generate analyte ions and internal standard ions; and, g) passing said analyte ions and said internal standard ions into a mass analyzer for mass analysis, whereby, said internal standard ions aid in assessing ion source efficiency and analyte quantification.

54. The method of any one of claims 43 to 48, wherein said method further comprises the step of providing said ions to a downstream mass analysis device for analysis.

55. The method of claim 44, wherein said method further comprises generating ions of one polarity from at least one of said plurality of ion sources and generating ions of the opposite polarity from at least one other ion source from said plurality of ion sources to investigate ion-ion chemistry.

56. An apparatus for controlling generation of ions, said apparatus comprising:
 a) at least one ion source adapted for generating said ions from a sample;
 b) at least one counter electrode located downstream from said at least one ion source;
 c) at least one ion controlling element electrically insulated from said at least one ion source, said at least one controlling element comprising an ion lens mounted relative to said at least one ion source; and
 d) alternating means for alternating said at least one ion controlling element between a first condition and a second condition;
wherein, in use, a potential difference is applied between said at least one ion source and said at least one counter electrode to generate downstream movement of said ions and an additional potential is applied between said at least one ion controlling element and said at least one ion source, wherein in the first condition said at least one ion controlling element is adapted to disable ion generation by said at least one ion source and in the second condition said at least one ion controlling element is adapted to re-enable ion generation by said at least one ion source when previously disabled.

57. The apparatus of claim 56, wherein a first ion source is enabled to generate a first plurality of ions of one polarity and a second ion source is simultaneously enabled to generate a second plurality of ions of the opposite polarity, wherein, in use, the first and second plurality of ions are mixed in an atmospheric pressure source region and subsequently mass analyzed.

58. A method for controlling ion generation from samples, said method comprising:
 supplying a first sample to a first ion source;
 supplying a second sample to a second ion source;
 generating a first plurality of ions having one polarity from said first sample by applying a first potential difference between said first ion source and at least one counter electrode situated downstream from said first ion source;
 generating a second plurality of ions from said second sample by applying a second potential difference between said second ion source and said at least one counter electrode situated downstream from said second ion source, the second plurality of ions having an opposite polarity compared to the first plurality of ions to investigate ion-ion chemistry;
 applying a potential to a first ion controlling element mounted relative to the first ion source to provide a third potential difference there between;
 applying an additional potential to a second ion controlling element mounted relative to the second ion source to provide a fourth potential difference there between;
 alternating said first ion controlling element between a first condition where ion generation by said first ion source is allowed and a second condition where ion generation by said first ion source is disabled; and
 alternating said second ion controlling element between a third condition where ion generation by said second ion source is allowed and a fourth condition where ion generation by said second ion source is disabled.

59. The method of claim 58, wherein the first and second plurality of ions are mixed in an atmospheric pressure source region prior to mass analysis.

60. The apparatus of claim 17, wherein the apparatus further comprises at least one heating element positioned in the housing to aid in desolvation.

61. The method of claim 43, wherein the method further comprises using at least one heating element to aid in desolvation.

62. The method of claim 44, 47 or 48, wherein there are a plurality of ion sources and ion controlling elements and said method further comprises: e) providing an analyte sample to at least one of said plurality of ion sources and providing at least one mass calibrant to at least one other ion source from said plurality of ion sources; f) sequentially operating each of said plurality of ion controlling elements in said first condition for allowing said plurality of ion sources to sequentially generate mass calibrant ions followed by analyte ions; and g) passing said mass calibrant ions into a mass analyzer for calibration and then passing said analyte ions into said mass analyzer for mass analysis.

63. The method of claim 44, 47 or 48, wherein there are a plurality of ion sources and ion controlling elements and said method further comprises: e) providing an analyte sample to at least one of said plurality of ion sources and providing at least one internal standard to at least one other ion source from said plurality of ion sources; f) sequentially operating each of said plurality of ion controlling elements in said first condition for allowing said plurality of ion sources to sequentially generate internal standard ions followed by analyte ions; and, g) passing said internal standard ions into a mass analyzer followed by passing said analyte ions into said mass analyzer for mass analysis, whereby, said internal standard ions aid in assessing ion source efficiency and analyte quantification.

64. The apparatus of claim 56, wherein the at least one ion source is a reduced-flow rate sprayer and the apparatus further comprises a nebulizer gas to prevent droplet accumulation at a tip of the reduced-flow rate sprayer when the reduced-flow rate sprayer is disabled.

65. The method of claim 58, wherein one of the ion sources is a reduced-flow rate sprayer and the method further comprises using a nebulizer gas to prevent droplet accumulation at a tip of the reduced-flow rate sprayer when the reduced-flow rate sprayer is disabled.

66. The apparatus of claim 64, wherein the apparatus comprises an additional ion source angled towards the reduced-flow rate sprayer, whereby, in use, the additional ion source is allowed to operate, the reduced-flow rate sprayer is disabled and ions generated from the operational ion source intersect with a neutral nebulized spray from the disabled reduced-flow rate sprayer and are mass analyzed.

67. The method of claim 65, wherein the method further comprises angling an additional ion source towards the reduced-flow rate sprayer, allowing the additional ion source to operate, disabling the reduced-flow rate sprayer and analyzing ions generated from the operational ion source that have intersected with a neutral nebulized spray from the disabled reduced-flow rate sprayer with a mass analyzer.

68. The method of claim 58, wherein the first and second plurality of ions are generated sequentially.

69. The apparatus of claim 30, wherein the plurality of ion sources comprise a first ion source having a first axis and a second ion source having a second axis adapted to intersect with the first axis, wherein, during use output from enabled and disabled ion sources intersect in the atmospheric pressure region prior to mass analysis.

70. The apparatus of claim 56, wherein a first ion source is enabled to generate a first plurality of ions of one polarity and a second ion source is sequentially enabled to generate a second plurality of ions of the opposite polarity, wherein, in use, the first and second plurality of ions are subsequently mixed and mass analyzed.

71. The apparatus of claim 35, wherein said ion source is a sprayer having a straight shaft.

72. The apparatus of claim 35, wherein said ion source is a sprayer having a curved shaft.

73. The method of claim 44, wherein there are a plurality of ion sources and ion controlling elements, and said method further comprises generating ions of one polarity from at least one of said plurality of ion sources and generating ions of the opposite polarity from at least one other ion source from said plurality of ion sources to investigate ion-ion chemistry.

74. The method of claim 47 or 48, wherein said method further comprises:
 e) providing similar analyte samples to each of said plurality of ion sources; and, f) simultaneously operating each of said plurality of ion controlling elements in said first condition for simultaneously allowing said plurality of ion sources to generate said ions, whereby, the overall flux of said analyte ions is increased.

75. The method of claim 47 or 48, wherein said method further comprises:
 e) providing different analyte samples to each of said plurality of ion sources; and, f) sequentially operating each of said plurality of ion controlling elements in said first condition for sequentially allowing said plurality of ion sources to sequentially generate different analyte ions, whereby, higher throughput analysis of said different analyte samples is facilitated.

76. The method of claim 47 or 48, wherein said method further comprises:
 e) providing different analyte samples to each of said plurality of ion sources; and, f) simultaneously operating each of said plurality of ion controlling elements in said first condition for simultaneously allowing said plurality of ion sources to generate different analyte ions, whereby, higher throughput analysis of said different analyte samples is facilitated.

77. The method of claim 47 or 48, wherein said method further comprises:
 e) providing an analyte sample to at least one of said plurality of ion sources and providing at least one mass calibrant to at least one other ion source from said plurality of ion sources; f) simultaneously operating each of said plurality of ion controlling elements in said first condition for allowing said plurality of ion sources to simultaneously generate analyte ions and mass calibrant ions; and, g) passing said analyte ions and said mass calibrant ions into a mass analyzer for mass analysis, whereby, said mass calibrant ions are used to calibrate the mass analyzer.

78. The method of claim 47 or 48, wherein said method further comprises:
 e) providing an analyte sample to at least one of said plurality of ion sources and providing at least one internal standard to at least one other ion source from said plurality of ion sources; f) simultaneously operating each of said plurality of ion controlling elements in said first condition for allowing said plurality of ion sources to simultaneously generate analyte ions and internal standard ions; and, g) passing said analyte ions and said internal standard ions into a mass analyzer for mass analysis, whereby, said internal standard ions aid in assessing ion source efficiency and analyte quantification.

* * * * *